United States Patent [19]

Hook

[11] Patent Number: 5,726,578
[45] Date of Patent: Mar. 10, 1998

[54] APPARATUS AND METHODS FOR TIME DOMAIN REFLECTOMETRY

[75] Inventor: William R. Hook, Shawnigan Lake, Canada

[73] Assignee: Precision Moisture Instruments, Inc., Shawnigan Lake, Canada

[21] Appl. No.: 335,101

[22] Filed: Nov. 17, 1994

Related U.S. Application Data

[62] Division of Ser. No. 71,748, Jun. 9, 1993, Pat. No. 5,376,888.

[51] Int. Cl.$^6$ .................................................. G01R 27/04
[52] U.S. Cl. .................... 324/643; 324/632; 324/601; 324/634; 324/647; 73/304 C
[58] Field of Search .................. 324/634, 601, 324/643, 644, 632; 73/304 R, 304 C, 290 R

[56] References Cited

U.S. PATENT DOCUMENTS

| | | |
|---|---|---|
| H395 | 12/1987 | Nash . |
| 3,551,677 | 12/1970 | Brewster . |
| 3,757,222 | 9/1973 | Oberbury . |
| 3,771,056 | 11/1973 | Zimmerman . |
| 3,789,296 | 1/1974 | Caruso, Jr. et al. . |
| 3,829,796 | 8/1974 | Bakken . |
| 3,853,005 | 12/1974 | Schendel . |
| 3,993,933 | 11/1976 | Menninga . |
| 3,995,212 | 11/1976 | Ross . |
| 4,013,950 | 3/1977 | Falls . |
| 4,109,117 | 8/1978 | Wrench, Jr. et al. . |
| 4,135,397 | 1/1979 | Krake . |

(List continued on next page.)

FOREIGN PATENT DOCUMENTS

| | | |
|---|---|---|
| 1444540 | 8/1976 | United Kingdom . |
| 2216355 | 10/1989 | United Kingdom . |
| WO 89/12820 | 12/1989 | WIPO . |

OTHER PUBLICATIONS

Alharthi, A. and Lange, J., Soil Water Saturation: Dielectric Determination, Water Resources Research, vol. 23, No. 4, pp. 591–595 (Apr., 1987).

(List continued on next page.)

*Primary Examiner*—Ernest F. Karlsen
*Assistant Examiner*—Jose M. Solis
*Attorney, Agent, or Firm*—J. Robert Cassidy

[57] ABSTRACT

Time Domain Reflectometry ("TDR") methods and apparatus for measuring propagation velocities of RF pulses to determine material liquid contents, moisture profiles, material levels and dielectric constants including: i) TDR probes and/or probe adaptors, including series averaging probes and multi-segment probes, all employing remotely operable, normally open, variable impedance devices such as diodes; ii) bias insertion and switching networks for rendering selected normally open variable impedance devices conductive one at a time to establish precise unambiguous timing markers $T_1 \ldots T_n$; iii) an RF cable coupling the probe to a TDR instrument; and, iv) a TDR instrument having: a) a variable impedance device Control Section including a Divide-By-2 circuit and a Diode Drive circuit; b) an RF section containing a Pulse Generator, a Sample-And-Hold circuit, and a Variable Delay circuit; c) a Synchronous Detection Section including a Repetition Rate Generator; filter, AC amplifiers, Analog Multiplier and Low Pass Filter connected in series and receiving sampled signals; d) a Delay circuit and AC amplifier for transmitting a Synchronous Detector Reference signal to the Multiplier; and e), capability for conditioning the TDR instrument to operate in a remotely shortable diode ON/OFF modulation mode or a Time Delay modulation mode. Repetitively sampled reflections are processed through a Synchronous Detection System to convert square wave signals generated by the Sample-And-Hold circuit into DC output signals V(T) representative of the difference function between reflections under shorted and open conditions and/or of the slope of the diode open reflection.

17 Claims, 13 Drawing Sheets

U.S. PATENT DOCUMENTS

| | | |
|---|---|---|
| 4,254,214 | 3/1981 | Bramanti et al. . |
| 4,281,285 | 7/1981 | Bastida . |
| 4,341,112 | 7/1982 | Mackay et al. . |
| 4,349,795 | 9/1982 | Kwok . |
| 4,755,769 | 7/1988 | Katz . |
| 4,782,313 | 11/1988 | Brant, Jr. . |
| 4,786,857 | 11/1988 | Mohr et al. . |
| 4,807,471 | 2/1989 | Courane et al. . |
| 4,918,375 | 4/1990 | Malicki et al. . |
| 4,949,076 | 8/1990 | Wann . |
| 5,376,888 | 12/1994 | Hook . |

OTHER PUBLICATIONS

Anon., Circuit Description, Tektronix 1502 TDR Instrument Operators and Maintenance Manual, Sect. 3, pp. 3–1–3–6 and Pulser/Sampler Drg. (rev.) (Jan., 1986).

Baker, J.M. and Allmaras, R.R., System for Automating and Multiplexing Soil Moisture Measurement by Time–Domain Reflectometry, Soil Science Society of America Journal, vol. 54, No. 1, pp. 1–6 (Jan.–Feb., 1990).

Baker, J.M. and Lascano, R.J., The Spatial Sensitivity of Time–Domain Reflectometry, Soil Science, vol. 147, No. 5, pp. 378–384 (May, 1989).

Dalton, F.N., Herkelrath, W.N., Rawlins, D.S. and Rhoades, J.D., Time–Domain Reflectometry: Simultaneous Measurement of Soil Water Content and Electrical Conductivity with a Single Probe, Science, vol. 224, pp. 989–990 (Mar. 1984).

Dalton, F.N. and van Genuchten, M.Th., The Time–Domain Reflectometry Method For Measuring Soil Water Content And Salinity, Geoderma, vol. 38, pp. 237–250 (Jun. 1986).

Dasberg, S. and Dalton, F.N., Time Domain Reflectometry Field Measurements of Soil Water Content and Electrical Conductivity, Soil Science Society of America, vol. 49, pp. 293–297 (Aug. 1985).

Dasberg, S. and Hopmans, J.W., Time Domain Reflectometry Calibration for Uniformly and Nonuniformly Wetted Sandy and Clayey Loam Soils, Soil Science Society of America Journal, vol. 56, pp.1341–1345 (Jan. 1992).

Fellner–Feldegg, H., The Measurement of Dielectrics in the Time Domain, The Journal of Physical Chemistry, vol. 73, No. 3, pp. 616–623 (Mar., 1969).

Grove, W.M., Sampling for Oscilloscopes and Other RF Systems: Dc Through X–Band, ISEE, Transactions on Microwave Theory and Techniques, vol. MTT–14, No. 12 (Dec., 1966).

Heimovaara, T.J. and Bouten, W., A Computer–Controlled 36–Channel Time Domain Reflectometry System for Monitoring Soil Water Contents, Water Resources Research, vol. 26, No. 10, pp. 2311–2316 (Oct., 1990).

Hook, W.R., Livingston, N.J., Sun, Z.J. and Hook, P.B., Remote Diode Shorting Improves Measurement of Soil Water by Time Domain Reflectometry, Soil Science of America Journal, vol. 56, pp. 1384–1391 (Sep.–Oct., 1992).

Kachanoski, R.G., Pringle, E. and Ward, A., Field Measurement of Solute Travel Times Using Time Domain Reflectometry, Soil Science Society of America Journal, vol. 56, pp. 47–52 (Aug. 1992).

Ledieu, J., de Ridder, P., de Clerck, P. and Dautrebande, S., A Method of Measuring Soil Moisture By Time–Domain Reflectometry, Journal of Hydrology, vol. 88, pp. 319–328 (Feb. 1986).

Malicki, M.A. and Skierucha, W.M., A Manually Controlled TDR Soil Moisture Meter Operating With 300ps Rise–Time Needle Pulse, Proceedings of International Conference on Measurement of Soil and Plant Water Status, vol. 1–Soils, pp. 103–109, Academic Press, Inc. (Jun. 1987).

Nadler, A., Dasberg, S. and Lapid, I., Time Domain Reflectometry Measurements of Water Content and Electrical Conductivity of Layered Soil Columns, Soil Science Society of American Journal, vol. 55, pp. 938–943 (Jul.–Aug., 1991).

Rhoades, J.D., Raats, P.A.C. and Prather, R.J., Effects of Liquid–phase Electrical Conductivity, Water Content, and Surface Conductivity on Bulk Soil Electrical Conductivity, Soil Science Society of America Journal, vol. 40, pp. 651–655 (Jun. 1976).

Rhoades, J.D. and van Schilfgaarde, J., An Electrical Conductivity Probe for Determining Soil Salinity, Soil Science Society of America Journal, vol. 40, pp. 647–651 (Jul. 1976).

Roth, K., Schulin, R., Flühler, H. and Attinger, W., Calibration of Time Domain Reflectometry for Water Content Measurement Using a Composite Dielectric Approach, Water Resources Research, vol. 26, No. 10, pp. 2267–2273 (Oct., 1990).

Topp, G.C., The Application of Time–Domain Reflectometry (TDR) To Soil Water Content Measurement, Proceedings of International Conference on Measurement of Soil and Plant Water Status, vol. 1–Soils, pp. 85–93, Academic Press, Inc. (Oct. 1987).

Topp, G.C., Davis, J.L. and Annan, A.P., Electromagnetic Determination of Soil Water Content: Measurements in Coaxial Transmission Lines, Water Resources Research, vol. 16, No. 3, pp. 574–582 (Jun., 1980).

Topp, G.C., Davis, J.L. and Annan, A.P., Electromagnetic Determination of Soil Water Content Using TDR:II. Evaluation of Installation and Configuration of Parallel Transmission Lines, Soil Science Society of America Journal, vol. 46, pp. 672–678 (Feb. 1982).

Topp, G.C. and Davis, J.L., Time–Domain Reflectometry (TDR) And Its Application To Irrigation Scheduling, Advances in Irrigation, vol. 3, pp. 107–127, Academic Press, Inc. (Jun. 1985).

Topp, G.C. and Davis, J.L., Measurement of Soil Water Content using Time–domain Reflectrometry (TDR): A Field Evaluation, Soil Science Society of America Journal, vol. 49, pp. 19–24 (Aug. 1985).

Topp, G.C., Yanuka, M., Zebchuk, W.D. and Zegelin, S., Determination of Electrical Conductivity Using Time Domain Reflectometry: Soil and Water Experiments in Coaxial Lines, Water Resources Research, vol. 24, No. 7, pp. 945–952 (Jul., 1988).

Wraith, J.M. and Baker, J.M., High–Resolution Measurement of Root Water Uptake Using Automated Time–Domain Reflectometry, Soil Science Society of America Journal, vol. 55, pp. 928–932 (Jul. 1991).

Yanuka, M., Topp, G.C., Zegelin, S. and Zebchuk, W.D., Multiple Reflection and Attenuation of Time Domain Reflectometry Pulses: Theoretical Considerations for Applications to Soil and Water, Water Resources Research, vol.24, No. 7, pp. 939–944 (Jul., 1988).

Zegelin, S.J., White, I. and Jenkins, D.R., Improved Field Probes for Soil Water Content and Electrical Conductivity Measurement Using Time Domain Reflectometry, Water Resources Research, vol. 25, No. 11, pp. 2367–2376 (Nov., 1989).

Zimmerman, A., The State Of The Art In Sampling, Tektronix Service Scope, No. 52, pp. 1–7 (Oct., 1968).

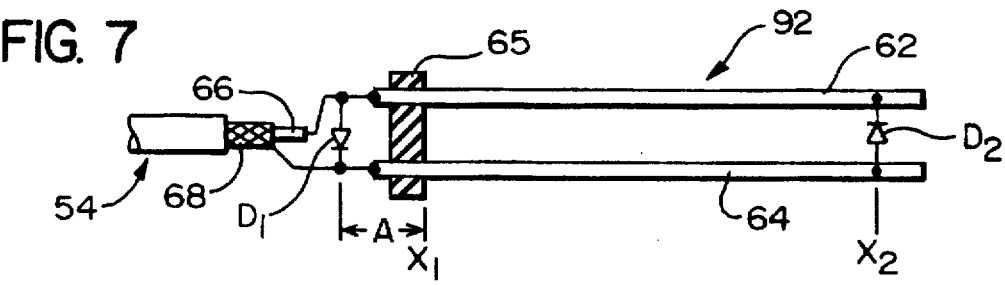
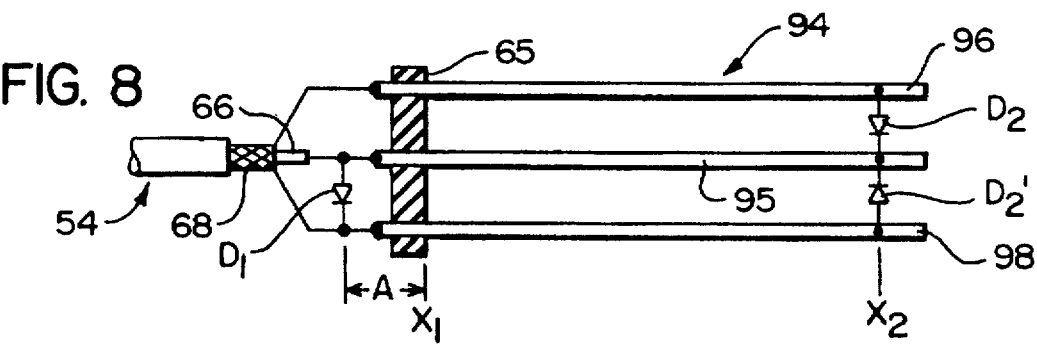
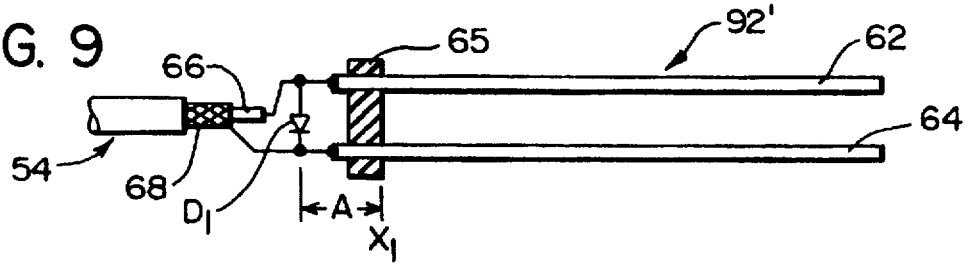
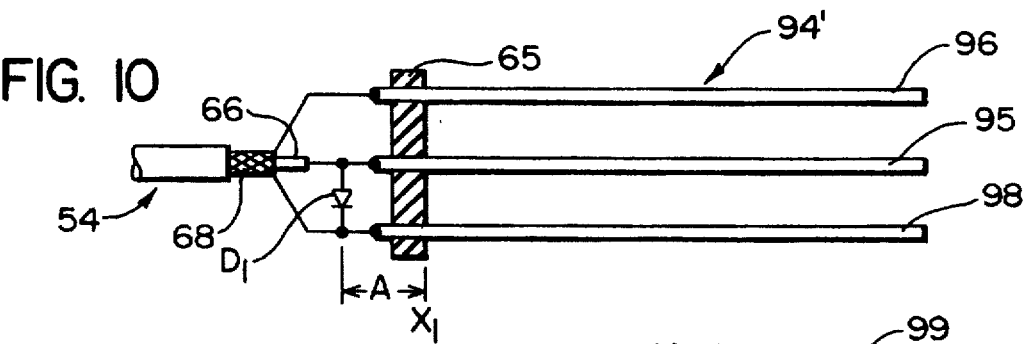
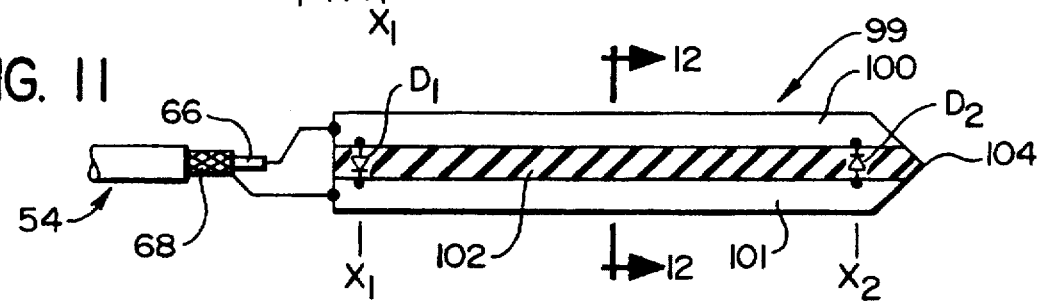
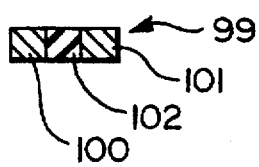

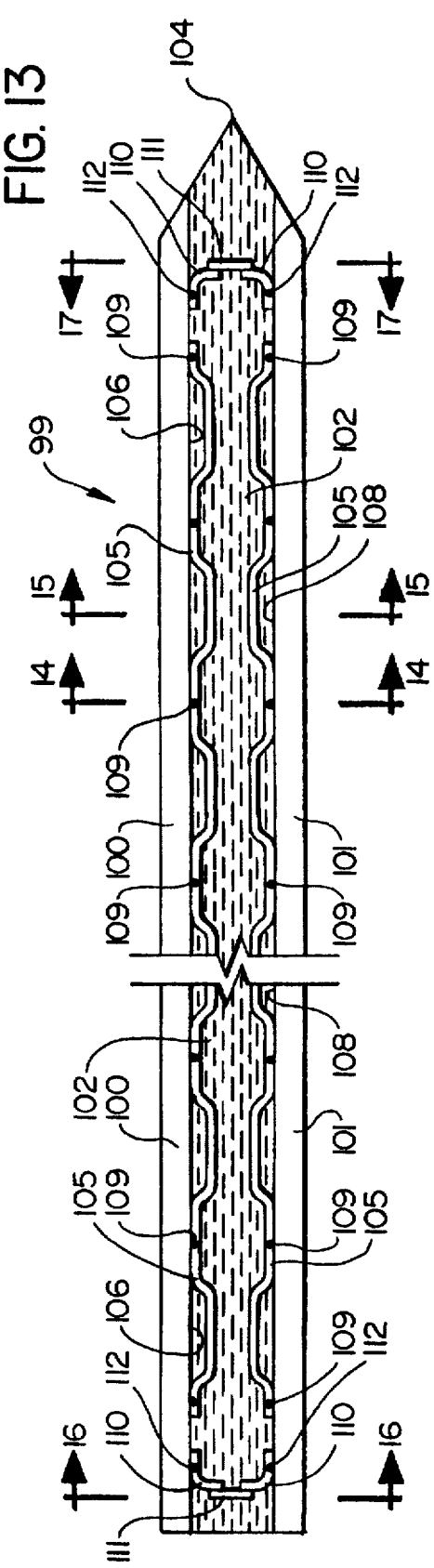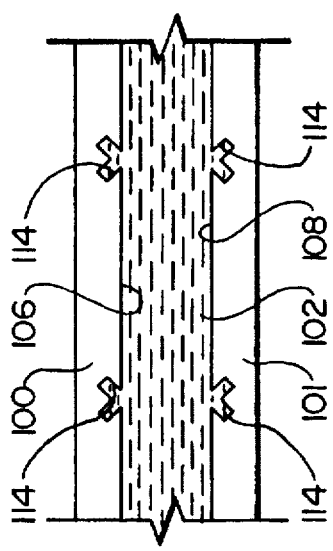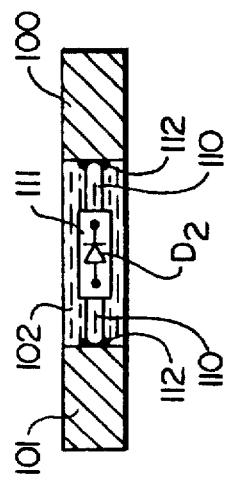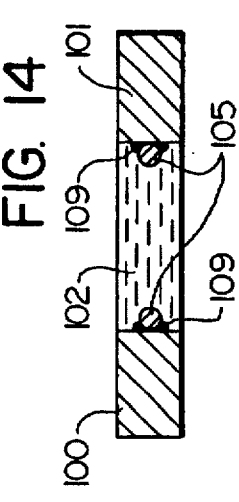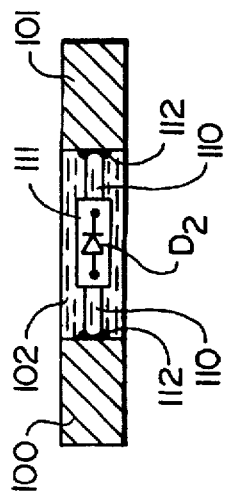

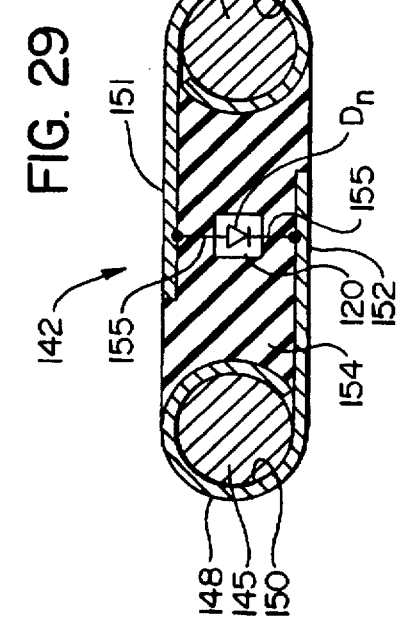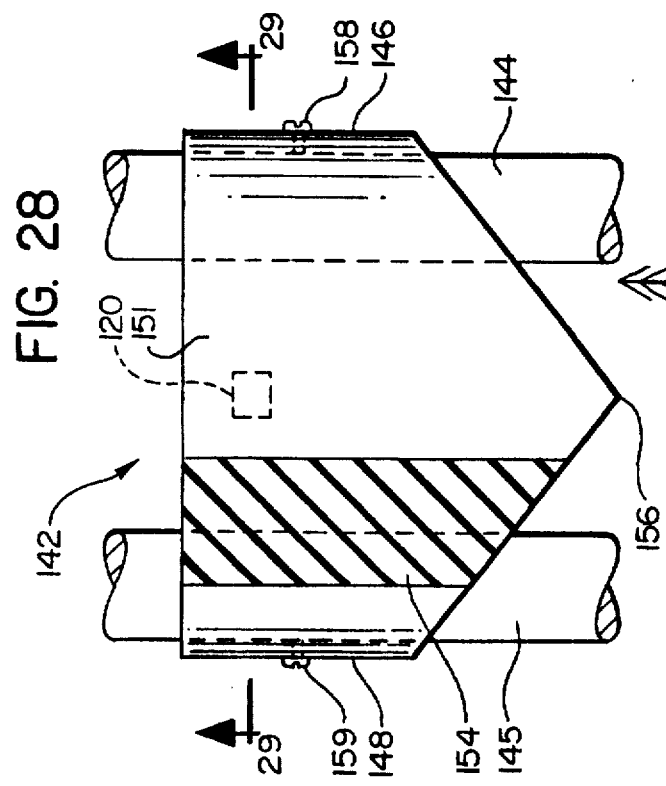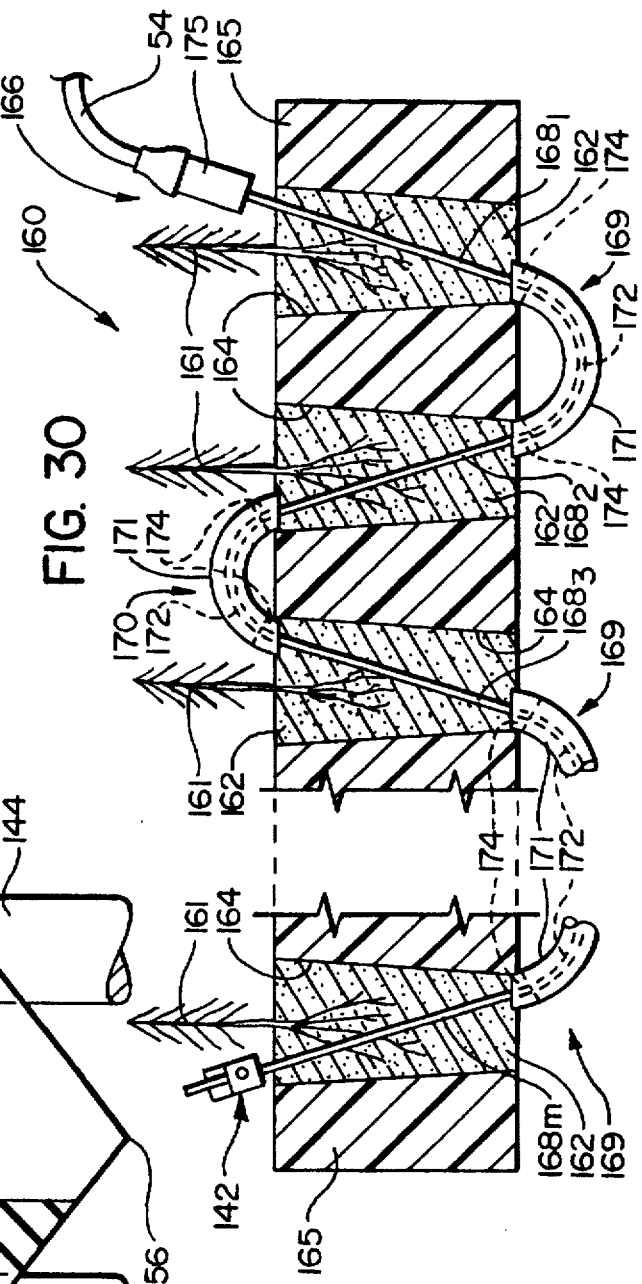

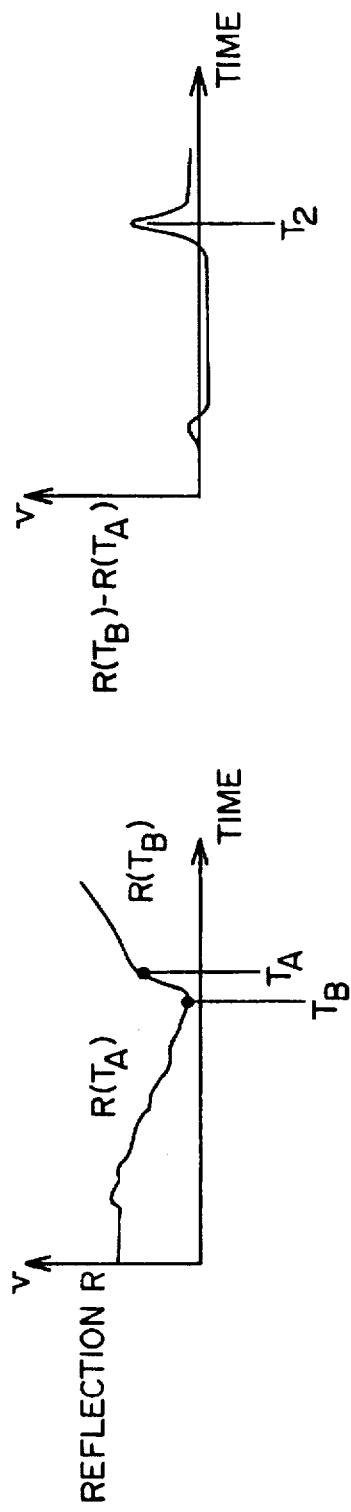
FIG. 33
FIG. 34
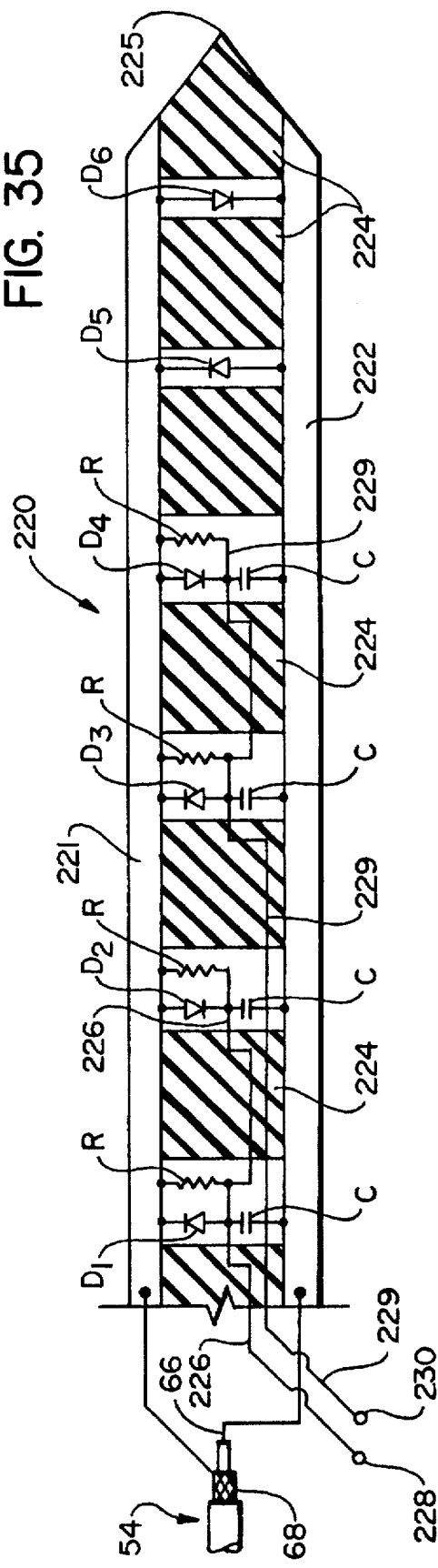
FIG. 35

APPARATUS AND METHODS FOR TIME DOMAIN REFLECTOMETRY

The present application is a division of applicant's U.S. application Ser. No. 08/071,748, filed Jun. 9, 1993, now U.S. Pat. No. 5,376,888, entitled "APPARATUS AND METHODS FOR GENERATING UNAMBIGUOUS LARGE AMPLITUDE TIMING MARKERS IN TIME DOMAIN REFLECTOMETRY SYSTEMS FOR MEASURING PROPAGATION VELOCITIES OF RF PULSES TO DETERMINE MATERIAL LIQUID CONTENTS, MOISTURE PROFILES IN SOIL AND SIMILAR TEST MATERIALS, MATERIAL LEVELS, AND MATERIAL DIELECTRIC CONSTANTS".

BACKGROUND OF THE INVENTION

1. Technical Field

The present invention relates generally to Time Domain Reflectometry Systems (hereinafter "TDR") used to measure the propagation velocity of RF pulses along transmission lines, or probes, inserted into material undergoing test for water or other liquid content, or to determine material levels in a container, or to determine material dielectric constants; and, more particularly, to improved transmission line probes and/or probe adapters employing at least one and, preferably two or more, remotely operated, active, normally open, variable impedance devices for establishing one or more unambiguous large amplitude timing markers that are readily discernable and measurable by both observation and manual techniques, as well as by automated electronic processing, measuring and display systems.

More specifically, and in one preferred embodiment, the present invention—an invention which finds particularly advantageous, but by no means exclusive, use in the fields of soil science, hydrology, agriculture, seedling nurseries and similar soil/moisture environments—relates to methods and apparatus including active, as contrasted with passive, variable impedance devices such, merely by way of example, as at least one, and preferably n pairs (where "n" is any desired whole integer) of PIN diodes interconnecting the parallel transmission lines defining a moisture sensitive probe at selected, known, spaced points $X_1, X_2 \ldots X_n$, along the probe. As a consequence of this arrangement, when any given variable impedance device or diode is biased to the conductive state, the resulting electrical short produces an electrical discontinuity which serves to transmit a large amplitude reflection to the TDR instrument establishing an unambiguous, large amplitude, readily discernable and measurable timing marker $T_n$; yet, when the variable impedance device or diode is biased to the nonconductive or open state, the electromagnetic pulses are propagated down the transmission line without change except for attenuation inherently resulting from the natural impedance characteristics of the transmission line.

Stated differently, the remotely operated, active, variable impedance devices mounted on the probe, when biased to conduction to establish a shorted electrical discontinuity in the transmission line, serve to greatly increase the amplitude, and therefore the detectability and measurability, of the $T_1, T_2 \ldots T_n$ reflections respectively produced at the $X_1, X_2 \ldots X_n$ specific points along the probe where the variable impedance devices are located.

The invention finds particularly advantageous use when employed with differential detection apparatus and methods, including waveform subtraction techniques, so as to provide a significant increase in the effective amplitude of the reflections of interest, as well as significant reduction and/or elimination of background noise resulting from, for example, mismatched and inexpensive electrical components and other spurious discontinuities, such, merely by way of example, as spurious reflections from layer interfaces in layered soil.

Probes employing variable impedance devices may be interrogated, and differential detection techniques may be employed using a conventional TDR instrument; or, in another of its important aspects, the invention permits use of synchronous detection techniques for processing signals at one or more precise timing markers $T_1, T_2 \ldots T_n$ where such signals are representative of probe reflections derived from shortable diodes, or similar shortable variable impedance devices, to provide remotely shortable diode ON/OFF modulation.

In another embodiment, this invention allows the optional processing of reflections in those instances where the probes do not have remotely shortable impedance device capability, or where the probes employ only a single remotely shortable impedance device. The present invention permits of time delay modulation by rapidly switching between two preset delay circuits so as to establish first and second preset time delays $T_A, T_B$ and to generate a square wave output signal from a Sample-And-Hold circuit whose amplitude is proportional to the slope of the reflection, which signal is then processed using synchronous detection techniques. Such an arrangement is particularly advantageous when dealing with relatively homogeneous soils of the type found in seedling nurseries where the natural reflection at the end of the transmission line/probe at time $T_2$ is typically large and free from distortion.

As the ensuing description proceeds, the invention will be described in connection with a TDR system for detecting and measuring soil water content and providing moisture profiles of the soil medium under test since the invention finds particularly advantageous application in this particular agricultural field and in the related fields of soil science and hydrology. However, those skilled in the art will appreciate as the ensuing description proceeds that the invention is not limited to measurement of soil water content and/or generating moisture profiles; but, rather, it will also find advantageous application in environments wherein the medium under test may comprise, for example, granular and/or particulate materials other than soil, sand or the like—for example, grain—and where the liquid whose volume content is of interest is other than water—for example, alcohol or the like. Moreover, it will be understood by those skilled in the art that the invention can also be used to determine levels of liquids or dry particulate solids in storage containers, or to determine the dielectric constant K of any solid material through which the probe extends. Therefore, it will be understood that terms such as "soil", "water" and "moisture" are used herein and in the appended claims in a non-limiting sense and for descriptive purposes only.

2. Background Art

Those skilled in the art will, of course, appreciate that TDR apparatus and methods have been widely used for many years in a wide range of different applications including, but not limited to, the measurement of soil water content and similar material liquid content. Such systems are based upon the principle that since the dielectric constant K of water is approximately 80—e.g., 78.9 at 23° C.—while the dielectric constants for various materials are known and considerably lower—for example, the dielectric constant for most dry soil solids ranges from about 2 to about 5—a measurement of the dielectric constant of a soil or other material sample provides an excellent measure of the soil's or other material's water content or other dielectric characteristic. And, since it is also known that the apparent dielectric constant $K_a$ of a moist soil sample or other moist material sample is directly related to the propagation velocity V of an electromagnetic wave as it transits an RF transmission line extending through the particular sample undergoing test, TDR systems have been designed to provide fast rise time electromagnetic pulses which are propagated along a transmission line of known length while measuring the times of arrival $T_1$, $T_2$ of reflections from electrical discontinuities in the transmission line at two known spaced points $X_1$, $X_2$—for example, where $X_1$ represents the air/material interface where the coaxial connecting cable is attached to the transmission line probe and $X_2$ represents the distal end of the transmission line probe, thereby enabling calculation of the propagation velocity V of the electromagnetic wave and, therefore, calculation of the apparent dielectric constant $K_a$ of the material undergoing test and through which the transmission line probe extends. Such calculated apparent dielectric constant $K_a$ may be of interest, or it may provide a direct indication of the test material's water (or other liquid) content.

The foregoing general principles of TDR systems are, as stated above, well known and have been described in considerable detail in the literature. Those interested in a comprehensive, but far from exhaustive, compilation of said literature references are referred to the following articles:

| | |
|---|---|
| Ref. No. 1 | Alharthi, A. and Lange, J., Soil Water Saturation: Dielectric Determination, WATER RESOURCES RESEARCH, Vol. 23, No. 4, pp. 591–595 (April, 1987). |
| Ref. No. 2 | Anon., Circuit Description, TEKTRONIX 1502 TDR INSTRUMENT OPERATORS AND MAINTENANCE MANUAL, Sect. 3, pp. 3-1–3-6 and PULSER/SAMPLER DRG. (rev.) (January, 1986). |
| Ref. No. 3 | Baker, J. M. and Allmaras, R. R., System for Automating and Multiplexing Soil Moisture Measurement by Time-Domain Reflectometry, SOIL SCIENCE SOCIETY OF AMERICA JOURNAL, Vol. 54, No. 1, pp. 1–6 (January-February, 1990). |
| Ref. No. 4 | Baker, J. M. and Lascano, R. J., The Spatial Sensitivity of Time-Domain Reflectometry, SOIL SCIENCE, Vol. 147, No. 5, pp. 378–384 (May, 1989). |
| Ref. No. 5 | Dalton, F. N., Herkelrath, W. N., Rawlins, D. S. and Rhoades, J. D., Time-Domain Reflectometry: Simultaneous Measurement of Soil Water Content and Electrical Conductivity with a Single Probe, SCIENCE, Vol. 224, pp. 989–990 (1984). |
| Ref. No. 6 | Dalton, F. N. and van Genuchten, M. Th., The Time-Domain Reflectometry Method For Measuring Soil Water Content And Salinity, GEODERMA, Vol. 38, pp. 237–250 (1986). |
| Ref. No. 7 | Dasberg, S. and Dalton, F. N., Time Domain Reflectometry Field Measurements of Soil Water Content and Electrical Conductivity, SOIL SCIENCE SOCIETY OF AMERICA, Vol. 49, pp. 293–297 (1985). |
| Ref. No. 8 | Dasberg, S. and Hopmans, J. W., Time Domain Reflectometry Calibration for Uniformly and Nonuniformly Wetted Sandy and Clayey Loam Soils, SOIL SCIENCE SOCIETY OF AMERICA JOURNAL, Vol. 56, pp. 1341–1345 (1992). |
| Ref. No. 9 | Fellner-Feldegg, H., The Measurement of Dielectrics in the Time Domain, THE JOURNAL OF PHYSICAL CHEMISTRY, Vol. 73, No. 3, pp. 616–623 (March, 1969). |
| Ref. No. 10 | Grove, W. M., Sampling for Oscilloscopes and Other RF Systems: Dc Through X-Band, ISEE, TRANSACTIONS ON MICROWAVE THEORY AND TECHNIQUES, Vol. MTT-14, No. 12 (December, 1966). |
| Ref. No. 11 | Heimovaara, T. J. and Bouten, W., A Computer-Controlled 36-Channel Time Domain Reflectometry System for Monitoring Soil Water Contents, WATER RESOURCES RESEARCH, Vol. 26, No. 10, pp. 2311–2316 (October, 1990). |
| Ref. No. 12 | Hook, W. R., Livingston, N. J., Sun, Z. J. and Hook, P. B., Remote Diode Shorting Improves Measurement of Soil Water by Time Domain Reflectometry, SOIL SCIENCE SOCIETY OF AMERICA JOURNAL, Vol. 56, pp. 1384–1391 (September-October, 1992). |
| Ref. No. 13 | Kachanoski, R. G., Pringle, E. and Ward, A., Field Measurement of Solute Travel Times Using Time Domain Reflectometry, SOIL SCIENCE SOCIETY OF AMERICA JOURNAL, Vol. 56, pp. 47–52 (1992). |
| Ref. No. 14 | Ledieu, J., de Ridder, P., de Clerck, P. and Dautrebande, S., A Method of Measuring Soil Moisture By Time-Domain Reflectometry, JOURNAL OF HYDROLOGY, Vol. 88, pp. 319–328 (1986). |
| Ref. No. 15 | Malicki, M. A. and Skierucha, W. M., A Manually Controlled TDR Soil Moisture Meter Operating With 300 ps Rise-Time Needle Pulse, PROCEEDINGS OF INTERNATIONAL CONFERENCE ON MEASUREMENT OF SOIL AND PLANT WATER STATUS, Vol. 1-Soils, pp. 103–109, Academic Press, Inc. (1987). |
| Ref. No. 16 | Nadler, A., Dasberg, S. and Lapid, I., Time Domain Reflectometry Measurements of Water Content and Electrical Conductivity of Layered Soil Columns, SOIL SCIENCE SOCIETY OF AMERICA JOURNAL, Vol. 55, pp. 938–943 (July-August, 1991). |
| Ref. No. 17 | Rhoades, J. D., Raats, P. A. C. and Prather, R. J., Effects of Liquid-phase Electrical Conductivity, Water Content, and Surface Conductivity on Bulk Soil Electrical Conductivity, SOIL SCIENCE SOCIETY OF AMERICA JOURNAL, Vol. 40, pp. 651–655 (1976). |
| Ref. No. 18 | Rhoades, J. D. and van Schilfgaarde, J., An Electrical Conductivity Probe for Determining Soil Salinity, SOIL SCIENCE SOCIETY OF AMERICA JOURNAL, Vol. 40, pp. 647–651 (1976). |
| Ref. No. 19 | Roth, K., Schulin, R., Flühler, H. and Attinger, W., Calibration of Time Domain Reflectometry for Water Content Measurement Using a Composite Dielectric Approach, WATER RESOURCES RESEARCH, Vol. 26, No. 10, pp. 2267–2273 (October, 1990). |
| Ref. No. 20 | Topp, G. C., The Application Of Time-Domain Reflectometry (TDR) To Soil Water Content Measurement, PROCEEDINGS OF INTERNATIONAL CONFERENCE ON MEASUREMENT OF SOIL AND PLANT WATER STATUS, Vol. 1-Soils, pp. 85–93, Academic Press, Inc. (1987). |
| Ref. No. 21 | Topp, G. C., Davis, J. L. and Annan, |

| | |
|---|---|
| | A. P., Electromagnetic Determination of Soil Water Content: Measurements in Coaxial Transmission Lines, WATER RESOURCES RESEARCH, Vol. 16, No. 3, pp. 574–582 (June, 1980). |
| Ref. No. 22 | Topp, G. C., Davis, J. L. and Annan, A. P., Electromagnetic Determination of Soil Water Content Using TDR:II. Evaluation of Installation and Configuration of Parallel Transmission Lines, SOIL SCIENCE SOCIETY OF AMERICA JOURNAL, Vol. 46, pp. 672–678 (1982). |
| Ref. No. 23 | Topp, G. C. and Davis, J. L., Time-Domain Reflectometry (TDR) And Its Application To Irrigation Scheduling, ADVANCES IN IRRIGATION, Vol. 3, pp. 107–127, Academic Press, Inc. (1985). |
| Ref. No. 24 | Topp, G. C. and Davis, J. L., Measurement of Soil Water Content using Time-domain Reflectrometry (TDR): A Field Evaluation, SOIL SCIENCE SOCIETY OF AMERICA JOURNAL, Vol. 49, pp. 19–24 (1985). |
| Ref. No. 25 | Topp, G. C., Yanuka, M., Zebchuk, W. D. and Zegelin, S., Determination of Electrical Conductivity Using Time Domain Reflectometry: Soil and Water Experiments in Coaxial Lines, WATER RESOURCES RESEARCH, Vol. 24, No. 7, pp. 945–952 (July, 1988). |
| Ref. No. 26 | Wraith, J. M. and Baker, J. M., High-Resolution Measurement of Root Water Uptake Using Automated Time-Domain Reflectometry, SOIL SCIENCE SOCIETY OF AMERICA JOURNAL, Vol. 55, pp. 928–932 (1991). |
| Ref. No. 27 | Yanuka, M., Topp, G. C., Zegelin, S. and Zebchuk, W. D., Multiple Reflection and Attenuation of Time Domain Reflectometry Pulses: Theoretical Considerations for Applications to Soil and Water, WATER RESOURCES RESEARCH, Vol. 24, No. 7, pp. 939–944 (July, 1988). |
| Ref. No. 28 | Zegelin, S. J., White, I. and Jenkins, D. R., Improved Field Probes for Soil Water Content and Electrical Conductivity Measurement Using Time Domain Reflectometry, WATER RESOURCES RESEARCH, Vol. 25, No. 11, pp. 2367–2376 (November, 1989). |
| Ref. No. 29 | Zimmerman, A., The State Of The Art In Sampling, TEKTRONIX SERVICE SCOPE No. 52, pp. 1–7 (October, 1968). |

While TDR systems have been known and used for decades in non-agricultural fields such, for example, as in the telecommunication field, their application to agricultural fields and for use in measurement of soil water content and/or moisture profiles began to be seriously explored in or about the late 1960s and the early 1970s. Malicki et al., Ref. No. 13. Prior to that time, the more widely used systems and/or equipment for measurement of soil water content included, merely by way of example: i) neutron modulation or scattering; ii) neutron probes; iii) gamma attenuation; iv) gravimetric and thermogravimetric systems; v) lysimetry; vi) tensiometers; and vii), gypsum blocks. These conventional techniques, and some of the disadvantages inherent in their use, have been described in the literature. Baker et al., Ref. No. 3; Dalton et al., Ref. No. 5; and, Topp et al., Ref. No. 23. However, despite their known disadvantages, such conventional systems have continued to be utilized in the field as design, development and experimental work with TDR systems have progressed.

Use of TDR systems to measure, for example, soil water content has many advantages over the known conventional systems described above such, merely by way of example, as:

i) excellent spatial resolution (Baker et al., Ref. No. 4);

ii) ability to measure close to the soil surface (Topp, Ref. No. 20; and, Zegelin et al., Ref. No. 28);

iii) excellent multiplexing capability (Baker et al., Ref. No. 3; and, Zegelin et al., Ref. No. 28);

iv) potential for accuracies greater than $2 \times 10^{-2}$ m$^3$/m$^3$ (Topp, Ref. No. 20; and, Topp, et al., Ref. No. 24);

v) potential for rapid reading in the field with only minimal soil disturbance (Baker et al., Ref. No. 4; Kachanoski et al., Ref. No. 13; and, Roth et al., Ref. No. 19); and, vi) measurements of volumetric water content appear to be substantially independent of soil type and salinity for many, if not most, soil environments (Dasberg et al., Ref. No. 7; Fellner-Feldegg, Ref. No. 9; and, Topp et al., Ref. Nos. 21, 23 and 24).

Considerable work in soil evaluation and various agricultural applications using Time Domain Reflectometry has been carried out in the past and has been widely reported. See, Ref. Nos. 3, 5–8, 13–16, and 19–26. In the course of that work some improved and excellent transmission line or probe geometries have been developed. Zegelin et al., Ref. No. 28 and International Publication No. WO89/12820 based on White et al. International Patent Application No. PCT/AU89/00266.

Measurement of the propagation velocity V of an electromagnetic wave in moist soil as it travels along a transmission line or probe is basic to the TDR soil water content method. Topp et al., Ref. No. 21. Thus, in a typical instance for measuring soil water content, a transmission line or probe having physical discontinuities present at two known locations $X_1$, $X_2$ along the line separated by a distance $X_2$ minus $X_1$ (where $X_2$ represents the end of the transmission line and $X_1$ represents, for example, the coaxial cable/transmission line interface) is imbedded in the soil. The time that a reflection from the discontinuity at point $X_1$ arrives back at the TDR instrument may be designated $T_1$, while the time that the reflection from the discontinuity at point $X_2$ arrives back at the TDR instrument may be designated $T_2$. Thus, the propagation velocity V is:

$$V = \frac{2(X_2 - X_1)}{T_2 - T_1} \qquad [1]$$

As described in Ledieu et al., Ref. No. 14, the propagation velocity V is usually normalized to the speed of light (c) in space using the apparent dielectric constant formula:

$$K_a = (c/V)^2; \qquad [2]$$

and, since (c) is a known quantity and the propagation velocity V is a measurable quantity, the apparent dielectric constant $K_a$ of the materials surrounding the probe can be calculated to provide, for example, a direct indication of the moisture content of the test material. This is possible because the apparent dielectric constant $K_a$ of moist soils changes substantially as water saturation rises since there is a large contrast in the dielectric constant K of water and that of most dry soil solids. Alharthi et al., Ref. No. 1.

However, one of the most significant problems heretofore encountered in TDR measurement systems resides in the fact that the actual values of $T_1$, $T_2$, $X_1$ and $X_2$ are extremely critical; and, even relatively small errors can result in significant errors in the calculation of the test material's apparent dielectric constant $K_a$. Where the TDR system is employed to determine material level in a container, liquid profiles, or the liquid content of the test material, an error in calculating the apparent dielectric constant $K_a$ will, of course, result in a significant error in the ultimate calculated result.

Minimal performance and design criteria for a basic probe to be used with TDR instruments include, for example:

i) fast rise times for $T_1$ and $T_2$ reflections;
  ii) amplitudes for $T_1$ and $T_2$ reflections which are at least 90% of the maximum available amplitude—i.e., the amplitude of the reflection from the unterminated end of the coaxial connector cable;
  iii) minimal electromagnetic pickup; and,
  iv) minimal cost.

Probes that employ only passive elements cannot meet the foregoing criteria. Excellent examples of such probes include, for example, those disclosed by Zegelin et al., Ref. No. 28 and International Publication No. WO89/12820 based upon White et al. International Patent Application No. PCT/AU89/00266.

It is known that the amplitude of the $T_1$ reflection can be increased by adding passive elements such as reactive components or impedance changes at or near $X_1$. Ledieu et al., Ref. No. 14; and, Malicki et al., Ref. No. 15. Ledieu et al., Ref. No. 14, employs, for example, two passive diodes in opposition which are soldered to the front ends of the two parallel probe transmission lines adjacent their interface with the coaxial cable. This approach has, however, proven to be highly limited because of the loss of energy at $X_1$ induced by the two (2) passive diodes which create the $T_1$ reflection and which serves to significantly reduce the amplitude of the $T_2$ reflection since the loss occurs twice—i.e., once as the electromagnetic wave is propagated down the coaxial cable/transmission line and a second time as the reflection from point $X_2$ passes back through the transmission line/coaxial cable to the TDR instrument. This problem is exacerbated by the use of long connecting cables—e.g., cables up to one hundred (100) meters in length or more-having reduced high frequency transmission characteristics. As a consequence, such TDR systems have limited cable lengths and require extremely expensive, high-performance TDR instruments and waveform processors in order to detect the weak $T_2$ reflection. However, even with an expensive high-performance system, the weak $T_2$ reflections can, and often do, generate false data.

The use of a strip line probe or transmission line—i.e., a generally one-piece, blade-like, integral probe defined by parallel conductive strips formed on a printed circuit board is described by Fellner-Feldegg, Ref. No. 9. The author suggests covering the two parallel conductive strips with dielectric material to reduce the characteristic impedance of the line.

Experimentation with TDR systems has revealed that the impedance mismatch between coaxial cables and 2-conductor probes introduces an error source into the measurements. It has, therefore, been proposed that a balun transformer be employed to compensate for that impedance mismatch. Dalton et al., Ref. Nos. 5 and 6; Dasberg et al., Ref. No. 8; Nadler et al., Ref. No. 16; Topp, Ref. No. 20; Topp et al., Ref. Nos. 23 and 24; and, Wraith et al., Ref. No. 26. However, the use of a balun transformer not only significantly increases the cost of the system but, moreover, balun transformers are, themselves, a source of error problems. Zegelin et al., Ref. No. 28.

When using 3 or 4-rod probes such as disclosed by Zegelin et al., Ref. No. 28 and in International Publication No. WO 89/12820 based upon White et al. International Patent Application No. PCT/AU89/00266—probes which present significant improvements over other conventional probes in that they are configured to minimize impedance mismatches between the probe and the interconnecting coaxial cable—it has been found that the $T_2$ reflections can be significantly reduced by physical and/or moisture layers within soil. Thus, reflections are reduced in amplitude by such layering discontinuities which serve to change the impedance characteristics of the transmission line; and, the intermediate reflections caused by the transmission line impedance change at such layered discontinuities become undesirable background noise. This background noise may not only cause false readings but, moreover, may merge with the true $T_2$ reflection to create significant delay errors. Nadler et al., Ref. No. 16. Indeed, for heavily layered soils, the $T_2$ reflection can become undetectable by any conventionally employed detection/measurement system.

Topp et al., Ref. No. 22, describes a multiple segment probe wherein the transmission line is designed to produce electrical discontinuities and consequent changed impedance characteristics at known locations along the line by, for example, varying the diameter of the solid brass rods used in the probe at selected points or by employing transmission lines formed of solid polystyrene having spaced areas coated with silver paint and joined by copper tape. However, the intermediate reflections from the electrical discontinuities are even smaller in amplitude than the small natural reflection from the transmission line end; and, consequently, the signal-to-noise ratio is even lower than the conventional $T_2$ reflection. Field use of this type of probe has not been widely reported in the literature.

Computer-controlled TDR systems have been described in the prior art for making large numbers of soil water content measurements at different sites at predetermined time intervals (Heimovaara et al., Ref. No. 11) and for use with layered soil media (Yanuka et al., Ref. No. 27). Automated and multiplexed TDR systems are described in, for example, Baker et al., Ref. No. 3. In other instances, soil water content has been measured with manually-controlled TDR systems. Malicki et al., Ref. No. 15.

Numerous prior art patents are also available relating to the use of TDR systems for a wide range of applications. For example, U.S. Pat. No. 3,771,056-Zimmerman discloses a display baseline stabilization circuit having a sampling system used to determine the size and location of any discontinuities in the characteristic impedance of the transmission line. The apparatus employs a switch to change the impedance characteristics at the end of the coaxial cable transmission line and thus provide one of several switchable, identifiable impedance changes at the probe terminus.

In U.S. Pat. No. 3,789,296-Caruso, Jr. et al., the patentees describe an apparatus for sensing the moisture content and, therefore, the amount of dielectric coating applied to a web-like carrier as the latter is passed between the sensing bars of a TDR system.

In Wrench, Jr. et al. U.S. Pat. No. 4,109,117, the patentees describe a TDR system in combination with a multiplexing technique for allowing the separation of signals from many transducers on a single coaxial cable passing through multiple sites. In this arrangement it is proposed to use variable impedances equally spaced along a transmission line wherein the variable impedances are in the form of field effect transistors (FETs) or microphones which produce discontinuities in the cable resulting in reflections that are sensed by the TDR system. Wrench, Jr. et al. are not, however, concerned with the measurement of propagation velocity.

In U.S. Pat. No. 4,786,857-Mohr et al., the patentees disclose the use of a TDR system having a coaxial transmission line with a passive terminating resistor to provide an identifiable impedance change at the probe terminus in a fashion somewhat similar to that disclosed in Zimmerman U.S. Pat. No. 3,771,056. The Mohr et al. apparatus is used to determine the relative proportions of intermixed constituents in a multi-phase fluid system.

Malicki et al. U.S. Pat. No. 4,918,375 is of interest for its disclosure of a TDR system for the measurement of soil water content using a Tektronix Model 1502 TDR acquired from Tektronix Corp., Beaverton, Oreg. In this system the patentees employ step-wise, local, specific, passive impedance discontinuities above the air/soil interface to establish a reference time for multiple parallel transmission lines.

Numerous other patent disclosures are of miscellaneous interest in that they disclose other types of systems, bearing certain similarities to TDR systems, for various applications. For example, in U.S. Pat. Nos. 3,853,005-Schendel and 3,995,212-Ross, the patentees insert transmission lines into a liquid container and use the reflection from the air/liquid interface to determine the level of liquid. A somewhat similar arrangement is disclosed in U.S. Pat. No. 4,135,397-Krake wherein the transmission line is inserted into a grain elevator with the transmission line having a passive load impedance $Z_1$ equal to the characteristic line impedance for terminating the transmission line. Again, the reflected pulse from the air/grain interface is indicative of the level of grain.

Wann U.S. Pat. No. 4,949,076 discloses a leak detector employing a coaxial cable used to detect reflected signals from a leak location with the coaxial cable employing a passive terminating resistor.

A somewhat different system is disclosed in Statutory Invention Registration No. H395-Nash wherein the registrant uses a coaxial cable to generate an electrical field at the end of the cable which is attenuated by the electrical characteristics of the material undergoing test; and, the attenuation in the reflected wave is then observed.

Other patents of miscellaneous interest include: i) U.S. Pat. No. 4,013,950-Falls [a probe for measuring electromagnetic impedance characteristics of soils]; ii) U.S. Pat. Nos. 4,281,285-Bastida and 4,341,112-Mackay et al. [the use of RF radiation to provide an indication of soil water content]; iii) U.S. Pat. No. 4,754,214-Bramanti et al. [a system for determining the amount of coal in furnace ash using a reflected microwave signal]; and iv), U.S. Pat. No. 4,807,471-Cournane et al. [a swept frequency system wherein the transmission line conductors are terminated by a passive variable impedance device such as a PIN diode for level measurement in storage silos].

Other prior art patents of general interest which do not relate to either TDR systems and/or to systems for measuring soil water content can be found in the art relating to transmission lines as used in various electronic devices. These include, merely by way of example, Oberbury U.S. Pat. No. 3,757,222 which discloses an RF system, and particularly, a single sideband generator employing diodes which are connected to ground along the length of the transmission line for defining switchable short circuits to advance or retard the phase of the signal at the load in digital steps. Similarly, Bakken U.S. Pat. No. 3,829,796 discloses an electronic amplitude modulator for use in navigational systems using diodes positioned along the transmission line to provide step-wise variation of the phase angle $\phi$ and, thereby, of the amplitude of the signal voltage.

U.S. Pat. No. 4,349,795-Kwok discloses an amplifier station for the trunk system in cable TV systems wherein a switching apparatus passes RF signals in a prescribed frequency band on a main transmission line to first and second transmission lines. PIN diodes short opposite ends of the first coaxial transmission line for improving isolation of the station equipment.

UK published Patent Application, Publication No. 2 216 355 A-Gale (1989) discloses a voltage-controlled oscillator using PIN diodes soldered to a microstrip transmission line to provide distributed capacitance.

A wide range of other devices have been used to short transmission lines for a wide range of purposes. These include, merely by way of example: i) U.S. Pat. No. 3,551,677-Brewster [a field reversal type pulse generator with a shorting switch formed by a plurality of parallel gas dielectric spark gaps connected across one end of the transmission line-the spark gaps are subjected to ultraviolet light to enable them to break down so as to permit the transmission line to discharge and cause the pulse generator to produce an output pulse]; ii) U.S. Pat. No. 3,993,933-Menninga [an electric overvoltage gas arrester with a metallic shorting mechanism to prevent overheating of a surge voltage gas tube used to protect equipment connected to telephone and other transmission lines]; iii) U.S. Pat. No. 4,755,769-Katz [a composite power amplifier wherein the output of a plurality of amplifiers are combined to produce a higher output signal-shorting switches are coupled to the transmission line and are selectively rendered conductive to adjust impedance and maintain impedance matching]; iv) U.S. Pat. No. 4,782,313-Brant, Jr. [a transmission line shorting switch for preventing transmission of signals along unbalanced transmission lines]; and v), UK Pat. No. 1444540-Heading [an electrical filter which uses a conductive track and wiper assembly on a transmission line to adjust bandwidth].

Notwithstanding the extensive reported work to date relating to TDR in general and specific TDR applications in respect of soil water content measurement, both in the literature and in patents, it has been found that the successful implementation of a TDR soil water content measurement system comprising a commercially acceptable system useful in the field has continued to suffer from numerous practical and/or cost-related limitations such, merely by way of example, as:

i) the complexity and high cost of conventional TDR instrumentation and, particularly, high-performance TDR instruments;

ii) the difficulties in detecting and accurately measuring relatively weak reflections of interest and/or distinguishing such reflections of interest from background noise;

iii) poor signal-to-noise ratios inherent in most conventional TDR systems;

iv) the unreliability of soil water content measurements in layered and/or highly saline soil;

v) signal attenuation inherent in transmission lines, thus precluding the usage of long cables and thereby limiting site coverage or requiring multiple TDR systems for relatively large sites; and, vi) the inability to reliably measure moisture profiles using a single vertical probe.

SUMMARY OF THE INVENTION

The foregoing practical and/or cost-related limitations and disadvantages inherent in reported prior art TDR methods and apparatus have been overcome by the present invention which provides for incorporation of active, as contrasted with passive, remotely operated variable impedance devices such, merely by way of example, as at least one, and preferably n pair(s) (where "n" is any desired whole integer) of shorting diodes interconnecting the parallel transmission line conductors at selected, known, spaced points $X_1, X_2 \ldots X_n$ along the effective length of the probe. As a consequence of this arrangement, the reflections generated at each discontinuity produced by activating the variable impedance devices—e.g., by biasing a given diode $D_n$ to conduction to short the transmission lines at a known pre-selected point $X_n$—are characterized by their relatively large amplitudes and their unambiguous signals. In short, these objectives are achieved without having to increase the amplitude of transmitted pulses, but, rather, by employment of probes having remotely operated active elements capable of establishing precise timing markers $T_1, T_2 \ldots T_n$ of readily discernable amplitude and polarity.

More specifically, the present invention employs remotely operated, active, variable impedance devices mounted on the probe or probe adapter to greatly increase the amplitude of, and therefore the detectability and measurability of, the $T_1$, $T_2 \ldots T_n$ reflections. Thus, when using remotely operated, active, variable impedance devices such as remotely operated switches or shorting diodes, when any given variable impedance device is rendered conductive to short the transmission line, a strong negative reflection $T_n$ is reflected from point $X_n$; but, when the impedance device is remotely biased to a non-conductive state, the circuitry permits propagation of the electromagnetic pulses down the transmission line past point $X_n$ without change except for attenuation inherently resulting from the natural impedance characteristics of the transmission line.

The probes can be configured so that the remotely operable variable impedance devices accurately define the air/ soil or other air/material interface, or both the interface and the probe end, or any other spaced selected points $X_1, X_2$ . . $X_n$ along the probe. When two (2) diodes or other variable impedance devices are employed, they are installed with opposite polarities. Consequently, when the bias insertion network produces a positive voltage output, the diode $D_1$ at, for example, point $X_1$, is rendered conductive to short the transmission line at $X_1$; when the bias insertion network produces a negative voltage output, the diode $D_2$ at point $X_2$ is rendered conductive to short the transmission line at point $X_2$; and, when the bias insertion network produces a zero volt (0v) output, both diodes $D_1$ and $D_2$ remain open and permit the transit of transmitted pulses and reflections as if no discontinuity was present.

When more than one pair of diodes or other variable impedance devices are employed, the probe is configured as a multi-segment probe having a diode located at each segment boundary. Such an arrangement requires that the diodes be AC coupled to the transmission line with a separate control wire for the second pair and each additional pair of diode locations—i.e., for diode pairs $D_1/D_4 \ldots D_{n-3}/D_{n-2}$.

The invention permits the probe to be configured as an averaging probe by connecting a plurality of discrete moisture sensitive transmission lines in series using intervening interconnecting cables; and, placing diodes $D_1$ and $D_2$ at the start and end of the series-connected transmission lines.

In another of its important aspects, the invention permits of use of synchronous detection techniques for processing signals at first and second precise Timing Markers $T_1, T_2$ where such signals are representative of probe reflections derived from either of: i) shortable diodes, or similar shortable variable impedance devices, to provide remotely shortable diode ON/OFF modulation; or ii), a variable time delay mechanism having the capability of being rapidly switched between two preset time delay circuits so as to establish unambiguous reflections at first and second time delays $T_A$, $T_B$ to generate a square wave having an amplitude proportional to the slope of the reflection—i.e., time delay modulation.

Stated in other words, it is a general aim of the present invention to provide improved TDR methods and apparatus for generating relatively high amplitude, unambiguous, timing markers $T_1, T_2 \ldots T_n$ characterized by their accuracy, reliability and magnitude and, therefore, by their observability and measurability; yet, which are highly cost effective and can be provided for but a fraction of the cost of conventional TDR systems.

More specifically, it is an important objective of the present invention to provide improved probes and/or adaptors for conventional prior art probes characterized by the employment of at least one (1) remotely operated, active, variable impedance device—and, preferably, one (1) or more pairs of remotely operated, active, variable impedance devices—which can be selectively and/or sequentially rendered conductive to establish a momentary short in the transmission line, thus producing an electrical discontinuity for generating a relatively large amplitude reflection $T_n$ serving as a reliable, observable and measurable timing marker.

In this connection, it is an object of the invention to provide probes and/or probe adaptors for use in TDR systems wherein the transmission line probe and/or adaptor is provided with remotely operable, active, variable impedance devices for establishing precise timing markers and which can readily be employed with differential detection apparatus and methods to provide maximum amplitude reflections at precise, pre-established and known spaced points $X_1, X_2$ $\ldots X_n$ and at accurately measured times $T_1, T_2 \ldots T_n$.

In another of its important objectives, the invention readily permits of the use of waveform subtraction techniques which make the system more tolerant to, for example, spurious reflections often found with mismatched and inexpensive components, thereby allowing the system to be designed using less complex and, therefore, less expensive TDR instruments. Moreover, waveform subtraction techniques are also useful for reducing background noise attributable to, for example, unwanted reflections from layered soils and similar discontinuity reflections that are not of interest.

It is a related object of the invention to provide a TDR system which, because of the significantly larger $T_n$ reflections, allows the use of less expensive cable and multiplexers; and, which also permits use of longer cables and, therefore, greater site coverage, all resulting in a significant reduction in overall system cost.

A more detailed object of the present invention is the provision of a TDR system characterized by its ability to reliably detect n reflections at n pre-established, precise and known timing markers defined by n remotely operable, active, shorting diodes (where "n" is any desired whole integer).

It is an object of the invention to provide a TDR system characterized by significant improvement in signal-to-noise ratio. To achieve this objective, the present invention employs remotely operable, active, variable impedance devices—e.g., diodes—to establish precise timing markers and which can be used in combination with differential detection techniques resulting in: i) increase of the effective amplitude of signal reflections of interest; ii) significant reduction in background noise; and iii), significant improvement in signal-to-noise ratio. One example of a differential detection technique is waveform subtraction, a technique which permits elimination of substantially all background noise.

As a result of achieving the foregoing objectives it is possible to make accurate measurements of volumetric water content in either saline or layered soils. It is further possible to make accurate reliable measurements of soil water content and/or other material liquid content using relatively long coaxial interconnection cables having lengths up to on the order of at least one hundred (100) meters; and, to accurately detect the times of arrival of reflection signals of interest even where the reflection signal is attenuated by a factor up to on the order of 2500:1. Rapid and reliable measurement of soil water and/or other material liquid contents are achieved over a wide range of operating conditions using either manual or automated processes, readout techniques and equipment. Additionally, it is possible to make accurate and reliable measurements of material levels in containers, as well as determination of the dielectric constant K of a wide range of materials undergoing test including soils, grains, particulate materials, solid materials, and the like. Moreover, a plurality of transmission line probes can be used through multiplexing techniques wherein a coaxial switch arrangement is interposed between the individual probes and the bias insertion network used for selectively rendering switchable variable impedance devices in the probes conductive or non-conductive.

DESCRIPTION OF THE DRAWINGS

These and other objects and advantages of the present invention will become more readily apparent upon reading the following Detailed Description and upon reference to the attached drawings, in which:

FIG. 7 is a diagrammatic block-and-line schematic drawing of a first probe embodying features of the present invention here illustrating a two-prong, two diode probe coupled to a suitable RF cable;

FIG. 8 is a drawing similar to that shown in FIG. 7, but here depicting a second probe embodying features of the invention employing three spaced parallel probe conductors and three remotely operable shorting diodes;

FIG. 9 is a drawing similar to that shown in FIG. 7, but depicting a third probe embodying features of the present invention, here employing two spaced parallel probe conductors, but only a single remotely operable shorting diode;

FIG. 10 is a drawing similar to that shown in FIG. 8, here depicting a fourth probe embodying features of the present invention with the probe including three spaced parallel probe conductors, but only a single remotely operable shorting diode;

FIG. 11 is a drawing similar to FIGS. 7 through 10, but here illustrating a fifth embodiment of the invention, partly in section, comprising an elongate, unitary, generally imperforate, bayonet-type probe employing: i) two spaced elongate plate-like conductors; ii) a central integral spacer formed of dielectric or other suitable non-conductive material; and iii), a pair of spaced remotely operable shorting diodes for establishing first and second timing markers;

FIG. 12 is a sectional view of the probe of FIG. 11, here taken substantially along the line 12—12 in FIG. 11;

FIG. 13 is a fragmentary, enlarged, plan view in highly detailed schematic form here illustrating one arrangement for bonding two spaced stainless steel conductors and an intermediate cast epoxy dielectric spacer together to form an integral unitary or one piece bayonet-like probe having a pair of spaced, remotely operable, shorting diodes electrically connected to the stainless steel conductors adjacent the opposite ends thereof;

FIGS. 14 and 15 are sectional views taken substantially along respective ones of the lines 14—14 and 15—15 in FIG. 13, here illustrating details of the structure employed to insure that the stainless steel conductors and epoxy spacer are securely bonded together in a rigid, stable structure;

FIGS. 16 and 17 are sectional views respectively taken substantially along the lines 16—16 and 17—17 in FIG. 13, and here depicting the electrical connections for the two remotely operable shorting diodes;

FIG. 18 is a fragmentary plan view similar to a portion of FIG. 13, but here depicting an alternative arrangement for bonding two spaced stainless steel conductors together using a cast resinous epoxy dielectric material;

FIG. 28 is a fragmentary plan view, partly in section, here depicting a spade-like fitting adapted to be slidably mounted on, and engaged with, the spaced conductors of a conventional two-pronged prior art probe of the type shown in FIGS. 1 and 19, such fitting including: i) two spaced parallel conductors; ii) a central integral spacer formed of dielectric or other suitable non-conductive material; and iii), a remotely operable shorting diode embedded in the dielectric material for selectively shorting one probe conductor to the other;

FIG. 29 is a sectional view of the assembled probe and spade-like fitting shown in FIG. 28, here taken substantially along the line 29—29 of FIG. 28;

FIG. 30 is a fragmentary schematic drawing depicting a remotely operable shorting diode probe suitable for use as an averaging probe in seedling nurseries or the like;

FIGS. 33 and 34 are plots illustrating waveform differentiation performed using the synchronous detector circuit shown in FIG. 31;

FIG. 35 is a diagrammatic, schematic, fragmentary block-and-line drawing, partly in section, depicting an elongate, solid, impervious and integral two-conductor bayonet-type probe embodying features of the present invention, but here illustrating the probe with multiple pairs of remotely operable shorting diodes which together define a multiple segment bayonet-type probe; and, FIGS. 36A and 36B, when placed in side-by-side relation and viewed conjointly, comprise a highly diagrammatic, schematic, block-and-line drawing, somewhat similar to FIG. 4, but here illustrating an exemplary electrical circuit used for coupling the multiple segment bayonet-type probe of FIG. 35 to the modified form of Time Domain Reflectometer electronics shown in FIG. 31.

Figures 1, 2, 3:
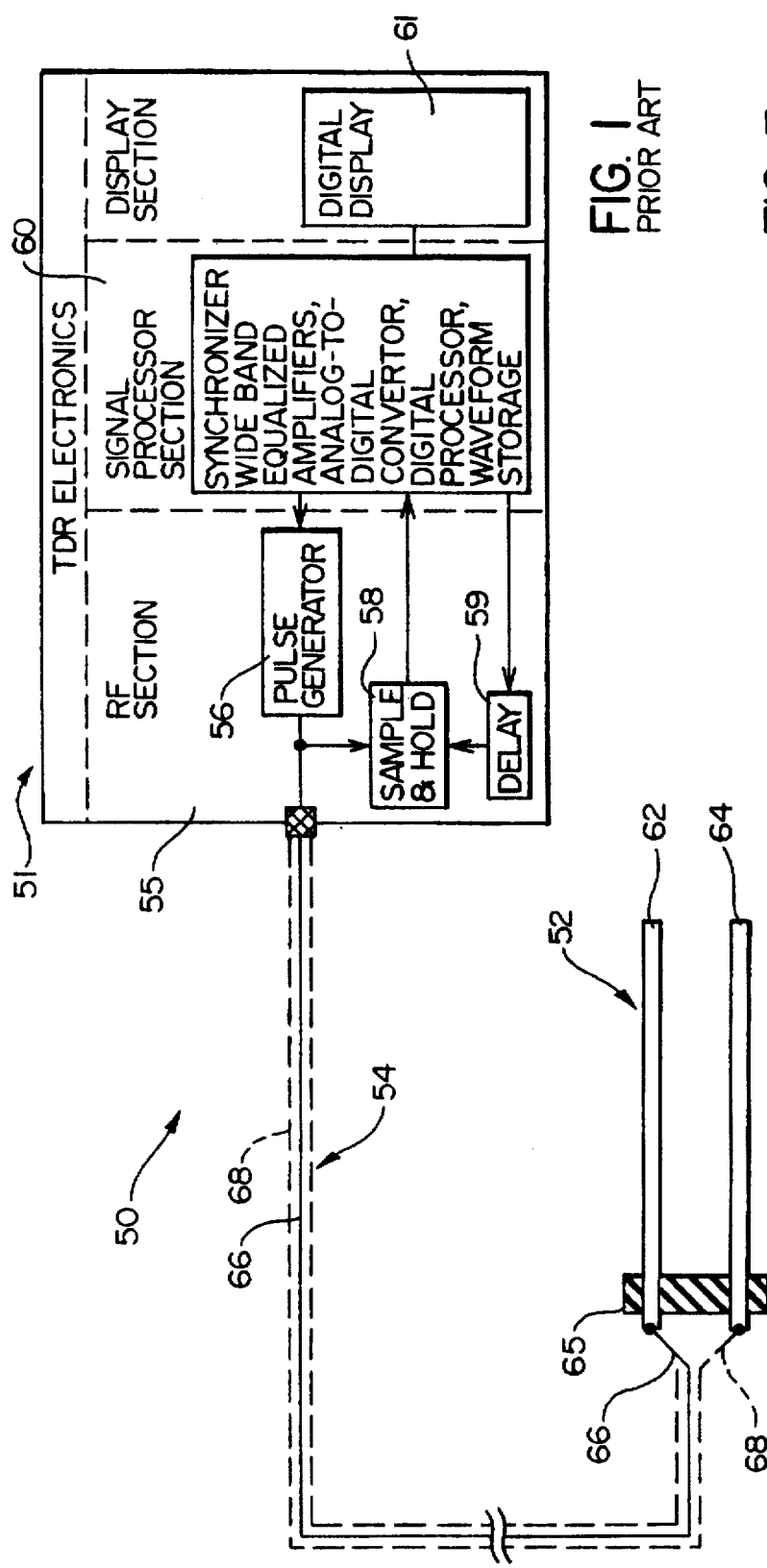
FIG. 1 is a highly diagrammatic, schematic, fragmentary, block-and-line drawing, partly in section, here illustrating a typical prior art system for measurement of moisture content in test materials such, merely by way of example, as soil environments, and here incorporating a conventional, commercially available, off-the-shelf Time Domain Reflectometer and a conventional probe employing two spaced, parallel, rod-like conductors for insertion into the test material.
FIG. 2 is a highly diagrammatic, fragmentary, schematic drawing, partly in section, here depicting a modified form of conventional prior art probe employing three spaced parallel conductors for insertion into a test material, such modified probe also being suitable for use with the overall test system depicted in FIG. 1.
FIG. 3 is a plot of voltage versus time and depicts a representative reflection waveform of the type generated using the conventional prior art measurement system shown in FIG. 1 with a conventional probe of the type shown in either FIG. 1 or FIG. 2.

While the invention is susceptible of various modifications and alternative forms, specific embodiments thereof have been shown by way of example in the drawings and will herein be described in detail. It should be understood, however, that it is not intended to limit the invention to the particular forms disclosed; but, on the contrary, the intention is to cover all modifications, equivalents and/or alternatives falling within the spirit and scope of the invention as expressed in the appended claims.

DETAILED DESCRIPTION

Turning now to the drawings, and directing attention first to FIGS. 1 through 3, a conventional prior art TDR system.

generally indicated at 50, has been illustrated in highly diagrammatic block-and-line form in FIG. 1. As here shown, the basic components of the TDR system 50 depicted in FIG. 1 include: i) a conventional TDR unit, generally indicated at 51; ii) a moisture sensitive probe, generally indicated at 52, adapted to be inserted into the soil or other medium to be tested (not shown); and iii), a coaxial cable, generally indicated at 54, for coupling the probe 52 to the TDR unit 51.

The conventional TDR unit 51 here shown in diagrammatic form comprises an off-the-shelf Model 1502B TDR instrument available from Tektronix Corp., Beaverton, Oreg. As those skilled in the art will appreciate, such a conventional TDR unit employs: i) an RF section 55 including a Pulse Generator 56 for generating fast rise time pulses on the order of approximately 200 picoseconds, a Sample-And-Hold circuit 58 for sampling reflected signals, and a Delay unit 59; ii) a Signal Processor Section 60; and iii), a Digital Display 61. The conventional probe 52 comprises a 2-conductor probe including a pair of parallel conductors 62, 64 which are preferably formed of stainless steel rods having diameters on the order of 0.125" mounted at one end in a dielectric support member or base 65. Coaxial cable 54 includes: i) a central conductor 66 which is coupled at one end to the Pulse Generator/Sample-And-Hold circuits 56/58 and at its other end to one of the pair of probe conductors— here, conductor 62—and ii), a surrounding coaxial cable shield 68 coupled both to the second probe conductor 64 and to ground.

Referring to FIG. 2, a slightly modified, but completely conventional, 3—conductor probe 69 of the type developed and described by Zegelin et al., Ref. No. 28, and in International Publication No. WO89/12820 based upon White et al. International Patent Application No. PCT/AU89/00266, has been depicted. As here shown, probe 69 includes a central, rod-like, stainless steel conductor 70 and a pair of spaced, outer, parallel, rod-like stainless steel conductors 71, 72. In this arrangement, the central conductor 66 of the coaxial cable 54 is coupled to the probe's central stainless steel conductor 70, while the coaxial cable shield 68 is coupled to the outer stainless steel conductors 71, 72. Thus, the arrangement of probe conductors 70, 71, 72 tends to emulate the construction of a typical coaxial cable, thereby minimizing impedance mismatches between the coaxial cable 54 and the probe 69 at the cable/probe interface 54/69.

In operation, the conventional TDR unit 51 depicted in FIG. 1 generates a series of relatively fast rise time—e.g., approximately 200 picoseconds—step pulses which are propagated down the coaxial cable 54 and along the transmission line defined by the probe conductors 62, 64 (FIG. 1) or the probe conductors 70, 71, 72 (FIG. 2) which have been inserted into a soil or other medium (not shown) undergoing test. As each pulse wavefront reaches the distal ends of the probe conductors 62, 64 (FIG. 1) or 70, 71, 72 (FIG. 2), it is reflected off the end of the transmission line with the reflected signals traveling back up the transmission line probe/coaxial cable 62, 64/54 or 70–72/54 to the TDR Sample-And-Hold circuit 58. The TDR unit 51 then measures the shape of the reflection waveform 75, thereby permitting a determination of the time of arrival $T_n$ of each reflection of interest.

A typical and completely conventional reflection waveform has been illustrated at 75 in FIG. 3. Those skilled in the art will appreciate that the reflection waveform 75 is defined by a series of reflections including not only the reflections from the distal ends of the probe conductors which arrive at the TDR unit 51 at time $T_2$ and the reflections from the air/soil interface which arrive at the TDR unit 51 at time $T_1$, but, additionally, numerous other reflections such as a reflection from the coaxial cable/probe interface 54/52 (69)—a reflection which may be coincident with, or very close in time to, the reflection from the air/soil interface which arrives at time $T_1$, as well as numerous other spurious reflections intermediate times $T_1$ and $T_2$ generated by electrical discontinuities along the length of the probe which are attributable to, for example, layer interfaces in layered soil and/or other dielectric discontinuities all contributing to undesirable background noise. In addition, the presence of salt in the soil—a condition termed "saline soil"—will attenuate the desired reflections from the distal ends of the probe conductors which arrive at the TDR unit 51 at time $T_2$—i.e., the presence of salt in the soil reduces the amplitude of the natural reflections, making them more difficult to distinguish from background noise.

The problems attributable to usage of conventional TDR systems of the type hereinabove described are directly related to the accuracy and reliability of the data measured representing the time of arrival of the two specific reflections of interest—i.e., the reflection from the air/soil interface arriving at time $T_1$ and the reflection from the ends of the probe conductors arriving at time $T_2$—and accurately distinguishing those two reflections of interest from the clutter of reflected signals of no interest. Thus, in FIG. 3, the times of interest—i.e., times $T_1$ and $T_2$—when the two reflections of interest are received at the TDR unit 51 represent, at best, loose approximations based upon the observed shape of the waveform 75 and the operator's judgment as to which two (2) points along the waveform are, in fact, the two reflections of interest which define the specific times of arrival $T_1$, $T_2$ of interest—viz., reflections from the air/soil interface and the probe's distal end. Of course, if the operator happens to select one or two points along the waveform 75 defined by one or two spurious reflections rather than the true reflection(s) of interest, then the particular time(s) of arrival $T_n$ of the selected spurious reflection(s) which is(are) determined will introduce error into the calculation of the propagation velocity V of the electromagnetic pulses.

In short, any determination of the two points along the probe where the two (2) reflections of interest are generated and the times of arrival $T_1$, $T_2$ of those reflections can, in the absence of very sophisticated software and its attendant significantly increased cost, make computation of the propagation velocity V in conventional TDR systems of the type illustrated in FIGS. 1 through 3 highly questionable and prone to significant error. Since the propagation velocity V of the wavefronts forming the fast rise time step pulses is dependent upon the precise locations $X_1$, $X_2$ of the two points where the reflections of interest occur and the exact times of arrival $T_1$, $T_2$ of those reflections back at the TDR unit 51—See, equation [1], supra—such computations represent, at best, crude approximations of the propagation velocity V and, therefore, of the apparent dielectric constant $K_a$ of the medium being tested. Unfortunately, however, significant errors have been, and continue to be, generated because of the lack of precision and accuracy in distinguishing the reflections of interest from spurious reflections comprising background noise and in determining precisely where such reflections of interest were generated and what the times of arrival of the reflected signals at the TDR instrument are.

Figure 4:
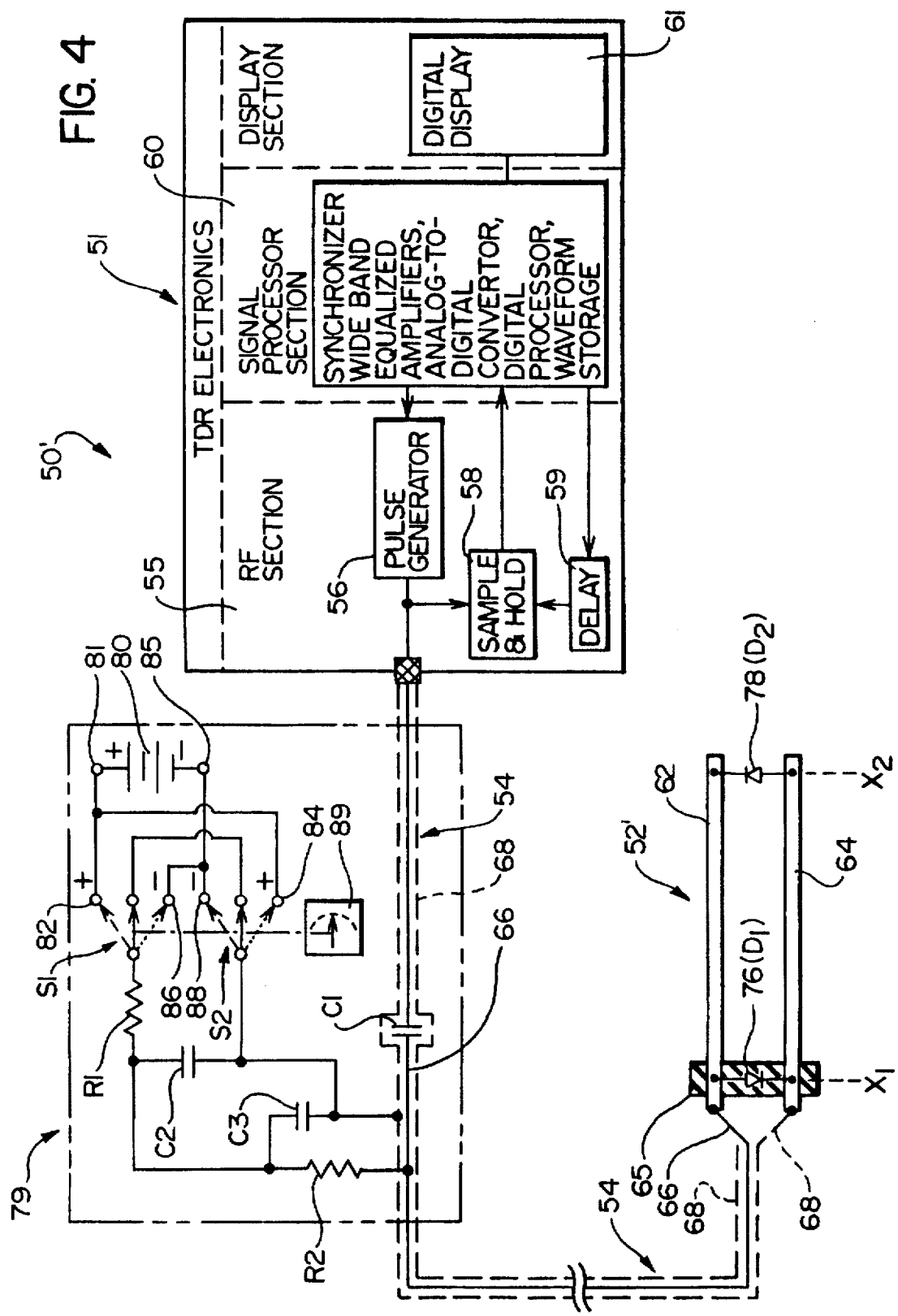
FIG. 4 is a highly diagrammatic, schematic, fragmentary, block-and-line drawing, partly in section, which is similar to the prior art system shown in FIG. 1, again employing a conventional, commercially available, off-the-shelf Time Domain Reflectometer coupled to a two-pronged probe by means of a suitable RF cable which here takes the form of a conventional coaxial cable, but here illustrating an overall system including features embodying the present invention in that: i) the probe is provided with a pair of remotely operable, normally open or non-conductive, variable impedance devices—e.g., diodes—for selectively establishing timing markers; and ii), the circuitry depicted includes a suitable bias insertion network for permitting remote control of the variable impedance devices.

In accordance with one of the important aspects of the present invention, provision is made for modifying the conventional TDR system 50 depicted in FIG. 1 so as to insure generation of waveform reflections at times $T_1$, $T_2$ . . . $T_n$ which: i) are unambiguous; ii) are of readily observable and measurable amplitude and polarity; iii) are immediately distinguishable from other background reflections of no interest; iv) occur at fixed, known and precise pre-established points $X_1, X_2 \ldots X_n$ along the length of the probe; and v), generate significant and instantly observable reflections at precise timing markers $T_1, T_2 \ldots T_n$. To accomplish this, and as best illustrated in FIG. 4, a conventional Model 1502B TDR, generally indicated at 51, identical to that shown in FIG. 1, is coupled to a probe 52' embodying features of the present invention and having a pair of spaced parallel conductors 62, 64 by means of a coaxial cable 54 identical to that depicted in FIG. 1 which is coupled at one end to the probe 52' and at the other end to the TDR unit 51 in precisely the same manner as previously described. In this instance, however, the probe 52' is provided with a pair of oppositely directed, remotely operable, normally open, variable impedance devices 76, 78 electrically coupled across the probe conductors 62, 64 at two fixed, known and precise pre-selected points $X_1, X_2$. Since those two points $X_1, X_2$ are predetermined and known with exactitude, the distance that a propagated pulse and a reflection thereof will travel—viz., $2(X_2-X_1)$—is a precise and accurate quantity in all subsequent determinations of the propagation velocity V of electromagnetic pulses for that particular transmission line probe; and, the only remaining variables to be determined are $T_1, T_2$. In the exemplary form of the invention here shown, the remotely operable variable impedance devices 76, 78 respectively comprise oppositely directed PIN diodes $D_1, D_2$.

In order to selectively render one, and only one, of the variable impedance devices 76, 78—e.g., the PIN diodes $D_1$, $D_2$—conductive so as to selectively establish an electrical short across the probe conductors 62, 64 at either point $X_1$ or point $X_2$, thereby generating unambiguous reflections serving to establish accurate and precise timing markers $T_1$, $T_2$ for reflections from those two accurately known points, the TDR system 50' depicted in FIG. 4 further includes a suitable bias insertion network, generally indicated at 79, interposed in the coaxial cable 54 for selectively forward biasing the variable impedance devices 76, 78 to conduction. To this end, the exemplary bias insertion network 79 includes a voltage source diagrammatically illustrated as a battery 80 having its positive terminal 81 coupled to the positive input terminals 82, 84 of a pair of remotely operable, ganged, parallel switches S1, S2 and its negative terminal 85 coupled to the negative input terminals 86, 88 of the switches S1, S2. Switches S1, S2 may be manually operated using any suitable switch controller 89; or, alternatively, they may be electronically controlled by signals (not shown) output from the TDR unit 51; or, if desired, both the switches S1, S2 and the TDR unit 51 may be automatically and remotely controlled from any suitable computer (not shown).

In any event, when the switches S1, S2 are in the solid line positions depicted in FIG. 4, the variable impedance devices 76, 78—e.g., diodes $D_1, D_2$—are electrically isolated from the bias voltage provided by the battery 80 or other voltage source; and, consequently, both variable impedance devices 76, 78—e.g., diodes $D_1, D_2$—remain open or non-conductive. Consequently, electromagnetic pulses propagated down the coaxial cable 54 and over the transmission line probe 52' remain essentially unaffected by the presence of such devices.

If, on the other hand, the switches S1, S2 are shifted by actuation of the switch controller 89 to the dashed line positions depicted in FIG. 4, the positive terminal 81 of the voltage source 80 is directly coupled via series resistors R1, R2 to the central conductor 66 of the coaxial cable 54 and thence to probe conductor 62, while the negative terminal 85 of the voltage source 80 is coupled directly to the coaxial cable shield 68 and thence to probe conductor 64. This serves to forward bias variable impedance device 76 (diode $D_1$) into conduction, creating a momentary short circuit across the probe conductors 62, 64 at point $X_1$.

Finally, if the switches S1, S2 are shifted by action of the switch controller 89 to the dotted line positions shown in FIG. 4, the positive terminal 81 of the voltage source 80 is coupled directly to the coaxial cable shield 68 and thence to probe conductor 64, while the negative terminal 85 of the voltage source is coupled via series resistors R1, R2 to the central conductor 66 of the coaxial cable 54 and thence to probe conductor 62, thus forward biasing variable impedance device 78—e.g., diode DE-to conduction and shorting the probe conductors 62, 64 at point $X_2$.

In order to protect the TDR unit from damage due to switching transients and DC voltages, a transient filter is provided in the bias insertion network 79 by resistor R1 (a 47 ohm resistor in the exemplary circuit), resistor R2 (220 ohms), capacitor C1 (0.047 microfarads) providing a DC block, capacitor C2 (1.0 microfarads), and by-pass capacitor C3 (0.01 microfarads). The use of the bias insertion resistor R2 and the by-pass capacitor C3, together with short lead lengths, insures achievement of the desired fast rise time electromagnetic step pulses.

Figure 5:
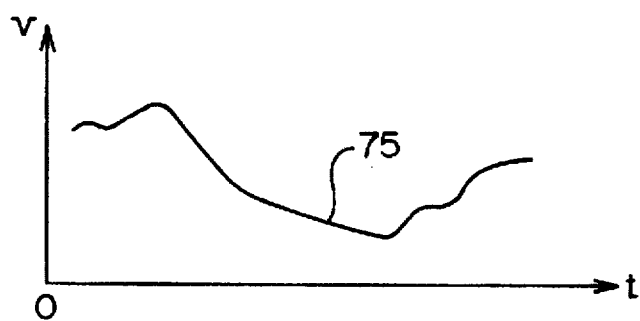
FIG. 5 is a plot of voltage versus time substantially identical to that shown in FIG. 3, again illustrating a representative reflection waveform of the type commonly generated with layered soil when using the system depicted in FIG. 4 and when the two variable impedance devices or diodes are both open.
Figure 5A:
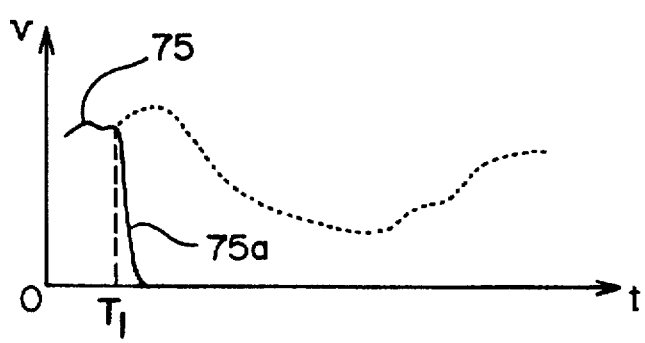
FIG. 5A is a plot of voltage versus time similar to that shown in FIG. 5, but here illustrating the representative reflection waveform as it appears when the first variable impedance device on the probe closest to the air/soil interface is remotely biased into conduction while the second variable impedance device remains open, thereby shorting the two parallel probe conductors one to the other so as to establish a first timing marker $T_1$.
Figure 5B:
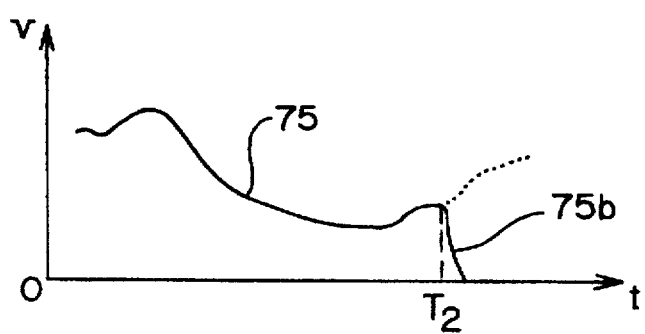
FIG. 5B is a plot similar to that shown in FIGS. 5 and 5A, but here illustrating the representative reflection waveform produced when the second variable impedance device closest to the distal probe ends is remotely biased into conduction while the first variable impedance device remains open, thereby again shorting the two parallel probe conductors one to the other so as to establish a second timing marker $T_2$.

Considering now FIGS. 5, 5A and 5B conjointly with FIG. 4, and referring first to FIG. 5, a typical waveform 75 identical to that shown in FIG. 3 has been depicted under conditions where the switches S1, S2 in FIG. 4 are positioned in the solid line positions as shown, thereby insuring that both remotely operable, normally open, variable impedance devices 76, 78—e.g., diodes $D_1, D_2$—remain open and non-conductive. Thus, under these conditions, the repetitive series of fast rise time electromagnetic pulses are propagated down the coaxial cable 54 and transmission line probe 52' without sensing any significant artificially induced discontinuity at either point $X_1$ or $X_2$; and, therefore, such pulses produce a series of reflections from such points as the cable/probe interface 54/52', the air/soil interface, and the ends of conductors 62, 64, with a series of additional intermediate reflections generated by, for example, layer interfaces in layered soil and other dielectric discontinuities in the medium under test, all of which constitute unwanted background noise. In short, waveform 75 depicted in FIG. 5 is typical of the type of waveform found by displaying all significant reflections generated as electromagnetic pulses are propagated along a transmission line probe extending through soil or other medium to be investigated.

Referring to FIG. 5A, precisely the same waveform 75 is depicted at the moment that the switches S1, S2 are shifted to the dashed line positions shown in FIG. 4, thereby biasing variable impedance device 76 (e.g., diode $D_1$) to conduction to create a momentary short across probe conductors 62, 64; and, under these conditions, it will be observed that a large amplitude reflection is generated as indicated by the sharp negative-going ramp 75a, producing a precise and accurate timing marker $T_1$ at the time of arrival of the reflection from the shorted discontinuity at point $X_1$ when variable impedance device 76 (diode $D_1$) is rendered conductive.

Referring next to FIG. 5B, the typical waveform 75 has been depicted at the moment that switches S1, S2 are shifted to the dotted line positions indicated in FIG. 4, thus rendering variable impedance device 78 (e.g., diode $D_2$) momentarily conductive so as to create a momentary short across probe conductors 62, 64 at point $X_2$, again generating a large amplitude reflection as indicated by the sharp negative-going ramp 75b, thereby producing a second precise and accurate timing marker $T_2$ at the time of arrival of the reflection from the shorted discontinuity at point $X_2$ when variable impedance device 78 (e.g., diode $D_2$) is rendered conductive.

Figure 6:
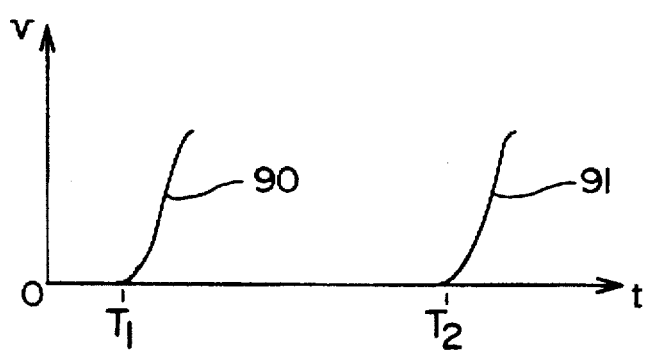
FIG. 6 is a plot illustrative of the difference waveform obtained when subtracting the shorted waveforms of FIGS. 5A and 5B from the open waveform of FIG. 5 and illustrative of: i) elimination of background noise prior to shorting of the variable impedance devices; ii) improved signal-to-noise ratio; and iii), the provision of definitive and accurate timing markers $T_1$, $T_2$ established at the intersections of the zero difference line and a best fit straight line through the positive-going ramps.

Using the electrical signaling processing capability incorporated in, for example, a conventional Tektronix Model 1502B TDR such as indicated at 51 in FIG. 4, the shorted waveforms depicted in FIGS. 5A and 5B may be readily subtracted from the open waveform shown in FIG. 5, thereby producing the difference waveform shown in FIG. 6 represented by the two positive-going ramps 90, 91, generating definitive, observable, measurable and accurate timing markers $T_1$, $T_2$ established at the intersections of the time axis and best fit straight lines drawn through respective ones of the positive-going ramps 90, 91. It will be observed upon comparison of FIG. 6 with each of FIGS. 5, 5A and 5B that utilization of such a waveform subtraction process not only serves to generate definitive, observable, measurable and accurate timing markers $T_1$, $T_2$, but, moreover, that process also serves to substantially eliminate all undesirable background noise reflections, thereby further enhancing the improved signal-to-noise ratio achievable with the present invention.

Those skilled in the art will, of course, appreciate that the particular signal processing circuits employed in the conventional TDR unit 51 shown in FIG. 4 form no part of the present invention, are completely conventional, and need not be described herein in detail. Those interested in acquiring a further explanation of the circuit details and operation of, for example, a conventional Tektronix Model 1502 TDR unit are referred to Ref. No. 2 as well as to other technical papers and product specifications available from the manufacturer, Tektronix Corp. of Beaverton, Oreg. Moreover, it will be understood that commercially available and completely conventional TDR units can be employed other than the Tektronix Model 1502B TDR instrument.

As a consequence of the foregoing arrangement, it will be understood that n normally open variable impedance devices such as PIN diodes can be fixedly mounted on the conductors of, for example, a 2-conductor probe at fixed, known, precisely located points $X_n$ (where n is any desired whole integer) so as to enable each such device to be selectively and momentarily rendered conductive to short one probe conductor to the other at precise, accurately known points $X_n$; and, to thereby create unambiguous, precise, accurate and readily observable and measurable timing markers $T_n$ wherein all measurements of $X_1$, $X_2$ ... $X_n$ and $T_1$, $T_2$ ... $T_n$ are characterized by their accuracy. As a consequence, the propagation velocity V of electromagnetic pulses transiting the probe may be calculated to a high degree of accuracy by solving for equation [1], supra; and, thereby, the apparent dielectric constant $K_a$ of the particular material being tested can be readily calculated by solving for $K_a$ in equation [2], supra, all as previously described.

While the present invention has hereinabove been described in connection with a TDR system 50' (FIG. 4) employing a conventional coaxial cable 54 to interconnect the probe 52' and the conventional TDR instrument 51, those skilled in the art will appreciate that the particular type of cable employed is not critical to the invention provided only that it possesses suitable RF transmission characteristics. It is noted, however, that highly advantageous results have been achieved, particularly, but not exclusively, in situations requiring relatively long interconnect transmission cables—e.g., cables ranging up to on the order of one hundred meters in length—where the cable comprises a 75 ohm RG-6 coaxial cable of the type designed for the cable television industry. Such coaxial cable, which is available at low cost as compared to other conventional RF transmission cables, has proven to provide excellent performance characteristics notwithstanding its relatively low cost—indeed, the performance characteristics observed have been superior to those obtained with more expensive cable.

In carrying out the present invention, it has been found that a wide variety of probe configurations are suitable dependent upon the specific application to which the probe is to be put. For example, referring to FIGS. 4 and 7 conjointly, it will be noted that the probe 52' (FIG. 4) and the probe 92 (FIG. 7) are both what have been termed in the art as "2-rod probes" or "2-wire probes"—i.e., probes having two (2) spaced, parallel, conductors. Such 2-rod or 2-wire probes are of the type which have been typically used in the prior art in combination with a balun transformer in an attempt to minimize impedance mismatch problems between the coaxial cable and the probe. Zegelin et al., Ref. No. 28; International Publication No. WO89/12820 based upon White et al. International Patent Application No. PCT/AU/89/00266.

It has been found, however, that when employing remotely operable, normally open, variable impedance devices—for example, a pair of PIN diodes $D_1$, $D_2$—with otherwise conventional 2-rod or 2-wire probes, unambiguous, relatively large amplitude, and readily observable and measurable timing markers $T_1$, $T_2$ are generated. More specifically, such timing markers $T_1$, $T_2$ are characterized by their preciseness, accuracy and reliability, and permit determination of: i) the precise points $X_1$, $X_2$ ... $X_n$ where electrical discontinuities of interest occur along the probe; and ii), the precise times of arrival of reflections of interest $T_1$, $T_2$ ... $T_n$, all without the need to employ a balun transformer or any other type of impedance matching transformer or the like.

Comparing the probe 52' of FIG. 4 with the probe 92 depicted in FIG. 7, it will be observed that the two probes are essentially identical except that in the probe 52', the diode $D_1$ is imbedded in the dielectric material defining the base-like support 65 for the probe which is normally located at, or very close to, the air/soil or other air/material interface; whereas in the probe 92 shown in FIG. 7, the diode $D_1$ is positioned closer to the coaxial cable/probe interface 54/92. It has been found, however, that any given diode $D_n$ need not be positioned precisely at a point $X_n$ provided only that the time delay difference for reflections generated at a specific point $X_n$ and reflections generated at the actual position of the diode $D_n$ is small, constant and known. Thus, as shown in the exemplary arrangement depicted in FIG. 7, it is possible to position the diode $D_1$ a short distance A from the desired location of $X_1$ at the air/soil interface; and, to then make a calibrating measurement to correct the time of arrival $T_1$ for the reflection induced by forward biasing diode $D_1$ to conduction so as to compensate for the small, constant and known differential distance A. This may be accomplished by simply placing a shorting bar (not shown) at location $X_1$, comparing the time delay read with the shorting bar in place to the time delay read when diode $D_1$ is conductive, and adjusting the $T_1$ timing marker for the small time difference calculated.

Referring to FIG. 8, a modified probe 94 also embodying features of the invention has been illustrated—such probe 94 here comprising a 3-rod probe of the type described by Zegelin et al., Ref. No. 28, and in International Publication No. WO89/12820 based upon White et al. International Patent Application No. PCT/AU89/00266, which 3-rod probe serves to more closely emulate the impedance characteristics of a typical coaxial cable. As here shown, probe 94 includes a dielectric base member 65, a central probe conductor 95 coupled to the central conductor 66 of the coaxial cable 54, and a pair of outer probe conductors 96, 98 which are disposed on opposite sides of the central probe conductor 95 and are parallel thereto, with such outer probe conductors 96, 98 being coupled to the coaxial cable shield 68. In this instance, however, three (3) variable impedance devices are employed—viz., i) one variable impedance device which here takes the form of a normally open PIN diode $D_1$ serving to couple the central conductor 66 of the coaxial cable 54 to the coaxial shield 68 adjacent the cable/probe interface 54/94 and, therefore, which is in close proximity to the air/soil interface (not shown); and ii), a pair of normally open PIN diodes $D_2$, $D_2'$ respectively coupling the distal ends of the outer probe conductors 96, 98 to the distal end of the central probe conductor 95.

Thus, the arrangement is such that when probe 94 (FIG. 8) is substituted for probe 52' in FIG. 4, all diodes $D_1$, $D_2$, $D_2'$ remain open and non-conductive when the switches S1, S2 are in the solid line positions shown in FIG. 4. However, when the switches S1, S2 are shifted to the dashed line positions shown in FIG. 4, a positive bias voltage is applied to the central probe conductor 95 via series resistors R1, R2 and the central conductor 66 of the coaxial cable 54, thereby forward biasing diode $D_1$ to conduction to create a momentary short adjacent the air/media interface and generating a first timing marker $T_1$. When the switches S1, S2 are shifted to the dotted line positions shown in FIG. 4, a positive biasing voltage is then applied to the outer probe conductors 96, 98 via the coaxial cable shield 68, forward biasing the diodes $D_2$, $D_2'$ to conduction and shorting the outer probe conductors 96, 98 to the central probe conductor 95 at point $X_2$ adjacent the probe conductor distal ends, thereby generating a second timing marker $T_2$ in the manner previously described.

When dealing with certain test media where the material to be tested is relatively homogeneous—for example, measurements of soil water content in seedling nurseries and the like—it has been found that the natural reflection $T_2$ from the transmission line end is typically large and free of distortion even in the absence of a passive or active physical device for establishing a shorted electrical discontinuity at or adjacent the probe's distal end; and, consequently, where 2-rod or 3-rod probes of the type depicted in FIGS. 7 and 8 are employed, the use of a variable impedance device at or adjacent the distal probe end is not necessary in practice since the natural reflection from the probe's distal end can provide an unambiguous, detectable and measurable reflection establishing the timing marker $T_2$. Therefore, 2-rod or 3-rod probes employing only a single variable impedance device—e.g., a single diode $D_1$—capable of generating a timing marker $T_1$ at a position adjacent the air/media interface have been found to be completely satisfactory and acceptable for use in such homogeneous test media. Examples of such 2-rod and 3-rod probes employing only a single PIN diode $D_1$ have been illustrated in FIGS. 9 (a 2-rod probe 92') and 10 (a 3-rod probe 94'). It will be understood that when using probes such as depicted at 92', 94' in FIGS. 9 and 10, rendering the diode $D_1$ momentarily conductive serves to generate a first unambiguous reflection defining timing marker $T_1$, while the second timing marker $T_2$ is generated by the natural reflection from the probe's distal end.

Turning next to FIGS. 11 and 12, there has been illustrated a modified 2-rod probe embodying features of the present invention, here generally indicated at 99, which here takes the form of a unitary, integral, imperforate, blade-like, bayonet-type probe that might also be termed a "stripline" probe. As here shown, the probe 99 comprises a pair of elongate flat conductors 100, 101 having rectangular cross sections as shown in FIG. 12, with the two conductors 100, 101 being spaced apart by, and integrally bonded to, an interior or central non-conductive dielectric spacer 102. Oppositely directed, normally open, remotely operable PIN diodes $D_1$, $D_2$ or other suitable variable impedance devices are imbedded in the dielectric spacer 102 adjacent the opposite ends of the probe 99 at respective ones of points $X_1$, $X_2$, with each diode being electrically coupled to the conductors 100, 101.

In the exemplary probe 99 illustrated in FIG. 11, the distal ends of the conductors 100, 101 and the intermediate dielectric spacer 102 are shaped to define a pointed probe end, as indicated at 104, so as to allow the probe 99 to be easily inserted into the soil or other test medium without significant disturbance thereof. While the bayonet-type probe 99 depicted in FIGS. 11 and 12 employs conductive rods 100, 101 formed of flat, bar-like, stainless steel stock of rectangular cross section, the conductors can have other configurations including, merely by way of example, oval, round, knife-edged, channel-shaped, or the like; but, since the conductors are preferably formed of stainless steel which is difficult to work, it has been found effective when the conductors are simply formed of flat, bar-like stock as shown.

In carrying out the present invention, the non-conductive dielectric material used to form, for example, the dielectric spacer 102 of the bayonet-type stripline probe 99 depicted in FIGS. 11 and 12 (or the probe base supports 65 for the probes depicted in FIGS. 4 and 7 through 10), is preferably selected for its ease of workability, impact resistance, durability, non-conductive characteristics, sealability and/or security of encapsulated electric components such as PIN diodes, and its low shrink characteristics during cure. While a wide range of dielectric epoxy materials are suitable for this purpose, excellent results have been achieved using SEALTRONIC (a trademark of Industrial Formulators of Canada Ltd.) resin epoxy encapsulate, Product No. 21AC-7V available from Industrial Formulatots of Canada Ltd. in Burnaby, British Columbia, Canada. This particular epoxy material comprises a two-part liquid potting compound developed for the electronics industry consisting of a liquid resin and a liquid hardener. When the resin and hardener are thoroughly mixed in proportions of two parts resin to one part hardener, the resulting mixed liquid epoxy remains pourable and workable for approximately sixty (60) minutes at 20° C. (68° F.). The cure time for this epoxy material is approximately forty-eight (48) hours at 20° C. (68° F.) or approximately one (1) hour at 65° C. (150° F.); and, the resulting cured dielectric epoxy material comprises a non-porous, water and chemical resistant, and extremely impact resistant material that exhibits shrinkage of less than 0.5% during cure which has been found to be particularly suitable for use with the present invention.

Unfortunately, however, in those instances where the probe conductors are formed of stainless steel—for example, as are the exemplary conductors 100, 101 of the bayonet-type probe 99 depicted in FIGS. 11 and 12—it has been found difficult to achieve an adequate and enduring bond between the stainless steel conductors 100, 101 on the one hand and the dielectric spacer 102 on the other. This problem may, however, be readily resolved by employing bonding techniques similar to those illustrated diagrammatically in: i) FIGS. 13–17; and ii), FIG. 18.

Thus, in keeping with this aspect of the invention, a flexible, elongate, wire 105 formed of stainless steel or similar weldable conductive material is formed into a generally sinuous configuration and bonded to the inner facing surfaces 106, 108 of each of the stainless steel conductors 100, 101, for example, by welding at points 109 to form facing integral, unitary, conductor/wire assemblies 100/105, 101/105 wherein each wire 105 is spaced from the conductors 100, 101 to which it is welded at spaced points along the length thereof. Two pairs of connector pins or tabs 110 are then welded adjacent one end of each tab to the inwardly facing surfaces 106, 108 of the probe conductors 100, 101 adjacent the opposite ends of the probe 99. The free ends of each pair of tabs 110 are then soldered to the leads of respective ones of a pair of oppositely directed diodes $D_1$, $D_2$ (FIGS. 16, 17) which are mounted on respective ones of a pair of small circuit boards 111 which are inserted between the probe conductors 100, 101 adjacent the opposite ends thereof.

At this point, the assembly thus far formed consisting of: i) the spaced stainless steel conductors 100, 101; ii) the sinuous wires 105 welded to the inner facing surfaces 106, 108 thereof; and iii), the printed circuit boards 111 bearing thereon PIN diodes $D_1$, $D_2$ and having their connector pins or tabs 110 welded to the stainless steel conductors 100, 101 adjacent the opposite ends thereof; are placed in a suitable mold (not shown) which defines the ultimate desired shape of the probe such, for example, as the bayonet-like shape depicted in FIGS. 11 and 13. The liquid epoxy material consisting of the thoroughly mixed resin and hardener is then poured into the mold in liquid form where it completely fills the cavity defined by the two spaced apart stainless steel conductors 100, 101 and totally surrounds the sinuous wires 105 and circuit boards 111 upon which the diodes $D_1$, $D_2$ are mounted. Consequently, when the epoxy material has been fully cured, the resulting probe comprises a unitary, integral, imperforate probe 99 consisting of: i) spaced conductors 100, 101; ii) an intermediate dielectric spacer 102 which is securely bonded in place by virtue of the imbedded wires 105 which are welded to the inner faces 106, 108 of the conductors; and iii), diodes $D_1$, $D_2$ which are totally imbedded in the cured dielectric material and protected thereby, while at the same time, they are electrically coupled to the conductors 100, 101 by virtue of the connector pins or tabs 110 which are welded at 112 directly to the conductors.

Turning now to FIG. 18, a slightly modified technique for establishing a secure and enduring bond between spaced stainless steel conductors 100, 101 and an intermediate dielectric spacer 102 has been illustrated. Thus, in this arrangement, V-shaped saw cuts 114 or the like are formed at spaced points along the inwardly facing surfaces 106, 108 of the conductors 100, 101. Consequently, when the assembly—including circuit boards and diodes (not shown in FIG. 18) similar to those depicted in FIGS. 13, 16 and 17—is placed in a suitable mold (not shown) and the liquid epoxy material is poured into the cavity between the conductors 100, 101, the liquid epoxy fills the V-shaped saw cuts 114 so that upon curing, the unitary, solidified, epoxy material defining the dielectric spacer 102 extends laterally into the saw cuts 114 and serves to prevent separation of the conductors 100, 101 from the dielectric spacer 102.

Those skilled in the art will, of course, appreciate that the arrangement depicted in FIG. 18 will provide an improved, more enduring bond between the conductors 100, 101 and the dielectric spacer 102 resisting separation of the components in the plane of the probe; but, such arrangement will not provide significant enhancement of the bond when impacts or other forces are exerted normal to, or at an angle to, the plane of the probe. Where this presents a problem, the inwardly facing surfaces 106, 108 of the conductors can also be provided with either continuous or discontinuous longitudinal grooves (not shown) so that when the liquid epoxy is poured into the cavity between the conductors 100, 101, such grooves will be filled with epoxy which, when cured and hardened, will form a tongue-and-groove joint (not shown) providing strength and an enhanced bond resisting impacts and other forces tending to separate the parts and which may be applied either normal to, or at an angle to, the plane of the probe.

It will, of course, be recognized by those skilled in the art that other structures can be designed and/or fabricated to achieve essentially the same results. For example, although not shown in the drawings, the probe conductors 100, 101, which are here shown formed from stainless steel bar stock of rectangular cross-section, could each be channel-shaped—e.g., a conductor having a C-shaped cross-section—with a C-shaped wire screen or the like welded across the open faces of the C-shaped channel.

Figure 19:
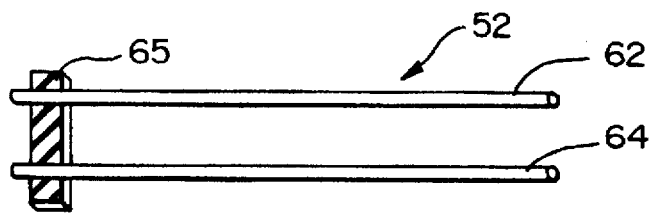
FIG. 19 is a diagrammatic, block-and-line, perspective drawing of a conventional two-prong prior art probe of the type shown in FIG. 1.

In accordance with another of the important aspects of the present invention, provision is made for enabling simple conversion of conventional 2-rod probes of the type illustrated at 52 in FIGS. 11 and 19 to generally thin, flat, bayonet-type, stripline probes embodying features of the present invention wherein n active, normally open, remotely operable, variable impedance devices are incorporated in the probe so as to permit selectively rendering such n device(s) momentarily conductive to short the probe conductors at n point(s) $X_n$ (where n is any desired whole integer), thereby enabling generation of precise, accurate and unambiguous reflections of relatively large amplitude which are readily observable, detectable and measurable to define accurate timing markers $T_n$. To accomplish this, and as best shown by reference to, for example, FIGS. 19 through 23 conjointly, the present invention provides for the use of a sheath-like adaptor, generally indicated at 115 in FIG. 20, which can be easily slid onto a conventional 2-rod probe—such, for example, as the conventional probe 52 depicted in FIGS. 1 and 19—so as to convert such conventional probe 52 into a relatively thin, flat, bayonet-type, stripline probe embodying features of the present invention.

Thus, referring first to FIG. 19, it will be noted that the conventional prior art probe 52 there illustrated is identical to the conventional prior art probe 52 shown in FIG. 1, having a pair of spaced, parallel, rod-like conductors 62, 64 formed of stainless steel or the like which are secured at one end to a dielectric support base 65. In other words, the probe 52 is similar to conventional 2-rod or 2-wire probes of the type described in Zegelin et al., Ref. No. 28, and in International Publication No. WO89/12820 based upon White et al. International Patent Application No. PCT/AU89/00266.

The sleeve-like adaptor 115, in turn, comprises an assembly including a pair of identical tubular conductors 116R, 116L formed of stainless steel or the like. Each such tubular conductor is, preferably, of generally d-shaped cross section, having a cylindrical or tubular portion 118R, 118L complemental in shape to the cross-sectional shape of the probe conductors 62, 64 and terminating in integral tangential flanges 119R, 119L, as best shown by reference to FIGS. 21 through 23. The inside diameters of the tubular portions 118R, 118L of the tubular conductors 116R, 116L are dimensioned such that the pair of tubular conductors 116R, 116L will slide over and accommodate respective ones of the rod-like conductors 62, 64 on the conventional 2-rod probe 52 (FIG. 19) with a snug fit providing good electrical contact therebetween.

Figure 22:
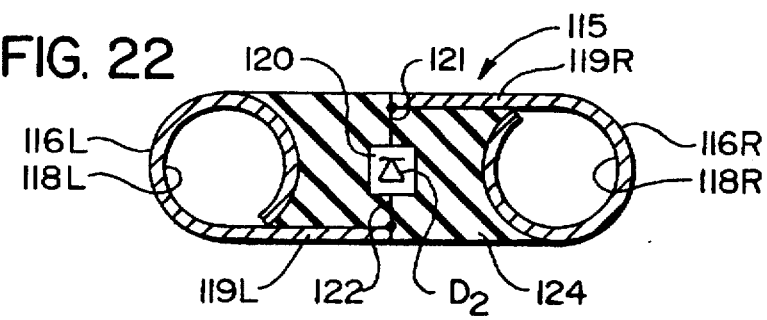
FIGS. 22 and 23 are sectional views of the sheath shown in FIG. 20, here taken substantially along respective ones of the lines 22—22 and 23—23 in FIG. 20.
Figure 23:
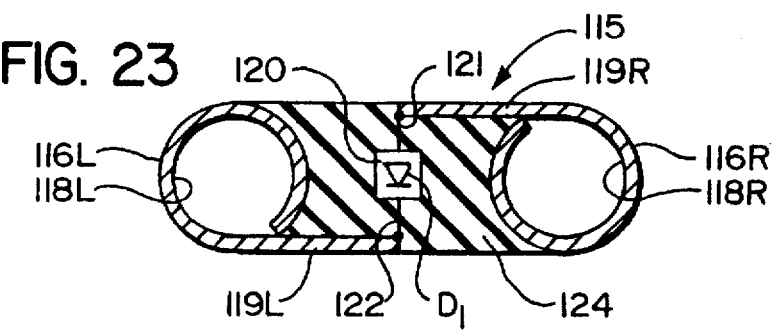

As best shown in FIGS. 22 and 23, a pair of active, remotely operable, normally open, variable impedance devices such, for example, as normally open diodes $D_1$, $D_2$ mounted on small circuit boards 120, are, respectively, electrically coupled adjacent the opposite longitudinal ends of the two flanges 119R, 119L which are oriented such that flange 119R defines the upper right half of the surface of the adaptor 115 as viewed in the drawings, while flange 119L defines the lower left half of the surface of the adaptor 115, with the two flanges lying in parallel planes and extending towards a vertical plane extending through the longitudinal centerline of the adaptor 115. The longitudinal axes of the tubular portions 118R, 118L are spaced apart and parallel; and, lie on axes coincident with the axes of the parallel conductors 62, 64 of the probe 52 when the adaptor 115 and probe 52 are assembled.

In assembly of the adaptor 115, the tubular conductors 116R, 116L are positioned in any suitable jig-like mold (not shown); the diodes $D_1$, $D_2$ on the respective circuit boards 120 are properly positioned and soldered to connector pins or tabs 121, 122 respectively welded to the flanges 119R, 119L; and, the remaining cavity therebetween is then filled with a liquid 2-component epoxy material which, when cured, defines a hard, durable, impact resistant dielectric spacer 124 between the tubular conductors 116R, 116L terminating at its distal end in a relatively sharp point 125 to facilitate insertion of the probe/adaptor combination 52/115 into the test medium without undue disturbance thereof. In this arrangement, the dielectric spacer 124 serves to encapsulate, and thus protect, the diodes $D_1$, $D_2$. Although not shown in the drawings, those skilled in the art will appreciate that where the tubular conductors 116R, 116L are formed of stainless steel or the like, the dielectric spacer 124 can be formed from the same epoxy material as previously described to form the spacer 102 on the probe 99 depicted in FIGS. 11 and 12. Moreover, the same type of bonding techniques as previously described in connection with FIGS. 13 through 18 can be employed when assembling the sheath-like adaptor 115 in a suitable jig.

Thus, the arrangement is such that the assembled sheath-like adaptor 115 can be readily slipped on, or removed from, the rod-like conductors 62, 64 of an otherwise completely conventional 2-rod probe such as indicated at 52 in FIG. 19. When slipped on the conductors 62, 64, tubular conductor 116R telescopically receives and houses probe conductor 62 in intimate electrical contact therewith; tubular conductor 116L telescopically receives and houses probe conductor 64 in intimate electrical contact therewith; and, diodes $D_1$, $D_2$ define oppositely directed, normally open, remotely operable, active, variable impedance devices adjacent respective ones of the opposite longitudinal ends of the adaptor 115 and, therefore, adjacent opposite ends of the probe 52 assembled therewith. If desired, suitable conductive set screws or the like (not shown) can be employed to lock the adaptor 115 in place with respect to the probe conductors 62, 64, while, at the same time, insuring good electrical contact between the tubular conductors 116R, 116L and respective ones of the probe conductors 62, 64.

In usage of TDR systems employing sheath-like probe adaptors of the foregoing type, it is merely necessary to place the adaptor 115 on the conventional 2-rod probe 52 and provide a bias insertion network such as indicated at 79 in FIG. 4 capable of selectively and sequentially biasing the diodes $D_1$, $D_2$ to momentary conduction. Thus, the system can be operated in the manner previously described in connection with FIG. 4, but using a completely conventional 2-rod probe 52 in combination with the adaptor 115 which serves to convert the conventional 2-rod probe to a relatively thin, flat, bayonet-type, stripline probe embodying features of the present invention.

In further keeping with the foregoing aspects of the present invention, provision is also made for converting a completely conventional prior art 3-rod probe—for example, a probe of the type described and developed by Zegelin et al., Ref. No. 28; and, also described in International Publication No. WO89/12820 based upon White et al. International Patent Application No. PCT/AU89/00266 such as the probe 69 depicted in FIGS. 2 and 24—into a relatively thin, flat, bayonet-type, stripline probe embodying features of the present invention. To this end, a modified sheath-like adaptor, generally indicated at 126 in FIGS. 25, 26 and 27, is provided for usage with a conventional 3-rod probe 69 (FIGS. 2 and 24) having three (3) spaced parallel conductors—viz., a central conductor 70 and a pair of parallel outer conductors 71, 72—secured to a dielectric support base 65.

Figure 24:
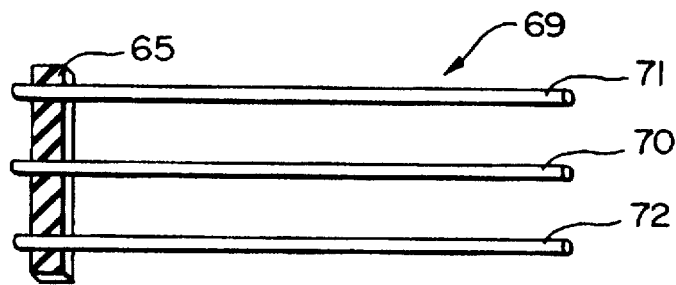
FIG. 24 is a diagrammatic, block-and-line, perspective drawing of a conventional three-prong prior art probe of the type shown in FIG. 2.
Figure 25:
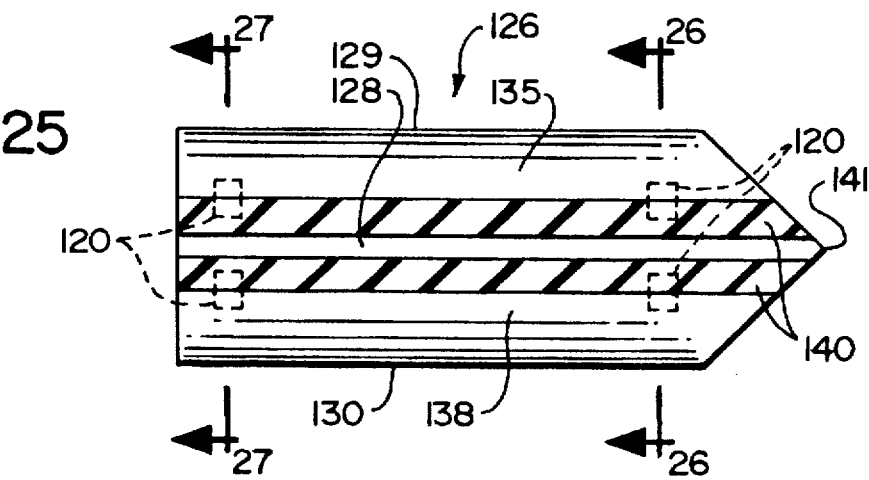
FIG. 25 is a plan view, partly in section, similar to FIG. 20, but here depicting a modified form of bayonet-like sheath adapted to be placed in side-by-side relation with the conventional prior art three-pronged probe of FIG. 24 and intended to be considered conjointly therewith, and adapted to be slidably mounted on, and engaged with, the conventional prior art three-pronged probe of FIG. 24 in a manner similar to that described for the sheath of FIG. 20 so as to convert the conventional prior art three-pronged probe into a solid, integral, bayonet-like probe embodying features of the present invention which is similar to the solid, integral two-pronged probe of FIG. 11, differing therefrom in that the resulting probe employs three spaced parallel conductors and four remotely operable shorting diodes.
Figure 26:
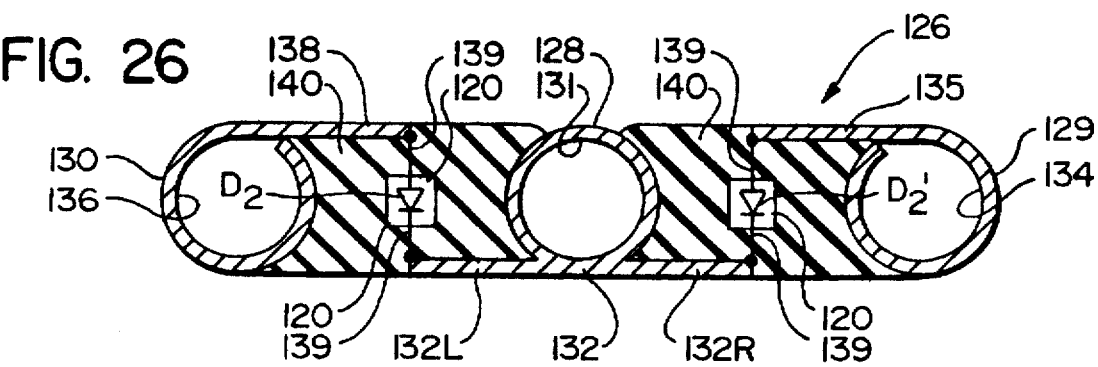
FIGS. 26 and 27 are sectional views of the sheath shown in FIG. 25, here taken substantially along respective ones of the lines 26—26 and 27—27 in FIG. 25.
Figure 27:
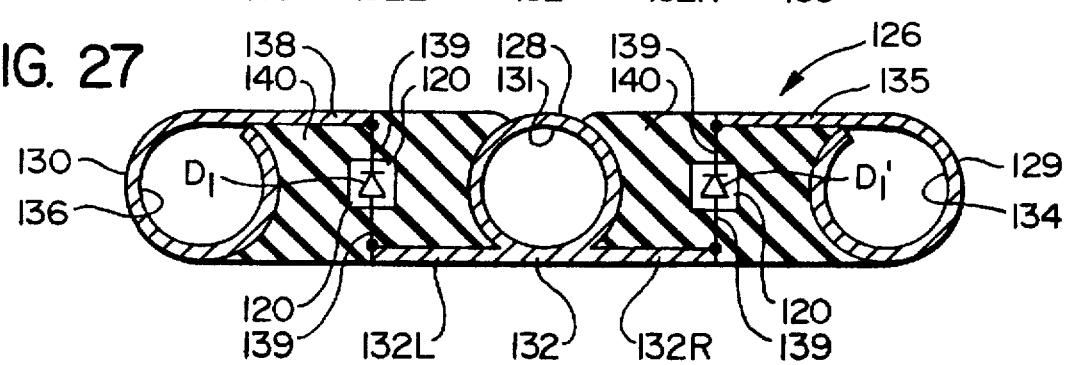

Thus, as will be best appreciated by reference to FIGS. 25, 26 and 27 conjointly, it will be observed that the modified sheath-like adaptor 126 includes three (3) spaced parallel conductors 128, 129, 130 disposed on parallel longitudinal axes having the same spacing as the parallel longitudinal axes for the conductors 70, 71, 72 of probe 69 (FIG. 24). In the exemplary device, conductor 128 includes a tubular portion 131 and a tangential flange 132 having right and left flange portions 132R, 132L adapted to lie along the lower surface of the adaptor 126 as viewed in FIGS. 26 and 27. Conductor 129 has a generally d-shaped cross-section defined by a tubular portion 134 and a tangential flange 135 adapted to lie along the upper right longitudinal surface of the adaptor 126 as viewed in FIGS. 26 and 27 in a plane parallel to, and spaced from, the flange 132R on the central tubular conductor 128; while conductor 130 is similarly shaped having a tubular portion 136 and a tangential flange 138 lying along the upper left longitudinal surface of the adaptor 126 as viewed in FIGS. 26 and 27 in a plane parallel to, and spaced from, the flange 132L on the central tubular conductor 128.

In this arrangement, a pair of normally open, remotely operable, variable impedance devices such as oppositely directed diodes $D_1$, $D_2$ (FIGS. 26 and 27) mounted on small circuit boards 120 are electrically connected adjacent opposite longitudinal ends of the conductors 128, 130 to the left flange 132L on the central tubular conductor 128 and the flange 138 on the left tubular conductor 130. Such electrical connection includes connector pins or tabs 139 welded at one end of each tab to the conductor flanges 132L, 138 adjacent opposite ends thereof; with the opposite ends of the tabs 139 then being soldered to respective ones of the diodes $D_1$, $D_2$ on circuit boards 120. In like manner, a second pair of oppositely directed diodes $D_1'$, $D_2'$ (FIGS. 26 and 27) mounted on small circuit boards 120 are electrically connected adjacent opposite longitudinal ends of the tubular conductors 128, 129 to the right flange 132R on the central tubular conductor 128 and the flange 135 on the right tubular conductor 129.

Once the tubular conductors 128, 129, 130 have been placed in a jig-like mold (not shown) and oriented in the relative positions depicted in FIGS. 26 and 27: i) the connector pins or tabs 139 are welded to the conductor flanges 132L, 132R, 135, 138; and ii), the diode pairs $D_1$, $D_2$ and $D_1'$, $D_2'$ mounted on the small circuit boards 120 are properly positioned and the leads on diodes $D_1$, $D_2$ and $D_1'$, $D_2'$ are soldered to the free ends of the tabs 139 so as to electrically couple the diode pairs $D_1$, $D_2$ and $D_1'$, $D_2'$ across the respective flange pairs 132L, 138 and 132R, 135. Thereafter, the two-part liquid epoxy material previously described is poured into the cavity defined between the tubular conductors 128, 129 and 128, 130 to form, after curing, a hardened, impact resistant, dielectric spacer 140 having a pointed distal end 141 (FIG. 25) formed of dielectric material to facilitate insertion into soil and similar test media.

Consequently, upon assembly of the relatively thin, flat, bayonet-type, stripline, sheath-like adaptor 126 depicted in FIGS. 25 through 27 on the conventional 3-rod probe 69 depicted in FIG. 24, the diodes $D_1$, $D_1'$ serve as remotely operable, normally open, active, shorting devices for momentarily shorting the central telescoped conductors 70/128 to the outer telescoped conductors 71/129 and 72/130 adjacent the air/media interface (not shown) so as to generate a first reflection from that shorted discontinuity which serves to establish a first definitive, accurate, and unambiguous timing marker $T_1$ at a fixed, precise and known point. Similarly, the diodes $D_2$, $D_2'$ serve as remotely operable, normally open, active, shorting devices for momentarily shorting the outer telescoped conductors 71/129 and 72/130 to the central telescoped conductor 70/128 adjacent the distal ends of the probe conductors 70, 71, 72 so as to generate a reflection from a second known precise point spaced longitudinally from the diodes $D_1$, $D_1'$ by a fixed known distance, thereby establishing a second precise and accurate timing marker $T_2$.

As in the case of the adaptor 115 previously described in connection with FIGS. 20–23, when using the adaptor 126 depicted in FIGS. 25–27, the overall TDR system will include a bias insertion network, such as that indicated at 79 previously described in connection with FIG. 4, which is interposed in the coaxial cable 54 for selectively and sequentially rendering diode pairs $D_1$, $D_1'$ and $D_2$, $D_2'$ momentarily conductive during operation of the system so as to generate first and second relatively large amplitude, unambiguous reflections respectively establishing first and second precise and accurate timing markers $T_1$, $T_2$. And, once again, although not shown in the drawings, one or more conductive set screws can be employed to positively clamp the adaptor 126 to the probe conductors 70, 71, 72 while at the same time insuring that there is a sound electrical connection therebetween.

Figure 20:
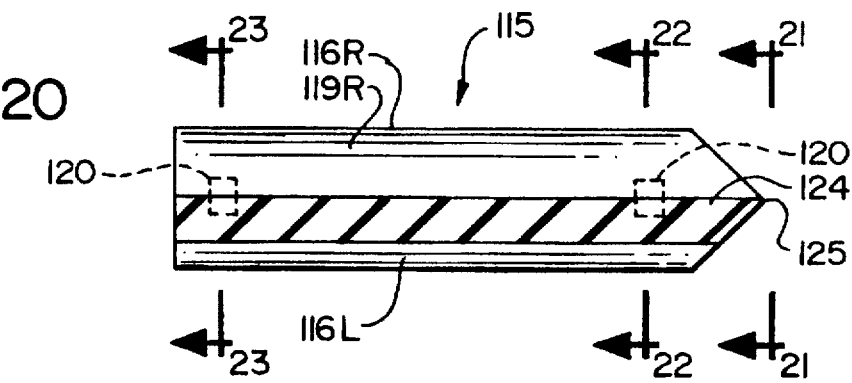
FIG. 20 is a plan view, partly in section, here adapted to be placed in side-by-side relation with the conventional probe of FIG. 19 and intended to be considered conjointly therewith, and illustrating an elongate bayonet-type sheath adapted to be mounted on the conventional prior art probe of FIG. 19 with the probe conductors being telescopically received therein, such sheath employing first and second parallel conductors spaced apart by an integral spacer formed of dielectric or other suitable non-conductive material and having a pair of variable impedance devices—e.g., remotely operable shorting diodes—imbedded in the dielectric material and coupled to the sheath's first and second electrical conductors for converting the conventional two-pronged probe of FIG. 19 to a bayonet-like solid probe structurally similar and functionally identical to the probe depicted in FIG. 11.
Figure 21:
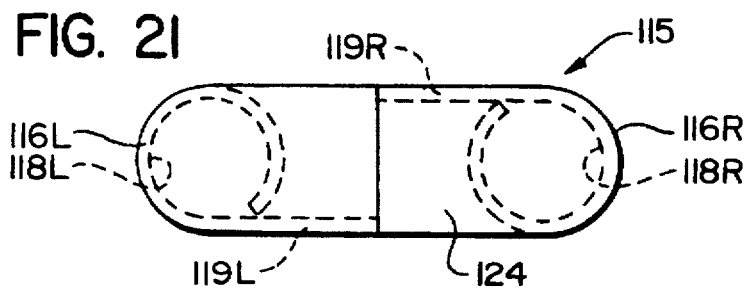
FIG. 21 is an end view of the sheath depicted in FIG. 20 taken substantially along the line 21—21 in FIG. 20.

Although not shown in the drawings, those skilled in the art will appreciate from the foregoing description that the adaptor configurations 115 and 126 shown by way of example in FIGS. 20 and 25, respectively, which enable conversion of conventional probes into probes embodying features of the invention, also define, in their own right, integral 2-conductor (FIG. 20) and 3-conductor (FIG. 25) stripline probes which can be coupled directly to a suitable RF cable interconnecting the probe to a TDR apparatus. Moreover, although not shown in FIG. 25, the distal ends of conductors 129, 130 can, where desired, be integral with a solid stainless steel probe end which is spaced from the central conductor 128 by dielectric material 140.

Turning next to FIGS. 28 and 29, yet another modified adaptor, generally indicated at 142, embodying features of the present invention has been illustrated. As here shown, the adaptor 142 is designed to be slid on the spaced, parallel, rod-like conductors 144, 145 of a conventional 2-rod or 2-wire probe; but, those skilled in the art will appreciate as the ensuing description proceeds that the adaptor 142 can, if desired, be designed and configured so as to be usable with 3-rod or 3-wire probes in a manner consistent with that described above for the adaptor 126 depicted in FIGS. 25 through 27.

More specifically, the adaptor 142 depicted in FIGS. 28 and 29 comprises: i) a relatively short, thin, flat, bayonet-type device which is not co-extensive in length with the length of the probe conductors 144, 145 as were the adaptors 115 (FIG. 20) and 126 (FIG. 25) previously described; but, rather, where the adaptor 142 comprises a relatively short assembly including a pair of spaced, parallel conductors 146, 148 each having a generally d-shaped cross-sectional configuration, best shown in FIG. 29, defining tubular portions 149, 150 and tangential flanges 151, 152; ii) a central dielectric spacer 154; and iii), a single diode $D_n$ mounted on a small circuit board 120 wherein the diode $D_n$ is coupled across the tubular conductor flanges 151, 152 by means of connector pins or tabs 155 welded to the flanges 151, 152 and thereafter soldered to the leads on the diode $D_n$, with the diode being imbedded in the dielectric spacer 154 so as to permit shorting of the telescoped conductors 144/146 to the telescoped conductors 145/148 at such time as the diode $D_n$ is momentarily biased into conduction by a suitable bias insertion network such as that shown at 79 in FIG. 4. As best illustrated in FIG. 28, it will be noted that the tubular conductors 146, 148 and their respective flanges 151, 152, as well as the dielectric spacer 154, are shaped to form a sharp pointed end 156 so as to facilitate insertion of the adaptor 142 into soil or other porous media without undue disturbance. Of course, it will be evident that the adaptor 142 depicted in FIGS. 28 and 29 can be assembled in essentially the same fashion as previously described for the adaptors 115 (FIG. 20) and 126 (FIG. 25).

In usage, the adaptor 142 is slid onto the probe conductors 144, 145 which are telescopically received within the tubular conductor portions 149, 150 in snug fitting interrelationship therewith defining good electrical contact. The adaptor may be positioned adjacent the distal ends of the probe conductors 144, 145 to provide a remotely operable, shortable electrical discontinuity adjacent the terminus of the probe; or, it may be shifted along the probe conductors 144, 145 until it is located adjacent the air/media or coaxial cable/probe interface to provide a remotely operable, shortable electrical discontinuity at that point; or, it may be positioned at any desired location along the lengths of the probe conductors 144, 145 so as to vary the effective length of the probe; or, two such adaptors 142 respectively having oppositely directed diodes $D_1$, $D_2$ (not shown) may be mounted on the probe conductors 144, 145 at two longitudinally spaced points, thereby converting a conventional 2-rod probe of fixed length to a 2-diode, 2-rod probe of any desired effective length. In any of the foregoing arrangements, the adaptor(s) is(are) preferably tightly clamped to the probe conductors 144, 145 at the desired location(s) by any suitable conductive set screws 158, 159 (FIG. 28) which serve not only to clamp the adaptor(s) in the desired location(s) but, additionally, to insure that sound electrical contacts are established therebetween.

Turning next to FIG. 30, the present invention has been illustrated as it might be incorporated for determining the average moisture level in a typical seedling nursery, generally indicated at 160. Thus, as here shown a plurality of seedlings 161 are depicted as having been planted in soil or other suitable planting mix 162 disposed in a plurality of closely spaced, discrete, wedge-shaped planting cavities 164 formed in a Styrofoam block 165. More specifically, although not shown in detail in the drawings, those skilled in the art of reforestation will appreciate that seedling nurseries will commonly employ a plurality of Styrofoam blocks 165 of the type shown in FIG. 30 wherein each block may have a plurality of wedge-shaped planting cavities 164 formed therein in a rectilinear array of, merely by way of example, ten (10) X-oriented rows and ten (10) Y-oriented columns defining a total of one hundred (100) closely adjacent planting cavities 164. The particular number of planting cavities formed in any given Styrofoam block 165 is, of course, not critical and will vary widely from seedling nursery to seedling nursery. Commonly, a plurality of such Styrofoam blocks 165 will be supported on tables in a greenhouse or other climate controlled seedling nursery facility.

Prior to the advent of the present invention, the typical way employed to determine the average moisture content of the plurality of discrete batches of planting mix 162 in the plurality of planting cavities 164 formed in any given Styrofoam block 165 was to remove the block and weigh it so as to enable comparison of the weight of the block to the normal weight of a block containing planting mix having a desired average moisture level. This common practice is not only time consuming and labor intensive, but, moreover, is often ineffective, particularly where the nursery may have tightly packed groups of such blocks 165 where the centermost blocks are not adjacent to the aisle and are not conveniently accessible to the workmen. The present invention overcomes this disadvantage by providing a plurality of moisture sensitive probes disposed in a series arrangement defining a series averaging probe, generally indicated at 166, which can be readily configured to permit determination of the average moisture of the planting mix 162 disposed, for example, in: i) an entire row of planting cavities 164; or ii), multiple adjacent or spaced rows of planting cavities 164; or iii), even all or any selected sampling of all planting cavities 164 disposed in any given block 165 or group of blocks 165.

In keeping with this aspect of the present invention, the exemplary series averaging probe 166 comprises a plurality of spaced 2-rod or 3-rod probes $168_1$, $168_2$, $168_3$ ... $168_m$ (where m is any whole integer greater than one). Typically the 2-rod or 3-rod probes $168_m$ (of which only one rod or conductor is visible in FIG. 30) may be formed of 0.09375" (3/32") diameter stainless steel welding rods or the like each having a length slightly greater than the depth of each planting cavity 164 so as to enable each probe $168_m$ to pass diagonally through the soil or other suitable planting mix 162 disposed in each planting cavity 164 with the probe conductors extending slightly above one side of the top of the cavity 164 and slightly below the opposite side of the bottom of the cavity 164.

In order to couple the plurality of probes $168_1$, $168_2$ ... $168_m$ together to form a series averaging probe 166, a plurality of flexible bottom and top couplers, generally indicated at 169, 170, are provided each including an outer flexible tubular insulator 171, an inner short length of RF transmission line 172, and a pair of internal couplers 174 at each end of the transmission line 172 and permanently affixed within each end of the flexible tubular members 171 in moisture-tight sealing relation therewith. Thus, the arrangement is such that the coupler 174 at each end of a transmission line 172 can be slidably engaged with the projecting ends of two adjacent probes-for example, one flexible bottom coupler 169 can be slidably engaged with the outwardly projecting bottom ends of the probes $168_1$, $168_2$; one flexible top coupler 170 can be slidably engaged with the outwardly projecting upper ends of the probes $168_2$, $168_3$; etc., to form a series averaging probe 166 consisting of spaced 2-rod or 3-rod probes $168_1$, $168_2$ ... $168_m$ interconnected by short lengths of insulated RF transmission line 172. Although not shown in FIG. 30, those skilled in the art will appreciate that the bottom and top couplers 169, 170 may be secured to the outwardly projecting ends of the probes $168_1$, $168_2$ ... $168_m$ in any suitable manner—for example, by set screws, clamps or the like.

In order to complete the series averaging probe 166, the probe at one end-for example, probe $168_1$—has the upper end of the probe conductors mounted in a suitable dielectric support base 175 within which is imbedded a first remotely operable, normally open, active, variable impedance device such as a PIN diode D1 (not shown in FIG. 30, but essentially the same as the arrangement illustrated for diode $D_1$ in FIG. 4) with the upper end of the conductors for the probe $168_1$ being electrically coupled to a coaxial cable 54 in the manner previously described.

Similarly, a spade-like fitting, generally indicated at 142, which may be identical to that described in connection with FIGS. 28 and 29, may be slidably mounted over the upper free ends of the conductors defining the last of the series arranged moisture sensitive probes $168_m$ so as to electrically couple a second oppositely directed, remotely operated, normally open, active, variable impedance device such as a PIN diode $D_n$ (not shown in FIG. 30, but essentially identical to the arrangement shown in FIG. 29) at the distal end of the series averaging probe 166.

As a consequence of this arrangement, the nursery operator need only couple each series averaging probe 166 in the greenhouse or other nursery facility to a TDR instrument such as that shown in FIG. 4 at 51 using a suitable bias insertion network 79 and a conventional multiplexing arrangement of, for example, the type described in Baker et al., Ref. No. 3. Since the intermediate transmission lines 172 are of short constant known length and maintained free of moisture by the insulator 171 and end couplers 174, they will contribute a known constant delay in determination of the timing marker $T_2$ generated by reflections from the momentarily shorted diode $D_n$ in the spade-like fitting 142 at the distal end of the series averaging probe 166. Therefore, measurement of the propagation velocity of electromagnetic pulses transmitted down the series averaging probe 166 will enable calculation of the average apparent dielectric constant $K_a$ for all of the discrete batches of soil or other planting mix 162 disposed within those wedge-shaped cavities 164 through which the series averaging probe 166 extends.

Indeed, this arrangement readily permits reliable and accurate measurements of average moisture content of the soil or other planting mix 162 disposed in those wedge-shaped cavities 164 that are remote from the aisle and normally inaccessible to nursery workmen. For example, in those instances where Styrofoam blocks 165 containing one or more series averaging probes 166 are located immediately adjacent the aisles through which nursery workmen can move, it is merely necessary to insure that the proximate end of each probe 166 containing the diode $D_1$ imbedded in or adjacent to the dielectric support member 175 is oriented at the edge of the Styrofoam block 165 immediately adjacent and parallel to the aisle.

On the other hand, where one or more series averaging probes 166 are located in a Styrofoam block or blocks 165 remote from an aisle—e.g., in an arrangement where the nursery includes a 10×10 array of Styrofoam blocks 165 bordered by access aisles, only the peripheral thirty-six (36)

blocks 165 will be immediately adjacent an access aisle, while the interior sixty-four (64) Styrofoam blocks 165 disposed in an internal 8×8 array will be remote from an access aisle and, therefore, they will be progressively more inaccessible to workmen for purposes of moisture measurements—it is merely necessary to run short lengths of transmission line 54 from each such less accessible series averaging probe 166 to the nearest access aisle at the time that the Styrofoam blocks 165 with their newly planted seedlings are initially positioned on the support table, platform, or other nursery work surface (not shown), thereby enabling a workman to mount the TDR instrument and bias insertion network such as respectively shown at 51 and 79 in FIG. 4 on a portable dolly which can then be moved through the aisle to permit successive coupling of the measurement equipment to all or any selected sampling of the multiplicity of series averaging probes 166 and/or the short transmission lines 54 coupled thereto. Alternatively, and as previously described above, the multiplicity of series averaging probes 166 can, irrespective of whether they are adjacent to or remote from an access aisle, be coupled through a completely conventional multiplexing system to a fixed or stationary TDR instrument 54 and bias insertion network 79 via RF transmission lines 54 of fixed and known lengths.

Figure 31:
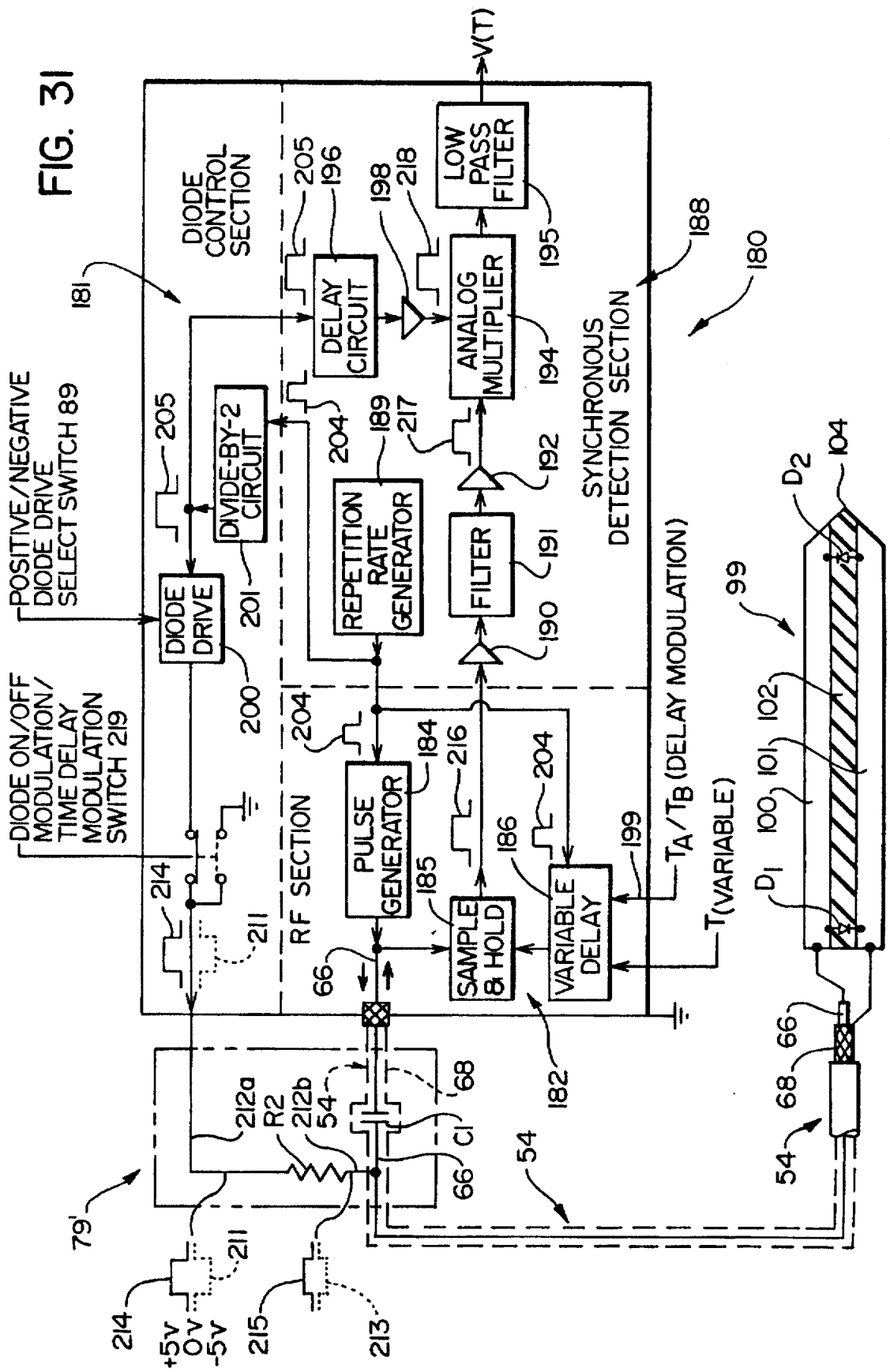
FIG. 31 is a highly diagrammatic, schematic, fragmentary block-and-line drawing, partly in section, similar to FIG. 4, but here illustrating a modified form of Time Domain Reflectometer electronics employing: i) a circuit to repeatedly switch either diode of a bayonet-like probe such as that shown in FIGS. 11 and 12 from open to short; ii) a low frequency synchronous detector signal processing circuit allowing the detection of the difference in the amplitude of the sample-and-hold circuit output arising from the diode-open reflection at time T and the amplitude of the sample-and-hold circuit output arising from the diode-shorted reflection at time T with the entire apparatus permitting the direct measurement of a difference function similar to that shown in FIG. 6; and iii), delay modulation capability for permitting waveform differentiation by modulating the time delay in synchronism with the Time Domain Reflectometer repetition rate so as to allow a single electronic unit to determine passive as well as active timing markers.

In accordance with another of the important aspects of the present invention, and as will be best understood by reference to the ensuing description in connection with FIGS. 31 through 34, there has been illustrated a modified, but exemplary, form of electronic TDR apparatus, generally indicated at 180 in FIG. 31, embodying features of the present invention and here employing: i) a Diode Control Section, generally indicated at 181, for enabling repeated switching of either diode $D_1$ or $D_2$ in a two-diode bayonet-like probe—e.g., a probe such as that indicated at 99 in FIGS. 11, 12 and 31—between open and shorted states; ii) an RF Section, generally indicated at 182, containing a Pulse Generator 184, a Sample-And-Hold circuit 185, and Variable Delay circuitry 186; and iii), a low frequency Synchronous Detection Section, generally indicated at 188, comprising a signal processing circuit containing: a) a Repetition Rate Generator 189; b) an AC Amplifier 190, Filter 191, AC Amplifier 192, Analog Multiplier 194 and Low Pass Filter 195 connected in series and receiving signals output from the Sample-And-Hold circuit 185 in the RF section 182; and c), a Delay circuit 196 and an AC coupled Buffer Amplifier 198 for coupling square wave output pulses from the Diode Control Section 181 to the Analog Multiplier 194 in a manner described hereinbelow with more particularity.

It should be noted that the circuits within each of the blocks diagrammatically illustrated in FIG. 31—viz., block 184 (Pulse Generator), block 185 (Sample-And-Hold circuit), block 186 (Variable Delay circuitry), block 189 (Repetition Rate Generator), blocks 190 and 192 (AC Amplifiers), block 191 (Filter), block 194 (Analog Multiplier), block 195 (Low Pass Filter), block 196 (Delay circuit) and block 198 (AC Buffer Amplifier)-are completely conventional and may vary widely as matters of choice and circuit design dependent upon the particular designer and the specific applications involved and/or results desired. Consequently, the specific circuit details employed in each of such block components need not be, and are not, described herein in detail.

In the exemplary circuitry depicted in FIG. 31, the signal processing circuitry defining the Synchronous Detection Section 188 permits direct detection of the difference in amplitude of the output from the Sample-And-Hold circuit 185 arising from the diode-open reflection at time T and the amplitude of the output from the Sample-And-Hold circuit 185 arising from the diode-shorted reflection at time T, with the entire TDR apparatus 180 permitting the direct measurement of a difference function similar to that shown in FIG. 6. A Delay Modulation input 199 to the Variable Delay circuitry 186 in the RF Section 182—i.e., input circuitry (not shown) for rapidly and alternately switching the Variable Delay circuitry 186 between a first time delay $T_A$ and a second T delay $T_B$—permits waveform differentiation by modulating the time delay in synchronism with the TDR repetition rate established by the Repetition Rate Generator 189 so as to allow a single modified electronic TDR apparatus 180 embodying features of the present invention to detect passive as well as active timing markers.

Figure 32:
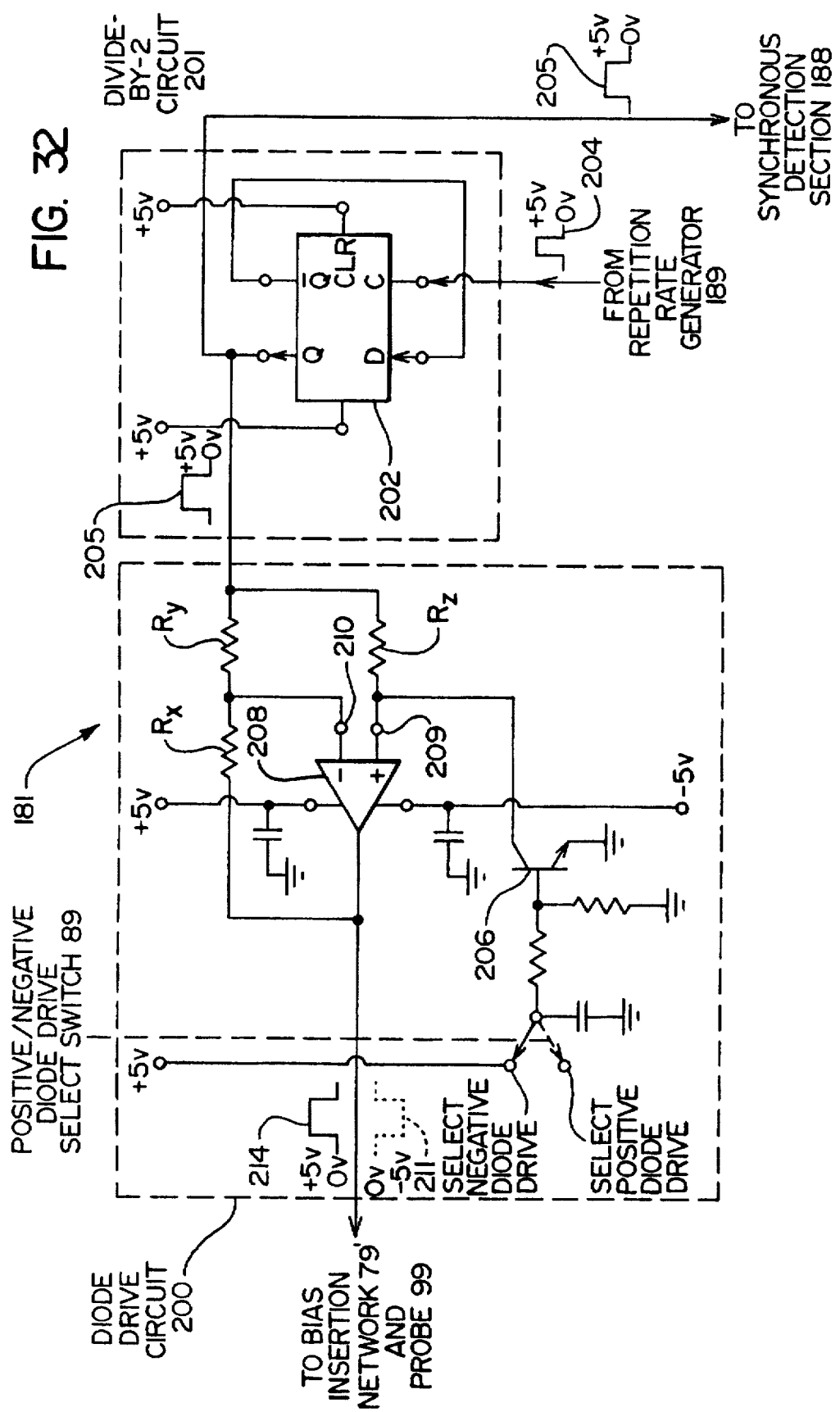
FIG. 32 is a schematic drawing depicting the circuit components employed in the Divide-By-2 and the Diode Drive circuits shown in block form in FIG. 31.

In carrying out this aspect of the invention, and as will be best understood by reference to FIGS. 31 and 32 conjointly, provision is made for selectively switching the diodes $D_1$, $D_2$ in the probe 99 (FIG. 31) between the open and shorted states. To this end, the Diode Control Section 181 includes a Diode Drive circuit 200 and a Divide-By-2 circuit 201. In the exemplary circuitry depicted in FIG. 32, the Divide-By-2 circuit 201 comprises a bi-stable flipflop 202 which receives a clock signal at its input terminal C in the form of a square wave pulse 204 output from the Repetition Rate Generator 189 (FIG. 31) to each of the Pulse Generator 184, Variable Delay circuitry 186, and the Divide-by-2 circuit 201—such clock pulse 204 ranging from zero volts (0 v) to plus five volts (+5 v). Each input clock signal or pulse 204 serves to copy the signal present on the input terminal D of the flipflop 202 on its output terminal Q. For example, when the input terminal D is low—i.e., at zero volts (0 v)—an input square wave pulse signal 204 at the clock terminal C causes the zero volt (0 v) low signal present at input terminal D to be reflected at the Q output terminal; while, at the same time, a high signal level—i.e., plus five volts (+5 v)—is presented at the $\overline{Q}$ output terminal of the flipflop 202, which high output signal is then reflected at the input terminal D.

Consequently, the next clock signal 204 derived from the Repetition Rate Generator 189 causes the plus five volt (+5 v) high input signal at input terminal D to be transferred to the Q output terminal and a low, or zero volt (0 v), signal to be presented at the $\overline{Q}$ output terminal of the flipflop 202 which is then reflected at the D input terminal. In short, alternate input clock signals 204 derived from the Repetition Rate Generator 189 cause the Q output signal level to alternate between zero volts (0 v) and plus five volts (+5 v), thereby producing one-half as many rising pulse edges at the Q output terminal of the flipflop 202 as are input on the input clock terminal C—i.e., a train of positive-going square wave pulses 205 is produced at the output terminal Q of the flipflop 202 having a frequency one-half (½) the frequency of the input clock pulses 204 derived from the Repetition Rate Generator 189.

Each square wave pulse signal 205 ranging from zero volts (0 v) to plus five volts (+5 v) output from the Q output terminal of the bi-stable flipflop 202 is then delivered to both the Delay circuit 196 in the Synchronous Detection Section 188 and the Diode Drive circuit 200 in the Diode Control Section 181. As shown in FIG. 32, the exemplary Diode Drive circuit 200 includes: i) a transistor switch 206; ii) an Operational amplifier 208 having a positive lower path input terminal 209, a negative upper path input terminal 210, and resistors $R_x$, $R_y$ and $R_z$ where $R_x$ is equal to $R_y$ and either equal to, or approximately equal to, $R_z$ (in a practical embodiment of the invention, all three resistors $R_x$, $R_y$, $R_z$ are 10K resistors); and iii), a POSITIVE/NEGATIVE Diode Drive Select Switch 89 for enabling selective switching of one of the two diodes $D_1$, $D_2$ in the probe 99 (FIG. 31).

Thus, the arrangement is such that when the POSITIVE/ NEGATIVE Diode Drive Select Switch 89 is in the solid line position shown in FIG. 32—i.e., the SELECT NEGATIVE Diode Drive position—the transistor switch 206 is turned ON, coupling the positive lower path input terminal 209 of the operational amplifier 208 to ground. Under these conditions, the positive-going square wave pulses 205 which are output from the Divide-By-2 circuit 201 are input to the operational amplifier 208 via its negative upper path input terminal 210; and, consequently, the positive-going square wave input signals 205 are inverted by the operational amplifier 208 [which has an overall gain of minus one (−1) when the positive lower path input terminal 209 is coupled to ground] so as to provide a series of negative-going square wave output signals 211 from the operational amplifier 208 ranging from zero volts (0 v) to minus five volts (−5 v).

The negative-going square wave pulse signals 211 output from the operational amplifier 208 under these conditions are delivered to a bias insertion network 79' (FIG. 31), and thence via control wire 212a, series current limiting resistor R2, and control wire 212b to the coaxial cable's central conductor 66 and conductor 100 of probe 99. However, because of: i) the presence of the current limiting resistor R2; and ii), the current/voltage characteristics of the diode $D_2$, control wire 212b oscillates between zero volts (0 v) and about minus seven-tenths of a volt (−0.7 v) as indicated at 213 in FIG. 31, thus causing the diode $D_2$ to switch between the open and shorted states as the signal level output from the Diode Drive circuit 200 via the control wire 212a oscillates between zero volts (0 v) and minus five volts (−5 v).

If, on the other hand, the POSITIVE/NEGATIVE Diode Drive Select Switch 89 is turned to the broken line position shown in FIG. 32—i.e., the SELECT POSITIVE Diode Drive position—the transistor switch 206 is turned OFF, causing the operational amplifier 208 to exhibit a gain of plus two (+2) along its lower path via positive input terminal 209, while at the same time, the upper path still amplifies the signal 205 with a gain of minus one (−1). The overall gain of the operational amplifier 208 under these operating conditions is, therefore, plus one (+1). Consequently, the operational amplifier 208 serves to pass the positive-going square wave pulses 205 output from the flipflop 202 as a series of unchanged positive-going square wave pulse signals 214 each ranging from zero volts (0 v) to plus five volts (+5 v). The positive-going square wave output pulse signals 214 are delivered via the bias insertion network 79' (FIG. 31), and thence via control wire 212a and series current limiting resistor R2 to control wire 212b which is coupled to the coaxial cable's central conductor 66 and, therefore, to conductor 100 of probe 99. Because of: i) the effect of current limiting resistor R2; and ii), the current/voltage characteristics of the diode $D_1$, control wire 212b oscillates between zero volts (0 v) and plus seven-tenths of a volt (+0.7 v) as indicated at 215 in FIG. 31, thus causing diode $D_1$ to switch between the open and shorted states as the signal level output from the Diode Drive circuit 200 via control wire 212a oscillates between zero volts (0 v) and plus five volts (+5 v).

Those skilled in the art will appreciate that actuation of the POSITIVE/NEGATIVE Diode Drive Select Switch 89 (FIGS. 31 and 32) can be achieved in any desired fashion. For example, the switch 89 may be operated manually by the operator of the apparatus 180 (FIG. 31). Alternatively, it may be operated electromechanically or by any suitable electronic control circuit (not shown); or, it may be operated by a computer, microprocessor controller or the like (not shown) used to control operation of the entire modified exemplary electronic TDR apparatus 180 embodying features of the present invention.

Having in mind the foregoing description of the operation of the Diode Control Section 181 of the modified exemplary TDR apparatus 180 as depicted in FIGS. 31 and 32, and having an understanding that such circuitry serves to pass a series of either negative-going square wave pulses 213 or positive-going square wave pulses 215 to the probe 99 (FIG. 31) via the bias insertion network 79' and control wire 212b for purposes of selectively switching the diodes $D_1$, $D_2$ between the open and shorted states, the overall operation of the modified exemplary TDR system 180 employing synchronous detection will now be described. As the ensuing description proceeds, it will be understood that the positive-going square wave pulses 214 ranging from zero volts (0 v) to plus five volts (+5 v) are used for the purpose of switching the diode $D_1$ between the open state—e.g., when the signal level of the train of pulses 214 output from the Diode Drive circuit 200 shown in FIG. 32 is, at a given point in time, zero volts (0 v) and, therefore, the signal level on control wire 212b is also zero volts (0 v)—and the shorted state—e.g., when the signal level of the train of pulses 214 output from the Diode Drive circuit 200 is, at a given point in time, plus five volts (+5 v) and, therefore, the signal level on the control wire 212b is about plus seven-tenths of a volt (+0.7 v) as indicated at 215 in FIG. 31.

Similarly, the negative-going square wave pulses 211 ranging from zero volts (0 v) to minus five volts (−5 v) are used to switch the diode $D_2$ between the open state—e.g., when the signal level of the train of pulses 211 output from the Diode Drive circuit 200 is, at a given point in time, zero volts (0 v) and, therefore, the signal level on control wire 212b is also at zero volts (0 v)—and the shorted state—e.g., when the signal level of the train of pulses 211 is, at a given point in time, minus five volts (−5 v) and, therefore, the signal level on the control wire 212b is about minus seven-tenths of a volt (−0.7 v) as indicated at 213 in FIG. 31.

In operation, the Repetition Rate Generator 189 and Pulse Generator 184 (FIG. 31) serve to generate a series of fast rise time step pulses (200 to 500 picoseconds) at a constant repetition rate which are propagated down the coaxial cable 54 and along the transmission line probe 99 extending through the soil or other material to be analyzed. Such pulses produce, in the manner previously described, reflections from, for example, the air/probe interface, the end of the probe, discontinuities created when the diodes $D_1$, $D_2$ are shorted, and/or other discontinuities in, for example, the moisture characteristics of the material undergoing test, which reflections travel up the coaxial cable 54 and are continuously sampled by the Sample-And-Hold circuit 185.

Once again, typical waveforms that are observable at the input of the Sample-And-Hold circuit 185 when using, for example, a 10,000 megacycle bandwidth oscilloscope (not shown) are depicted in FIGS. 5, 5A and 5B. Thus, assuming both diodes $D_1$, $D_2$ are open—i.e., that the signal level output from the Diode Control Section 181 is momentarily at zero volts (0 v)—the reflections from the fast rise time pulses propagated down the coaxial cable/transmission line probe 54/99 by the Pulse Generator 184 will produce a waveform such as that shown by way of example at 75 in FIG. 5. On the other hand, when diode $D_1$ is shorted—i.e., when the signal level of the pulses output from the Diode Control Section 181 is at plus five volts (+5 v) and the signal level on control wire 212b is at plus seven-tenths of a volt (+0.7 v)—the waveform 75 will exhibit a steep negative-going ramp 75a at time $T_1$ as shown in FIG. 5A; and, when diode $D_2$ is shorted—i.e., when the signal level of the pulse output from the Diode Control Section 181 is at minus five volts (−5 v) and the signal level on control wire 212b is at minus seven-tenths of a volt (−0.7 v)—the waveform 75 exhibits a steep negative-going ramp 75b at time $T_2$ as shown in FIG. 5B.

Due to the operation of the Diode Drive circuit 200, the amplitude of the reflection sampled by the Sample-And-Hold circuit 185 at time $T_n$ repetitively alternates between the diode-open reflection 75 as shown in FIG. 5 and the diode shorted wave form 75a or 75b as shown in FIGS. 5A or 5B. Thus, the output from the Sample-And-Hold circuit 185 comprises a square wave pulse 216 wherein the frequency of the square wave is one-half (½) the frequency of the square wave pulses 204 output from the Repetition Rate Generator 189; while the amplitude of the square wave pulse 216 is proportional to the difference between the amplitude of the output from the Sample-And-Hold circuit 185 arising from the diode-open reflection at time T and the amplitude of the Sample-And-Hold circuit output arising from the diode shorted reflection at time T. The square wave signal 216 output from the Sample-And-Hold circuit 185 tends to be weak and, moreover, tends to be somewhat obscured by switching transients and other undesirable noise. Accordingly, the signal is passed through AC Amplifier 190, Filter 191 and AC Amplifier 192, with Filter 191 serving to remove large transients and some noise, and thus improving the signal-to-noise ratio. The AC Amplifier 192 removes any DC component from the signal.

The thus amplified and filtered noisy square wave signal 217 output from AC Amplifier 192 is then passed to the Analog Multiplier 194. The second input to the Analog Multiplier 194 is the one-half (½) rate square wave pulse 205 output from the Divide-By-Two circuit 201 which has been passed through the Delay circuit 196 and is output from the AC coupled Buffer Amplifier 198, which serves to remove the DC component, as a positive-going square wave pulse 218. The signal 218 is commonly known by persons skilled in the art as the "Synchronous Detector Reference Signal". The frequency of the Synchronous Detector Reference Signal 218 is identical to the frequency of the noisy square wave signal 217 output from AC Amplifier 192. The polarity of the AC coupled Buffer Amplifier 198 and the Delay characteristics of the Delay circuit 196 are arranged so that the two input signals 217, 218 to the Analog Multiplier 194 are in phase.

The Analog Multiplier 194 and the Low Pass Filter 195 act like an ideal filter/detector, converting the amplitude of the noisy square wave signal 217 input to the Analog Multiplier 194 into a DC output signal V(T) representative of the difference function indicated in FIG. 6 as the positive-going ramps 90, 91 respectively located at points $T_1$ (when diode $D_1$ is alternately shorted and opened) and $T_2$ (when diode $D_2$ is alternately shorted and opened). The Analog Multiplier 194 and Low Pass Filter 195 also further improve the signal-to-noise ratio. The amount of signal-to-noise ratio improvement is proportional to the smoothing (integration) time of the Low Pass Filter 195. The Low Pass Filter integration time is typically set to equal fifty (50) to two hundred (200) full cycles of the noisy square wave pulse 217.

It will be recognized by those skilled in the art that the output of the Sample-And-Hold circuit 185 may actually be a drooping square wave due to the discharge characteristics of the hold capacitor (not shown) within the Sample-And-Hold circuit 185. In this case, the Filter 191 may be advantageously replaced with a second Sample-And-Hold circuit (not shown) to convert the signal from a drooping square wave into a true square wave 217.

The Synchronous Detection System hereinabove described in connection with FIG. 31 can also be advantageously used with probes which do not have remote shorting capability such, for example, as a probe similar to the probe 99 depicted in FIGS. 11, 12 and 31, but which is not provided with the remotely operable active shorting diodes $D_1$ and/or $D_2$; or, alternatively, with probes having only a single shorting diode $D_1$ adjacent the coaxial cable/probe interface 54/92', 54/94' such as shown in FIGS. 9 and 10. Such an arrangement is particularly advantageous with relatively homogeneous soils of the type found in seedling nurseries where the natural reflection from the end of the transmission line/probe at time $T_2$ is typically large and free from distortion.

To this end, when operation in a time delay modulation mode is desired, as contrasted with remotely shortable diode ON/OFF modulation as previously described, it is merely necessary to insure that control wire 212a is grounded, thereby precluding remote switching of either diode $D_1$ or $D_2$. To accomplish this, a Diode ON/OFF Modulation/Time Delay Modulation switch 219 (FIG. 31) is shifted from the solid line Diode ON/OFF Modulation position shown in the drawing to the broken line Time Delay Modulation position, thereby disrupting the flow of negative-going/positive-going pulses 211/214 and coupling control wire 212a to ground. At the same time, the Variable Delay circuit 186 (FIG. 31) in the RF section 182 of the exemplary TDR apparatus 180 is alternated—using any suitable and conventional electronic or computer control circuit (not shown) to provide a suitable time delay modulation input at 199 capable of switching between two preset time delay circuits (not shown) contained within the Variable Delay circuit 186—between first and second preset time delays $T_A$ and $T_B$ at one-half (½) the repetition rate established by the Repetition Rate Generator 189 where:

$$T = \frac{T_A + B_B}{2} ; \qquad [3]$$

and, $$r = T_B - T_A, \qquad [4]$$

where "r" is the approximate rise time of the reflected pulse.

The foregoing arrangement, which has been depicted graphically in FIGS. 33 and 34, generates a square wave 216 at the output of the Sample-And-Hold circuit 185 whose amplitude is proportional to the slope of the reflection, thereby reducing background noise and allowing improved detection of the normally distinctive steep natural reflection from the end of the probe. Such a method, in effect, "differentiates" the reflected waveform prior to amplification and filtering in the Synchronous Detection Section 188 of the modified exemplary electronic TDR apparatus 180.

The foregoing synchronous detection technique is of economic and practical importance since a TDR instrument 180 employing an RF Section 182 and a Synchronous Detection Section 188—irrespective of whether a Diode Control Section 181 is or is not present, or is or is not being utilized—can be effectively used with probes having natural or passive reflective elements and wherein synchronous detection is necessary for the remotely shorting diodes or similar active elements. More specifically, this embodiment of the invention permits a single electronic design—such as the modified exemplary TDR system 180 embodying features of the present invention as depicted in FIG. 31—to measure time delays for any active or passive reflective element in a TDR system by using either: i) remotely shortable diode ON/OFF modulation; or ii), time delay modulation.

In accordance with yet another of the important objectives of the present invention, provision is made for designing probes having multiple pairs of serially arranged, remotely operable, oppositely directed, variable impedance devices— such, for example, as PIN diodes or the like—so as to form a multi-segment probe wherein each pair of oppositely directed diodes defines the boundaries of adjacent segments on the probe. To this end, and as best illustrated in FIG. 35, a multi-segment bayonet-type probe, generally indicated at 220, has been depicted having a pair of flat, elongate, parallel, spaced conductors 221, 222 each having a rectangular cross section, with the conductors being spaced apart by, and integrally bonded to, an internal or central nonconductive dielectric spacer 224.

In this instance three (3) pairs of oppositely directed, normally open, remotely operable PIN diodes—viz., diode pair $D_1/D_2$; diode pair $D_3/D_4$; and, diode pair $D_5/D_6$—or other suitable remotely operable, active variable impedance devices are imbedded in the dielectric spacer 224 at generally equally spaced points along the length thereof (those skilled in the art will, however, appreciate that the diode pairs can be unequally spaced if desired), with each diode being coupled to the probe conductors 221, 222. Referring to FIG. 35, it will be noted that diodes $D_1$, $D_2$ defining diode pair $D_1/D_2$ and diodes $D_3$, $D_4$ defining diode pair $D_3/D_4$ are all electrically coupled to probe conductors 221, 222 utilizing RF coupling networks defined by resistors R and capacitors C, whereas diodes $D_5$, $D_6$ defining diode pair $D_5/D_6$ are electrically coupled directly to the probe conductors 221, 222 without employment of RF coupling networks and in precisely the same manner as previously described in connection with FIGS. 13 through 17.

As in the case of some of the probes previously described herein—for example, probe 99 depicted in FIGS. 11 through 17, probe 115 depicted in FIG. 20, and probe 126 depicted in FIG. 25—the internal dielectric spacer 224 is preferably provided with a relatively sharp pointed probe end 225 so as to facilitate insertion of the probe 220 into the soil or other test medium without significant disturbance thereof.

Prior to pouring of the liquid dielectric material into the space intermediate the spaced parallel conductors 221, 222, diode pairs $D_1/D_2$ and $D_3/D_4$, together with their RF coupling networks defined by resistors R and capacitors C, and diode pair $D_5/D_6$, are preferably mounted on small circuit boards (not shown, but similar to the circuit boards 111 depicted in FIGS. 13, 16 and 17); and, are properly positioned between the probe conductors 221, 222 and electrically coupled thereto in the manner previously described in connection with the probe 99 depicted in FIGS. 13 through 17. In this instance, however, diode pairs $D_1/D_2$ and $D_3/D_4$ and their associated RF coupling networks are each electrically coupled to a separate control wire—e.g., the pair of diodes $D_1/D_2$ and their associated RF coupling networks defined by resistors R and capacitors C are electrically coupled to a control wire 226 terminating at terminal 228 external to the probe 220; while the pair of diodes $D_3/D_4$ and their associated RF coupling networks are electrically coupled to a second separate and independent control wire 229 terminating at terminal 230 external to the probe 220.

In keeping with this aspect of the invention, each of the resistors R are coupled in parallel with respective different ones of the variable impedance devices—i.e., the diodes $D_1$ . . . $D_4$ between probe conductor 221 and the one of the control wires 226, 229 associated therewith for discharging any residual charge on the variable impedance devices when switched to the open state. Each of the capacitors C are connected in series between respective different ones of the variable impedance devices $D_1$ . . . $D_4$ and probe conductor 222 so as to provide a high frequency short circuit therebetween. Thus, each variable impedance device $D_1$ . . . $D_4$ is AC-coupled to the probe conductors 221, 222 through its associated series connected capacitor C.

As the ensuing description proceeds, it will become evident to persons skilled in the art that a multi-segment probe embodying features of the present invention and of the type depicted in FIG. 35 is not limited to any particular probe conductor structure—e.g., the probe conductors need not be formed of barstock of rectangular cross section—nor are such probes limited to use with three (3) pairs of variable impedance devices defining a three-segment probe. Rather, multi-segment probes made in accordance with the present invention can employ two, three, four or more pairs of longitudinally spaced, oppositely directed diodes or other variable impedance devices provided only that a separate control wire is provided for at least the second, third and each additional pair of diodes $D_1/D_2$ . . . $D_{n-3}/D_{n-2}$. Alternatively, and although not shown in the drawings, all of the diode pairs, including diode pair $D_5/D_6$, may be provided with separate control wires and employ RF coupling networks defined by resistors R and capacitors C—a configuration found particularly advantageous when the probe is intended for use in saline soils.

Once the pairs of diodes $D_1/D_2$ . . . $D_{n-1}/D_n$ (where "n" is any whole even integer equal to or greater than "4"—e.g., "n" is equal to "4", "6", "8", etc.), RF coupling networks for the second and each additional pair of diodes, and control wires 226, 229 for the second and each additional pair of diodes, are properly positioned intermediate the probe conductors 221, 222 and electrically bonded thereto, the liquid dielectric material is poured into the cavity therebetween utilizing any desired bonding technique such, for example, as one of those described previously in connection with FIGS. 13 through 17 or FIG. 18. After the dielectric material has set, hardened and cured, the diodes $D_1$ through $D_6$, RF coupling networks defined by resistors R and capacitors C, and control wires 226, 229 are firmly imbedded within, and protected by, the dielectric spacer material 224; with the control wires 226, 229 respectively terminating external to the probe at terminals 228, 230.

Figure 36A:
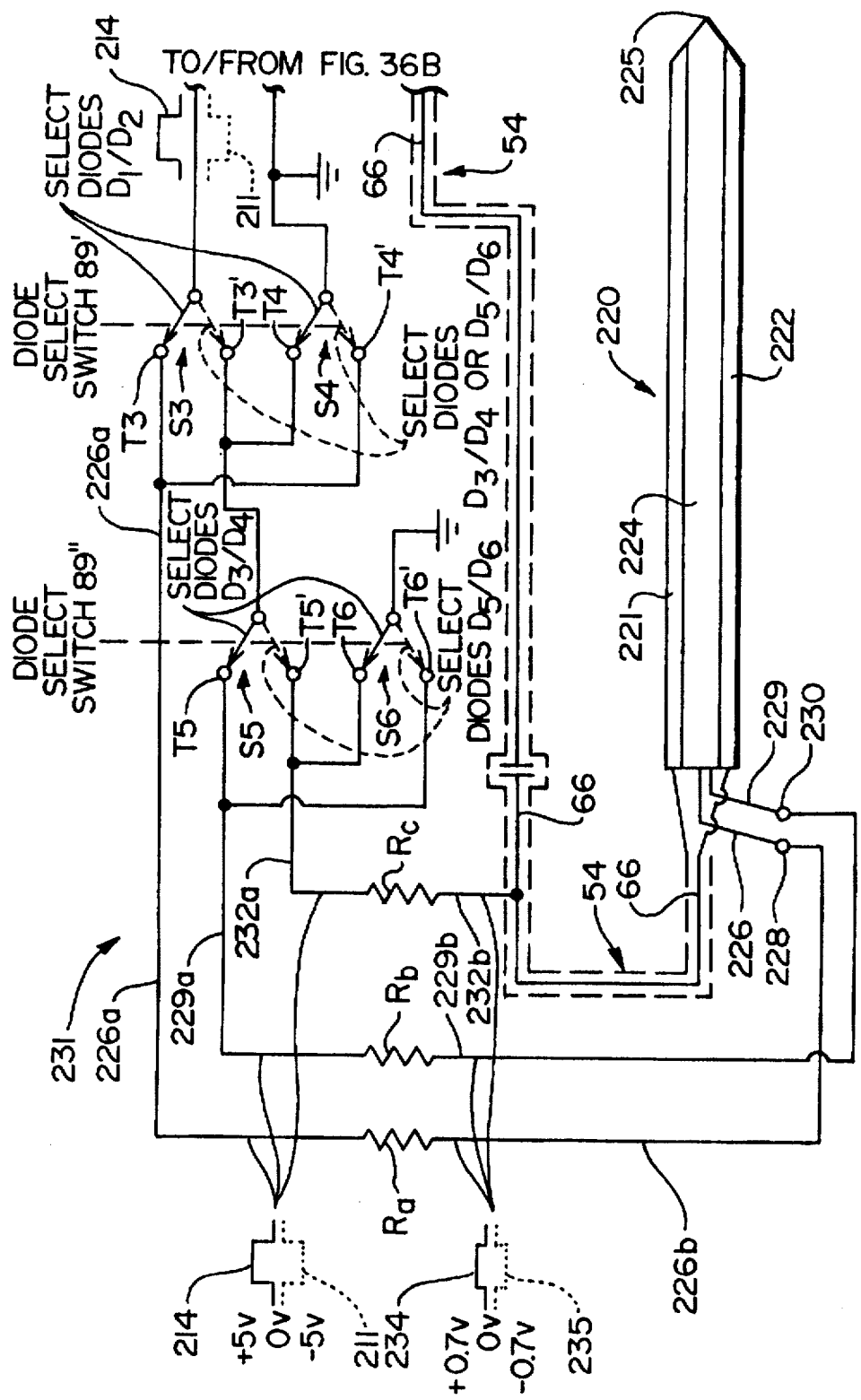

In carrying out this aspect of the invention, the exemplary multi-segment stripline probe 220 depicted in FIG. 35 is coupled to any suitable TDR instrument—for example, the conventional TDR instrument 51 depicted in FIG. 4 or the modified exemplary TDR instrument 180 depicted in FIG. 31 which embodies features of the present invention—by means of: i) a coaxial cable 54; and ii), a modified bias insertion network such as that shown generally at 231 in FIG. 36A. For convenience, the probe 220 is here shown coupled to a TDR instrument 180 (FIG. 36B) which is identical in construction and mode of operation to the TDR instrument 180 previously described in connection with FIG. 31.

In this instance, however, the POSITIVE/NEGATIVE Diode Drive Selector Switch 89 (FIGS. 32 and 36B) does not serve to select any specific diode but, rather, it serves to select either POSITIVE diodes $D_1$, $D_3$, $D_5$ or NEGATIVE diodes $D_2$, $D_4$, $D_6$—i.e., POSITIVE diodes $D_1$, $D_3$, $D_5$ comprising odd numbered diodes which are forward biased into conduction when a positive voltage is impressed on the conductors 222, 226 or 229; and, NEGATIVE diodes $D_2$, $D_4$, $D_6$ comprising even numbered diodes which are forward biased into conduction by impressing a negative voltage on the conductors 222, 226, 229. When the NEGATIVE diodes are selected, the POSITIVE/NEGATIVE Diode Drive Select Switch 89 is positioned in the solid line position shown in FIG. 32, thereby enabling generation of negative-going square wave output pulses 211 from the Diode Control Section 181 in the manner previously described for enabling selective activation of one of the NEGATIVE diodes $D_2$, $D_4$, or $D_6$; whereas, when the switch 89 is positioned in the broken line position shown in FIG. 32, positive-going square wave output pulses 214 are output from the Diode Control Section 181 for enabling selective actuation of one of the POSITIVE diodes $D_1$, $D_3$, or $D_5$.

Referring next to FIG. 36A, it will be noted that the exemplary bias insertion network 231 includes: i) a first Diode Select Switch 89' which is coupled to a first pair of ganged switches S3 (for selecting either diode pair $D_1/D_2$ or one of diode pairs $D_3/D_4$ or $D_5/D_6$) and S4 (for grounding either diode pair $D_1/D_2$ or one of diode pairs $D_3/D_4$ or $D_5/D_6$); and ii), a second Diode Select Switch 89" coupled to a second pair of ganged switches $S_5$ (for selecting either diode pair $D_3/D_4$ or diode pair $D_5/D_6$) and $S_6$ (for grounding either diode pair $D_3/D_4$ or diode pair $D_5/D_6$). Terminals T3 and T4' of switches S3 and S4, respectively, are coupled via control wire 226a, current limiting resistor $R_a$, and control wire 226b to control wire 226 associated with diode pair $D_1/D_2$ in probe 220; while terminals T5 and T6' of switches S5 and S6, respectively, are coupled via control wire 229a, to current limiting resistor $R_b$, and control wire 229b to control wire 229 associated with diode pair $D_3/D_4$.

Thus, the arrangement is such that in operation—and, assuming: i) that the POSITIVE/NEGATIVE Diode Drive select Switch 89 (FIGS. 32 and 36B) is positioned to select one of the POSITIVE diodes $D_1$, $D_3$ or $D_5$ (i.e., assuming that the switch 89 is in the broken line position shown in FIG. 32 so as to cause output of positive-going square wave output pulses 214 from the Diode Control Section 181 of the TDR instrument 180); and ii), that the Diode Select Switches 89', 89" (FIG. 36A) are in the solid line positions shown in the drawing—the circuitry will be initially configured to cause diode $D_1$ to alternate between the open and shorted states while all other diodes $D_2$ through $D_6$ remain open. This is due to the fact that the positive-going square wave pulses 214 output from the Diode Control Section 181 of the TDR instrument 180 (FIG. 36B) are conveyed via switch S3, its terminal T3, control wire 226a, and current limiting resistor $R_a$, to control wire 226b and thence to terminal 228 and control wire 226; while control wires 229a and 229b and, therefore, 229 are grounded via switch/terminal S4/T4, switch/terminal S5/T5 and current limiting resistor $R_b$. At the same time, the central conductor 66 of the coaxial cable 54, which is coupled to probe conductor 222, is also coupled to ground via switch/terminal S6/T6, control wire 232a, current limiting resistor $R_c$, and control wire 232b. Since control wires 229, 229a, 229b and control wires 232a, 232b are grounded, pulses output from the Diode Control Section 181 (FIG. 36B)—whether positive-going pulses 214 or negative-going pulses 211—are incapable of biasing any of diodes $D_3$ through $D_6$ into conduction and, consequently, diodes $D_3$ through $D_6$ remain open.

As the positive-going square wave pulses 214 output from the Diode Control Section 181 (FIG. 36B) travel down the control wire 226a (FIG. 36A), the signal level on the control wire 226a oscillates between zero volts (0 v) and about plus five volts (+5 v). However, because of: i) the effect of current limiting resistor $R_a$; and ii), the current/voltage characteristics of the diode $D_1$, the signal level on control wire 226b, and, therefore, on control wire 226, oscillates between zero volts (0 v) and about plus seven-tenths of a volt (+0.7 v) as indicated at 234 in FIG. 36A, causing POSITIVE diode $D_1$ to switch between the open state when the signal level on the control wire 226a is zero volts (0 v) and the shorted state when the signal level on the control wire 226a is plus five volts (+5 v). At the same time, the plus seven-tenths of a volt (+0.7 v) signal level produced on the control wire 226 is incapable of biasing NEGATIVE diode $D_2$ into conduction; and, therefore, NEGATIVE diode $D_2$ remains open.

Assuming next that the Diode Select Switches 89', 89" (FIG. 36A) remain in the solid line position shown, but that the POSITIVE/NEGATIVE Diode Drive Select Switch 89 (FIGS. 32 and 36B) is shifted to the solid line position shown in FIG. 32, the Diode Drive circuit 200 is now configured so as to output a series of negative-going square wave pulses 211 from the Diode Control Section 181 of the TDR instrument 180. Since Diode Select Switches 89', 89" remain unchanged, control wires 229a, 229b and 229, as well as control wires 232a and 232b all remain grounded; and, consequently, diodes $D_3$ through $D_6$ remain open. However, under these operating conditions, the negative-going square wave pulses 211 carried on control wire 226a via switch/terminal S3/T3 cause the signal level on control wire 226a to oscillate between zero volts (0 v) and minus five volts (−5 v). When the signal level on control wire 226a is zero volts (0 v), both diodes $D_1$ and $D_2$ remain open; but, when the signal level on control wire 226a is lowered to minus five volts (−5 v), the current limiting resistor $R_a$ causes the voltage level on control wires 226b and 226 to be reduced to about minus seven-tenths of a volt (−0.7 v) as indicated at 235 in FIG. 36B, which serves to forward bias NEGATIVE diode $D_2$ into conduction, shorting the probe conductors 221, 222 at the position of diode $D_2$. POSITIVE diode $D_1$, however, remains open since a minus seven-tenths of a volt (−0.7 v) signal level on control wire 226 is incapable of biasing the oppositely directed POSITIVE diode $D_1$ into conduction.

Figure 36B:
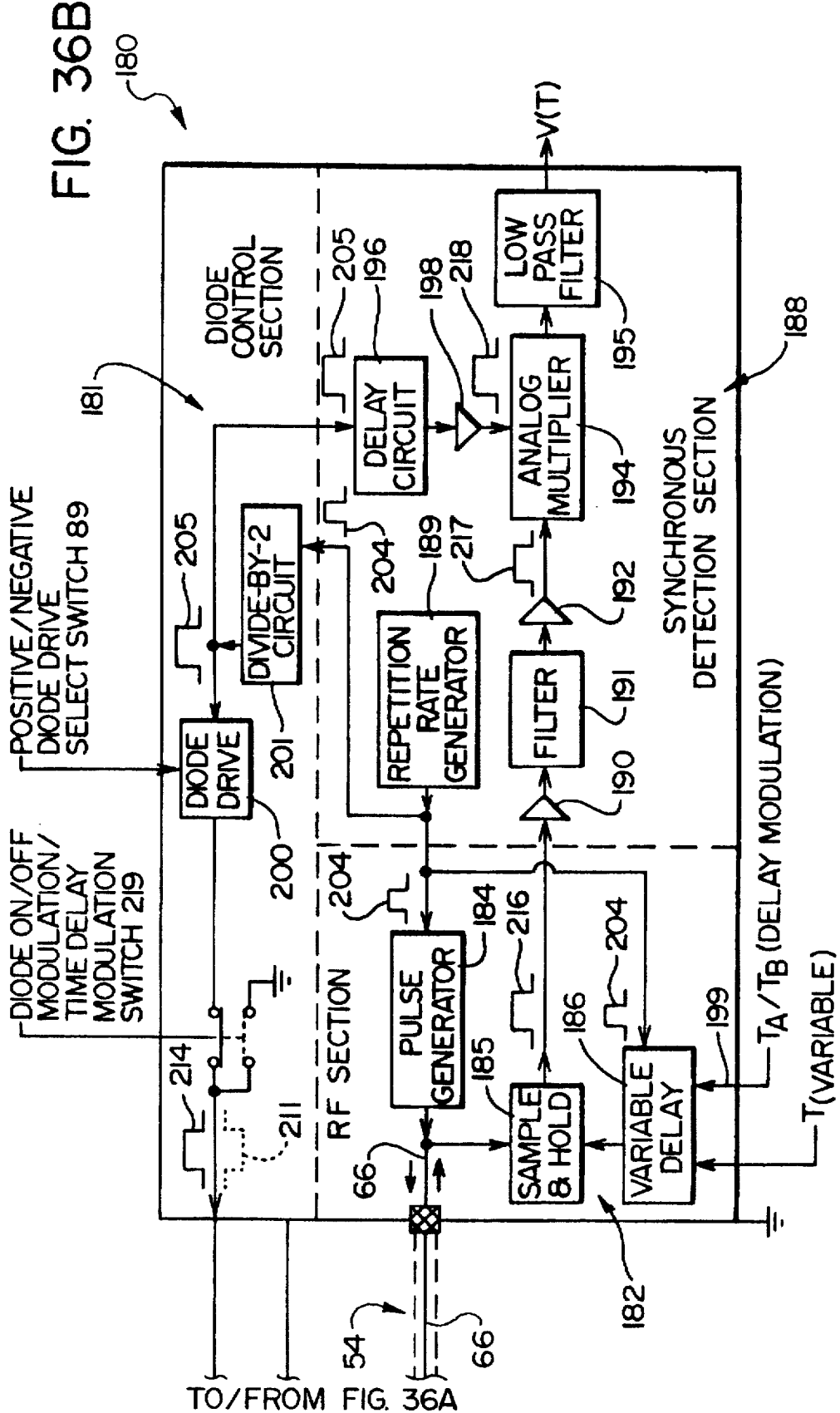

Assuming next that: i) the POSITIVE/NEGATIVE Diode Drive Select Switch 89 (FIGS. 32 and 36B) is in the broken line position shown in FIG. 32 configuring the Diode Drive circuit 200 to output a series of positive-going square wave pulses 214; ii) Diode Select Switch 89' (FIG. 36A) is switched to the broken line position shown in the drawing; and iii), Diode Select Switch 89" (FIG. 36A) remains in the solid line position shown, the circuitry of FIGS. 36A and 36B will be configured to switch diode $D_3$ between the open and shorted states. More specifically, under these conditions: a) control wire 226a is coupled to ground via switch/terminal S4/T4', thus coupling control wire 226b via current limiting resistor $R_a$ and control wire 226 to ground so as to preclude biasing of diodes $D_1/D_2$ into conduction; b) control wire 229a is coupled directly to the output from the Diode Control Section 181 (FIG. 36B) of the TDR instrument 180 via switch/terminal S3/T3' and switch/terminal S5/T5; and, consequently, as the voltage level on control wire 229a oscillates between zero volts (0 v) and plus five volts (+5 v), the voltage level on control wires 229b and 229 will, due to: i) the effect of current limiting resistor $R_b$; and ii), the current/voltage characteristics of the diode $D_3$, oscillate between zero volts (0 v) and about plus seven-tenths of a volt (+0.7 v) as indicated at 234, thus permitting switching of the diode $D_3$ dependent solely upon the position of the POSITIVE/NEGATIVE Diode Drive Select Switch 89 (FIGS. 32 and 36A) which is here assumed to be in the broken line position shown in FIG. 32 so as to configure the circuitry to output positive-going square wave pulses 214 from the Diode Control Section 181; and c), control wire 232a remains coupled to ground via switch/terminal S6/T6; and, therefore, control wire 232b is grounded via current limiting resistor $R_c$ so as to preclude biasing of diodes $D_5/D_6$ into conduction which, therefore, remain open.

Under these conditions, and as will be best understood upon reference to FIG. 36a, as the signal level on control wire 229a oscillates between zero volts (0 v) and plus five volts (+5 v), the signal level on control wires 229b and 229 will, due to the effect of current limiting resistor $R_b$ and the current/voltage characteristics of the diode $D_3$, oscillate between zero volts (0 v) and about plus seven-tenths of a volt (+0.7 v); and, therefore, both diodes $D_3$ and $D_4$ remain open whenever the signal level on control wire 229 is at zero volts (0 v); but, when the signal level on control wire 229 is at plus seven-tenths of a volt (+0.7 v), POSITIVE diode $D_3$ is forward biased into conduction, effectively shorting the probe conductors 221, 222 at the diode $D_3$ position. However, NEGATIVE diode $D_4$ remains open since a plus seven-tenths of a volt (+0.7 v) signal level on the control wire 229 is incapable of biasing the oppositely directed NEGATIVE diode $D_4$ into conduction.

However, if the POSITIVE/NEGATIVE Diode Drive Select Switch 89 (FIGS. 32 and 36B) is now shifted to the solid line position shown in FIG. 32, the Diode Control Section 181 of the TDR instrument 180 will then be configured to output a series of negative-going square wave pulses 211 to the bias insertion network 231. Assuming further that Diode Select Switch 89' (FIG. 36A) remains in the broken line position shown in the drawing while Diode Select Switch 89" remains in the solid line position shown, the negative-going square wave pulses 211 input to the bias insertion network 231 (FIG. 36A) from the Diode Control Section 181 of the TDR instrument 180 (FIG. 36B) will be propagated down control wire 229a via switch/terminal S3/T3' and switch/terminal S5/T5, causing the signal level on the control wire 229a to oscillate between zero volts (0 v) and minus five volts (−5 v). Consequently, the signal level on control wires 229b and 229 will, because of: i) the effect of current limiting resistor $R_b$; and ii), the current/voltage characteristics of the diode $D_4$, oscillate between zero volts (0 v) and about minus seven-tenths of a volt (−0.7 v) as indicated at 235 in FIG. 36A. When the signal level on the control wire 229 is at zero volts (0 v), both diodes $D_3$ and $D_4$ remain open; but, when the signal level on the control wire 229 is lowered to minus seven-tenths of a volt (−0.7 v), NEGATIVE diode $D_4$ is forward biased into conduction, effectively shorting the probe conductors 221, 222 at the diode $D_4$ position. POSITIVE diode $D_3$, however, remains open since a minus seven-tenths of a volt (−0.7 v) signal level on the control wire 229 is incapable of biasing the oppositely directed POSITIVE diode $D_3$ into conduction.

Assuming next that both Diode Select Switches 89' and 89" are shifted to the broken line positions shown in FIG. 36A, it will be noted that control wire 226a remains coupled to ground via switch/terminal S4/T4' and, consequently, control wires 226b and 226, which are coupled to the grounded control wire 226a via current limiting resistor $R_a$, remain grounded, thereby insuring that diodes $D_1$, $D_2$ remain open. However, control wire 229a is now coupled to ground via switch/terminal S6/T6', thereby insuring that diodes $D_3$, $D_4$ which are coupled to grounded control wire 229a via current limiting resistor $R_b$ and control wires 229b and 229, remain open. Consequently, dependent only upon the position of the POSITIVE/NEGATIVE Diode Drive Select Switch 89 (FIGS. 32 and 36B), one of the diodes $D_5/D_6$ will be switched between the open and shorted states since the central conductor 66 of the coaxial cable 54 will now be directly coupled to the Diode Control Section 181 of the TDR instrument 180 (FIG. 36B) via switch/terminal S3/T3', switch/terminal S5/T5', control wire 232a, current limiting resistor $R_c$, and control wire 232b.

Assuming the POSITIVE/NEGATIVE Diode Drive Select Switch 89 is in the broken line position shown in FIG. 32, the Diode Drive Circuit 200 will be configured to output positive-going square wave pulses 214 from the Diode Control Section 181 of the TDR instrument 180; and, consequently, the signal level on control wire 232a will oscillate between zero volts (0 v) and plus five volts (+5 v), while the signal level on control wire 232b will, because of: i) the current limiting resistor $R_c$; and ii), the current/voltage characteristics of the diode $D_5$, oscillate between zero volts (0 v) and about plus seven-tenths of a volt (+0.7 v) as indicated at 234 in FIG. 36A. When the sisal level on control wire 232b is at zero volts (0 v), both diodes $D_5$ and $D_6$ remain open; but, when the signal level on control wire 232b rises to plus seven-tenths of a volt (+0.7 v), POSITIVE diode $D_5$ is forward biased into conduction, effectively shorting the probe conductors 221, 222 at the diode $D_5$ position. However, oppositely directed NEGATIVE diode $D_6$ remains open since a plus seven-tenths of a volt (+0.7 v) signal level on conductor 222 is incapable of biasing NEGATIVE diode $D_6$ into conduction.

Finally, assuming that the POSITIVE/NEGATIVE Diode Drive Select Switch 89 is shifted to the solid line position shown in FIG. 32, the Diode Drive circuitry 200 is configured to output negative-going square wave pulses 211 from the Diode Control Section 181 of the TDR instrument 180; and, under these conditions, such negative-going square wave pulses 211 are conveyed via switch/terminal S3/T3' and switch/terminal S5/T5' to control wire 232a, causing the latter to oscillate between zero volts (0 v) and minus five volts (−5 v). Consequently, because of: i) the current limiting resistor $R_c$; and ii), the current/voltage characteristics of diode $D_6$, the signal level on control wire 232b will oscillate between zero volts (0 v) and about minus seven-tenths of a volt (−0.7 v) as indicated at 235 in FIG. 36A. When the signal level on control wire 232b is zero volts (0 v), both diodes $D_5$, $D_6$ (FIG. 35) remain open; but, when the signal level on control wire 232b is at about minus seven-tenths of a volt (−0.7 v), NEGATIVE diode $D_6$ is forward biased into conduction, effectively shorting probe conductors 221, 222 at the diode $D_6$ position while oppositely directed POSITIVE diode $D_5$, which cannot be biased into conduction by a negative-going pulse, remains open.

As thus far described, it will be appreciated that the exemplary multi-segment probe 220 depicted in FIG. 35 can be operated as a 3-segment probe employing three (3) diode pairs—viz., diode pair $D_1/D_2$ defining a first segment extending from the diode $D_1$ location to the diode $D_2$ location; diode pair $D_3/D_4$ defining a second segment extending from the diode $D_3$ location to the diode $D_4$ location; and, diode pair $D_5/D_6$ (i.e., diode pair $D_{n-1}/D_n$ where "n" is equal to "6") defining a third segment extending from the diode $D_3$ location to the diode $D_6$ location. It will further be appreciated from the foregoing description that operation of the TDR apparatus 180 (FIGS. 36A and 36B) using such a probe 220 serves to generate six (6) precise, unambiguous timing markers $T_1, T_2 \ldots T_6$ at the six (6) spaced locations of respective ones of diodes $D_1, D_2 \ldots D_6$.

However, since six (6) precise, unambiguous timing markers $T_1, T_2 \ldots T_6$ are generated at six (6) spaced locations, those skilled in the art will appreciate that the multi-segment probe 220 depicted in FIG. 35 can, where desired, actually be operated as 5-segment probe—viz., i) a first segment defined by, and spanning the space between, diodes $D_1$ and $D_2$; ii) a second segment defined by, and spanning the space between, diodes $D_2$ and $D_3$; iii) a third segment defined by, and spanning the space between, diodes $D_3$ and $D_4$; iv) a fourth segment defined by, and spanning the space between, diodes $D_4$ and $D_5$; and v), a fifth segment defined by, and spanning the space between, diodes $D_5$ and $D_6$.

When operating the multi-segment probe 220 (FIGS. 35 and 36A) as a 5-segment probe, it is merely necessary to: i) rapidly and repeatedly open and short diode $D_1$ by impressing a positive voltage level on control wires 226a, 226b and 226 to establish a first timing marker $T_1$ in the manner previously described; ii) rapidly and repeatedly open and short diode $D_2$ by impressing a negative voltage level on the control wires 226a, 226b and 226 to establish a second timing marker $T_2$; iii) process the reflection data sampled at $T_1$ and $T_2$ to determine the time of travel and, therefore, the propagation velocity of energy pulses traveling along the first segment defined by diodes $D_1$ and $D_2$; iv) rapidly and repeatedly open and short diode $D_3$ by impression of a positive voltage level on control wires 229a, 229b and 229 to establish a third timing marker $T_3$; and v), process the reflection data sampled at $T_2$ and $T_3$ to determine the time of travel and, therefore, the propagation velocity of energy pulses traveling along the second segment of the probe defined by diodes $D_2$ and $D_3$.

The foregoing process steps are then repeated to rapidly open and short diode $D_4$ using a negative voltage level impressed on control wires 229a, 229b and 229 to determine $T_4$ and, thereafter, processing the reflection data sampled at timing markers $T_3$ and $T_4$ to determine the propagation velocity of energy pulses traveling along the third probe segment defined by diodes $D_3$ and $D_4$. The foregoing process is then followed by repetitive opening and shorting of diode $D_5$ by impression of a positive voltage level on control wires 232a, 232b, 66 and 222 to establish a fifth timing marker $T_5$ and subsequent processing of the reflection data sampled at timing markers $T_4$ and $T_5$ to determine the propagation velocity of energy pulses traveling along the fourth probe segment defined by the diodes $D_4$ and $D_5$. Finally, $D_6$ is measured by impressing a negative voltage level on control wires 232a, 232b, 66 and 222 to rapidly and repeatedly open and short diode $D_6$, with the reflection data sampled at $T_5$ and $T_6$ being processed to determine the propagation velocity of energy pulses traveling along the fifth probe segment defined by diodes $D_5$ and $D_6$.

In short, it will be understood that in its broadest sense, a multi-segment probe 220 such as shown in FIG. 35 can include a plurality of pairs of diodes where the boundary between adjacent segments is defined by a single diode; and, consequently, a multi-segment probe can be defined by diodes $D_1$, $D_2$ ... $D_n$ where "n" is any whole integer equal to or greater than "3". In other words, where "n" is equal to "3", a 2-segment probe is defined by diode pairs $D_1/D_2$, $D_2/D_3$; where "n" is equal to "4", a 3-segment probe is defined by diode pairs $D_1/D_2$, $D_2/D_3$ and $D_3/D_4$; etc.

It will be noted that in the various exemplary probe/coaxial cable arrangements described hereinabove, the coaxial cable 54 has been depicted as being electrically coupled to the probe conductors 62, 64 (FIGS. 4, 7 and 9), 95, 96, 98 (FIGS. 8 and 10), 100, 101 (FIGS. 11 and 31) and 221, 222 (FIGS. 35 and 36A) adjacent the proximal ends of the probe conductors—i.e., adjacent the air/probe interface. However, the invention is not limited to such an arrangement. To the contrary, and although not shown in the drawings, those skilled in the art will appreciate that the coaxial cable 54 can extend longitudinally along the probe conductors and be electrically coupled thereto at any desired point intermediate the proximal and distal ends of the probe conductors provided only that a remotely operable, normally open, variable impedance device is coupled across the probe conductors adjacent the coaxial cable/probe conductor interface for establishing a precise, unambiguous timing marker T at that interface.

For example, when dealing with saline soils—indeed, even moderately saline soils—it has been found that excellent results can be achieved where the coaxial cable 54 comprises a thin coaxial cable (such, for example, as a type RG-174 coaxial cable) which is electrically coupled to the probe conductors at a point approximately midway between the proximal and distal ends of the probe conductors and wherein a suitable remotely operable, normally open, variable impedance device is coupled across the probe conductors at the interface between the coaxial cable and the probe conductors. Such an arrangement insures that fast rise time pulses propagated along the probe conductors from the coaxial cable/probe conductor interface towards the variable impedance devices located adjacent the probe's proximal and distal ends need travel only one-half (½) the effective length of the probe as contrasted with the full effective length of the probe where the coaxial cable is coupled to the probe's proximal end.

Those skilled in the art will appreciate that the particular means provided for shifting the POSITIVE/NEGATIVE Diode Drive Select Switch 89 (FIGS. 32 and 36B) and the Diode Select Switches 89', 89" (FIG. 36A) from one position to another form no part of the present invention and are well within the capability of persons skilled in the art relating to electronic circuit design. Thus, such switches may, if desired, be manually and independently controlled by the operator of the TDR system 180. Alternatively, the switches may be electro-mechanically or electronically controlled by any suitable control circuit (not shown). Preferably, however, the entire TDR system 180 will be computer controlled; and, in this type of system: i) the POSITIVE/NEGATIVE Diode Drive Select Switch 89 (FIGS. 32 and 36B); ii) the Diode Select Switches 89', 89" (FIG. 36A); iii) the input T to the Variable Delay circuit 186 in the RF section 182 (FIG. 36B) of the TDR instrument 180; iv) the Diode ON/OFF Modulation/Time Delay Modulation switch 219; and v), the Delay Modulation input 199 when the TDR system 180 is being operated in the time delay modulation mode rather than in the remotely shortable diode ON/OFF modulation mode, will all be controlled by one or more suitable microprocessor chips in an overall computer control system (not shown). Moreover, in such an overall computerized control system, the output V(T) from the Low Pass Filter 195 (FIG. 36B) will preferably be sampled by an Analog-To-Digital converter (not shown) and input to the computer control.

It will be appreciated from the foregoing description relating to FIGS. 35, 36A and 36B that there has herein been described a simple, yet highly effective, multi-segment, bayonet-type or stripline probe 220 (FIG. 35) and control system therefor (FIGS. 32, 36A and 36B) capable of selectively switching the diodes in multiple adjacent pairs of diodes $D_1/D_2$ ... $D_{n-1}/D_n$, one diode at a time, between open and shorted states, so as to permit remotely operated ON/OFF diode modulation in any selected one of multiple adjacent lineal segments of the probe 220. Such a probe has proved highly effective to measure water content and/or moisture characteristics of the soil or other medium undergoing analysis at different depths along the probe 220. Such an arrangement also permits of ease in measuring the moisture characteristics of the test media in two or more adjacent layers of a layered media. Moreover, multi-segment probes embodying features of the present invention can also be used as depth multiplexers.

In summary, it will be understood by those skilled in the art upon review of the foregoing Specification in the light of the accompanying drawings and the ensuing claims, that there have herein been disclosed a number of methods, probes and circuit embodiments characterized by their simplicity and economy, yet which are highly effective in providing accurate readings of moisture content and the like in soils and a wide range of other test media utilizing either: i) remotely operable ON/OFF variable impedance (e.g. diode) modulation; or ii), time delay modulation. In either case, the arrangement permits of ease of generation and observation of precise, accurate and easily identifiable timing markers at known positions along the length of the probe despite the fact that the signal levels usually encountered are small and normally at least partially obscured by unwanted background noise levels. The invention may be readily employed with 2-rod, 3-rod and/or other multi-rod conventional probes, or with multi-rod probes which may take the form of bayonet-type stripline probes embodying features of the present invention, all as hereinabove described.

I claim:

1. A probe for use with Time Domain Reflectometry apparatus of the type used to measure the moisture content of a material to be tested and employing an RF cable having first and second conductors for coupling said probe to the Time Domain Reflectometry apparatus, said probe comprising, in combination:
   a) a non-conductive base portion;
   b) first conductive means mounted in said base portion and extending laterally at right angles with respect thereto;
   c) second conductive means mounted in said base portion and extending laterally at right angles with respect thereto, said second conductive means being spaced from said first conductive means and extending parallel thereto;
   d) said first and second conductive means defining a multi-conductor probe having an effective length L;
   e) means for coupling said first conductive means to one of the first and second conductors of the RF cable;
   f) means for coupling said second conductive means to the other of the first and second conductors of the RF cable;
   g) means for selectively shorting said first conductive means to said second conductive means at at least one preselected point along the length L of said probe;
   h) means for generating a first TDR reflection plot when said first and second conductive means are electrically isolated one from the other;
   i) means for generating a second TDR reflection plot when said first and second conductive means are shorted one to the other; and,
   j) means for comparing said first and second TDR reflection plots to establish at least one precise and unambiguous timing marker to be used in the measurement of the propagation velocity of a short pulse of energy as it travels along said first and second conductive means when said probe is inserted into the material to be tested.

2. A probe as set forth in claim 1 wherein said first and second conductive means comprise stainless steel rods.

3. A probe as set forth in claim 1 wherein said first conductive means comprises "n" second stainless steel rod (s) wherein "n" is equal to any desired whole integer.

4. A probe as set forth in claim 1 wherein said probe comprises an elongate, unitary, generally imperforate, probe-like instrument having first and second spaced, parallel, conductors respectively defining said first and second conductive means and a central non-conductive dielectric material separating said first and second spaced, parallel, conductors.

5. A probe as set forth in claim 1 wherein said means for comparing said first and second TDR reflection plots comprises waveform subtraction means.

6. A probe as set forth in claims 1, 2, 3, 4 or 5 wherein said means for selectively shorting said first conductive means to said second conductive means comprises at lease one variable impedance device.

7. A probe as set forth in claims 1, 2, 3, 4 or 5 wherein said means for selectively shorting said first conductive means to said second conductive means comprises a pair of variable impedance devices respectively positioned at two (2) spaced selected points defining the effective length L of said probe.

8. A probe as set forth in claim 7 wherein the first of said pair of variable impedance devices is mounted on said probe in proximate relation to said non-conductive base portion for establishing a first selected closed/open circuit adjacent the air/material interface when said probe is inserted into a material to be tested and the second of said pair of variable impedance devices is mounted on said probe in proximate relation to the free ends of said first and second conductive means.

9. A probe as set forth in claims 1, 2, 2, 4, or 5 wherein said means for selectively shorting said first conductive means to said second conductive means includes at east one variable impedance device and remotely operable switch means for selectively biasing said at least one variable impedance device to one of a conductive and non-conductive state.

10. A probe as set forth in claim 9 wherein said remotely operable switch means comprises one of: i) a manually operated switch means; ii) an electromechanically operated switch means; and iii), an electronically operated switch means.

11. A probe as set forth in claims 1, 2, 3, 4 or 5 wherein said means for selectively shorting said first conductive means to said second conductive means comprises at least one diode.

12. A probe as set forth in claims 1, 2, 3, 4 or 5 wherein said means for selectively shorting said first conductive means to said second conductive means comprises a pair of diodes respectively positioned at two (2) spaced selected points defining the effective length L of said probe.

13. A probe as set forth in claim 12 wherein the first of said pair of diodes is mounted on said probe in proximate relation to said non-conductive base portion for establishing a first selected closed/open circuit adjacent the air/material interface when said probe is inserted into a material to be tested and the second of said pair of diodes is mounted on said probe in proximate relation to the free ends of said first and second conductive means.

14. A probe as set forth in claims 1, 2, 3, 4 or 5 wherein said means for selectively shorting said first conductive means to said second conductive means includes at least one diode and remotely operable switch means for selectively biasing said at least one diode to one of a conductive and non-conductive state.

15. A probe as set forth in claim 6 wherein said remotely operable switch means comprises one of: i) a manually operated switch means; ii) an electromechanically operated switch means; and iii), an electronically operated switch means.

16. A series averaging probe for use with Time Domain Reflectometry apparatus and characterized by its ability to measure the average moisture characteristics of a series of discrete, spaced apart bodies of test media, said series averaging probe comprising, in combination:

a) "n" sets of discrete rigid RF probe conductor pairs, where "n" is any whole integer greater than "1", with the conductors in each pair being parallel and spaced apart by non-conductive dielectric material;

"n"-1 sets of flexible RF coupling cables for coupling said "n" sets on discrete rigid RF probe conductor pairs together in series;

c) a first remotely operable, normally open, variable impedance device electrically connected between said spaced conductors of the first of said "n" pairs adjacent the proximal end thereof;

d) a second remotely operable, normally open, variable impedance device electrically coupled between said spaced conductors of the last of said "n" pairs adjacent the distal end thereof; and, e) means for coupling the proximal end of said first of said "n" pairs of probe conductors to a Time Domain Reflectometry apparatus;

whereby, successive ones of said "n" sets of conductor pairs can be passed through adjacent ones of the "n" discrete spaced apart bodies of test media and coupled together by said flexible RF coupling cables in series so that fast rise time energy pulses propagated down said series averaging probe by the Time Domain Reflectometry apparatus produce reflections attributable to discontinuities along the entire length of said series averaging probe including discontinuities when said first and second remotely operable, normally open, variable impedance devices are shorted, which reflections are returned to the Time Domain Reflectometry apparatus for sampling and processing to thereby produce a measurement representative of the average moisture characteristics of the "n" discrete bodies of test media.

17. A probe as set forth in claim 16 wherein said first and second remotely operable, normally open, variable impedance devices comprise diodes.

* * * * *